(12) United States Patent
Bernstein et al.

(10) Patent No.: US 11,339,442 B2
(45) Date of Patent: May 24, 2022

(54) METHODS OF DETECTING INSULATOR DYSFUNCTION AND ONCOGENE ACTIVATION FOR SCREENING, DIAGNOSIS AND TREATMENT OF PATIENTS IN NEED THEREOF

(71) Applicant: THE GENERAL HOSPITAL CORPORATION, Boston, MA (US)

(72) Inventors: Bradley Bernstein, Cambridge, MA (US); Yotam Drier, Cambridge, MA (US); William Flavahan, Malden, MA (US); Daniel Tarjan, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/061,546

(22) PCT Filed: Dec. 14, 2016

(86) PCT No.: PCT/US2016/066574
§ 371 (c)(1),
(2) Date: Jun. 12, 2018

(87) PCT Pub. No.: WO2017/106290
PCT Pub. Date: Jun. 22, 2017

(65) Prior Publication Data
US 2020/0224274 A1    Jul. 16, 2020

Related U.S. Application Data

(60) Provisional application No. 62/266,908, filed on Dec. 14, 2015, provisional application No. 62/369,282, filed on Aug. 1, 2016.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/154* (2013.01); *C12Q 2600/156* (2013.01)

(58) Field of Classification Search
CPC .................. C12Q 1/6886; C12Q 2600/154
See application file for complete search history.

(56) References Cited

FOREIGN PATENT DOCUMENTS

| WO | 2004010850 A2 | 2/2004 |
|----|---------------|--------|
| WO | 2009084960 A2 | 7/2009 |

OTHER PUBLICATIONS

Nakagawa et al. PNAS. 2001. 98(2):591-596. (Year: 2001).*
(Continued)

*Primary Examiner* — Joseph G. Dauner
(74) *Attorney, Agent, or Firm* — Withers Bergman LLP; Christopher R. Cowles

(57) ABSTRACT

The present application generally to the diagnosis and treatment of diseases resulting from the alteration of chromatin boundaries between topologically-associated domains. In particular, the present application relates to detection of mutations causing DNA hypermethylation phenotypes, CpG methylation within CTCF binding motifs, and aberrant gene expression caused by altered chromatin topology. Applicants show that IDH mutant gliomas exhibit hyper-methylation at CTCF binding sites, compromising binding of this methylation-sensitive insulator protein. Applicants also demonstrate that loss of CTCF at a domain boundary permits a constitutive enhancer to aberrantly interact with the receptor tyrosine kinase gene PDGFRA, a prominent glioma oncogene. Thus, Applicants have uncovered that IDH mutations may promote gliomagenesis by disrupting chromosomal topology and allowing aberrant regulatory interactions that induce oncogene expression.

29 Claims, 36 Drawing Sheets
Specification includes a Sequence Listing.

(56) References Cited

OTHER PUBLICATIONS

Ong et al. Nature Reviews Genetics. 2014. 15:234-246. (Year: 2014).*
Whitehall et al. Epigenetics. 2014. 9(11):1454-1460. (Year: 2014).*
Flavahan et al. Nature. 2016. 529(7584):110-114. (Year: 2016).*
Lai et al. "DNA Methylation Prevents CTCF-Mediated Silencing of the Oncogene BCL6 in B cell Lymphomas" J. Exp. Med. 207(9):1939-1950 (2010).
Zitzmann et al. "Frequent Hypermethylation of a CTCF Binding site Influences Wilms Tumor 1 Expression in Wilms Tumors" Published online: https://doi.org/10.3892/or.2014.3019 (2014).
Toepoel et al. "Haplotype-specific Expression of the Human PDGFRA Gene Correlates with the risk of Glioblastomas" Int. J. Cancer 123:322-329 (2008).
Figueroa et al. "Leukemic IDH1 and IDH2 Mutations Result in a Hypermethylation Phenotype, Disrupt TET2 Function, and Impair Hematopoietic Differentiation" Cancer Cell 18(6):553-567 (2010).
International Search Report issued in corresponding International Application No. PCT/US16/66574, dated May 15, 2017.
International Preliminary Report on Patentability dated Jun. 19, 2018 in PCT/US2016/066574—13 pages.
European Examination Report dated Apr. 10, 2019 for related European Patent Application No. 16820503.7 corresponding to International Application No. PCT/US2016/066574.

* cited by examiner

Figure 2
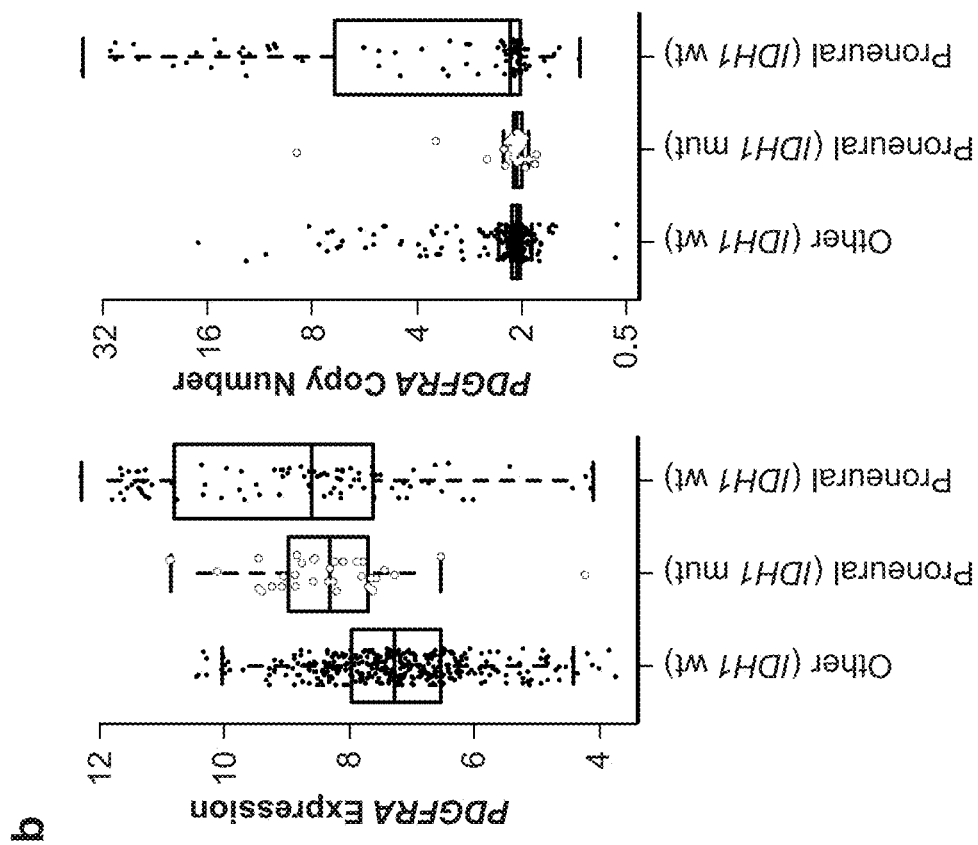
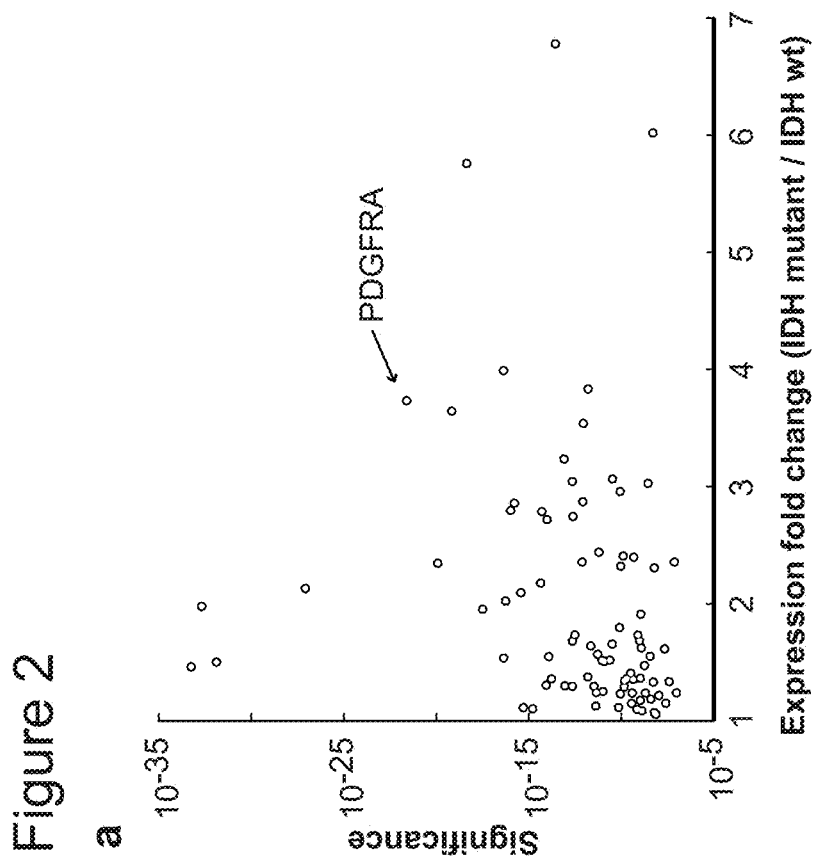

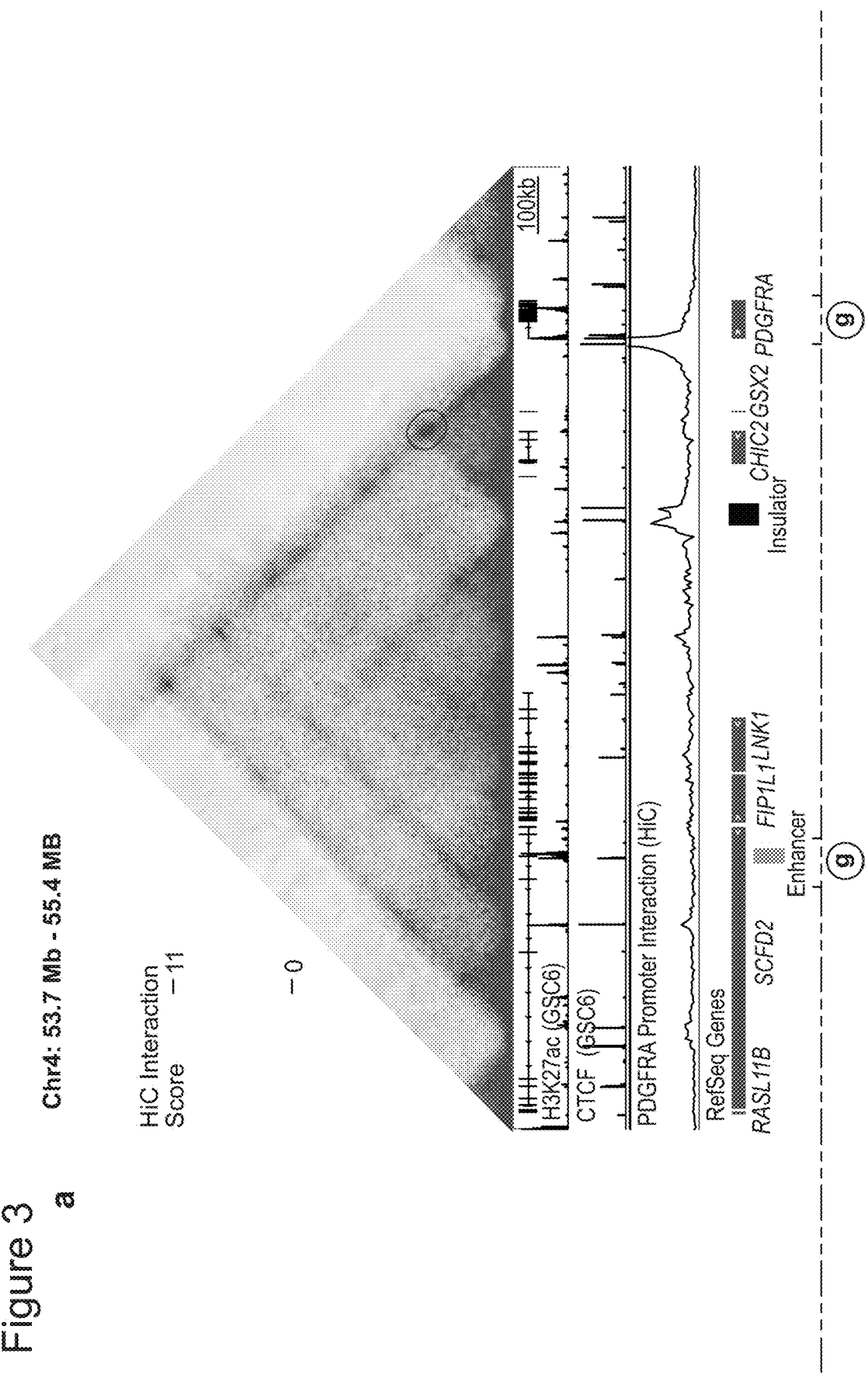

Most Common CRISPR Deletion Sequences

| Sequence | Deletion Size (bp) | Reads |
|---|---|---|
| TAGAACCACACAGATAATGC--------AGATGGCGGCTCACATCCA | 4 | 5.5% |
| TAGAACCACACC-------------AGATGGCGGCTCACATCCA | 13 | 3.9% |
| TAGAACCACACAGATAA----------TGGCCGCTCACATCCA | 10 | 3.7% |
| TAGAACCACACAGATAA-----------GCGGCTCACATCCA | 11 | 0.91% |
| TAGAACCACACAGATAATGCA--------GCGGCTCACATCCA | 8 | 0.30% |
| TAGAACCACACAGATAAT-------GATGGCGGCTCACATCCA | 7 | 0.01% |
| Any other deletion | | 8.1% |

Figure 4 (cont.)
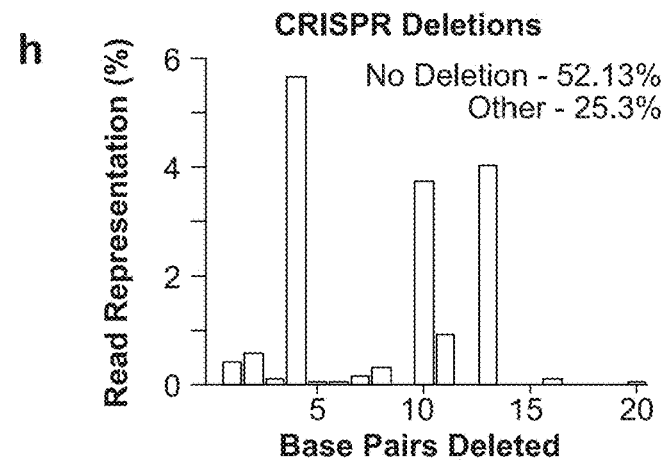
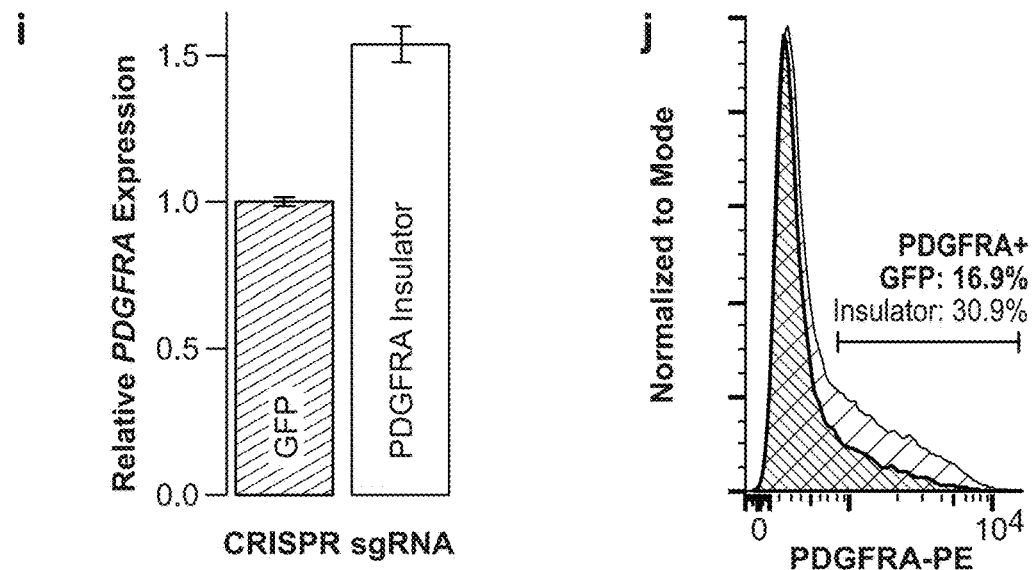
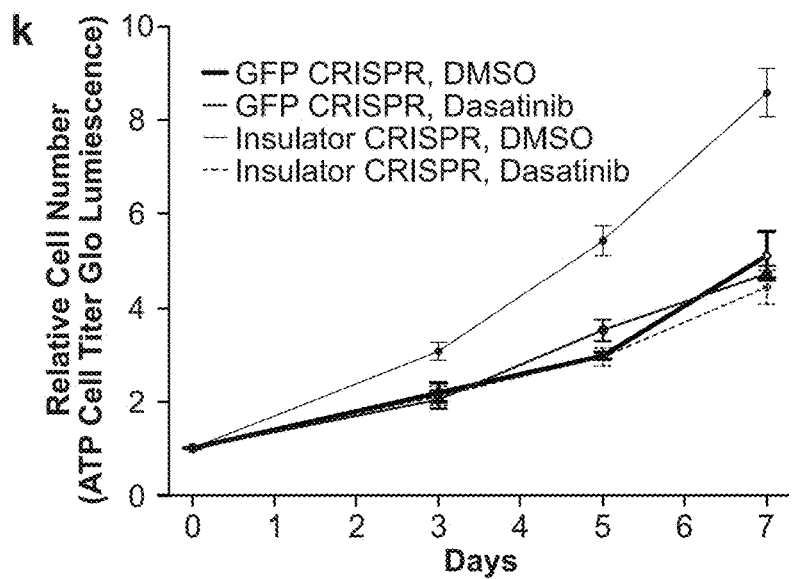

e

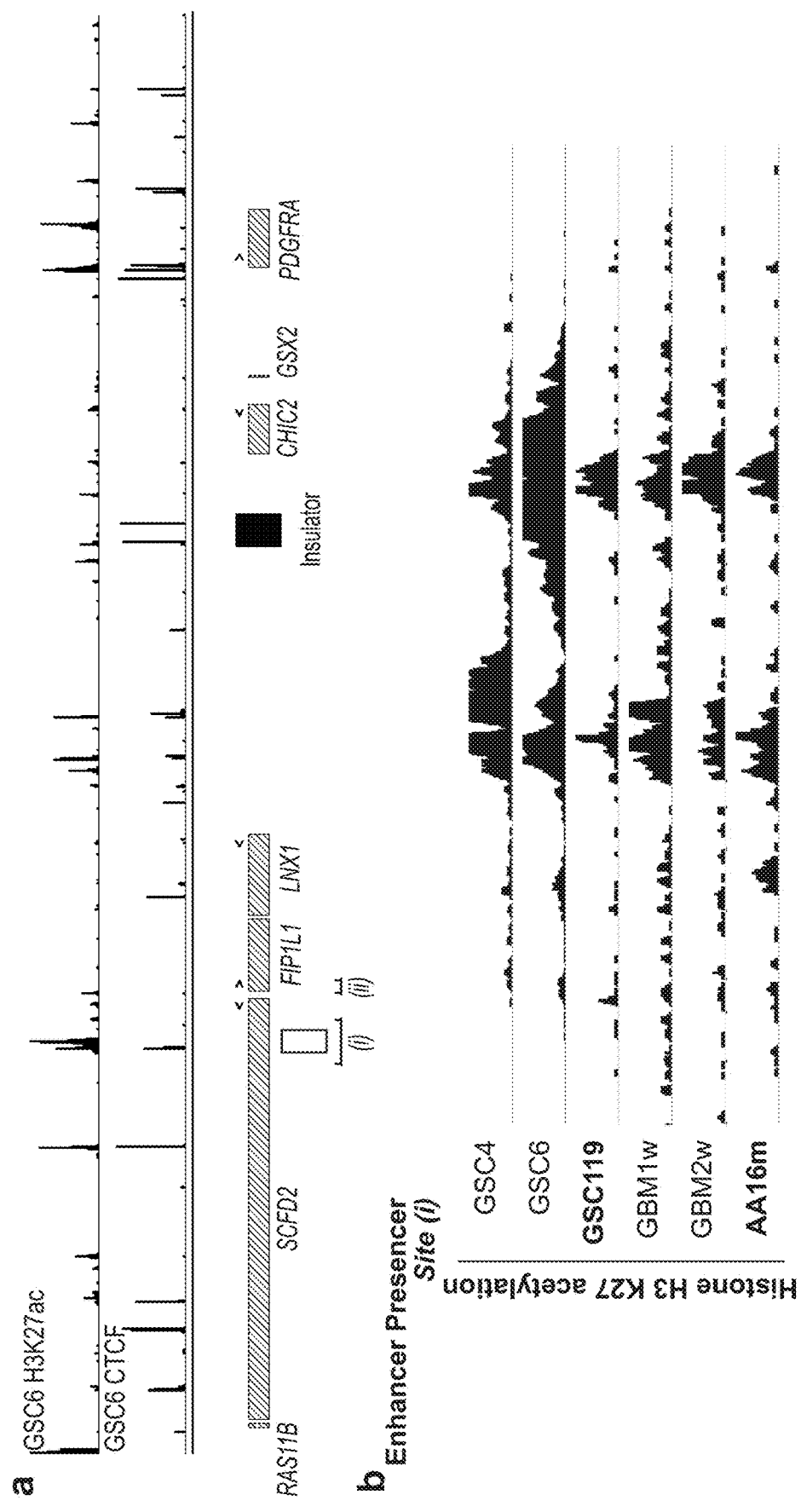

c

Enhancer Characterization

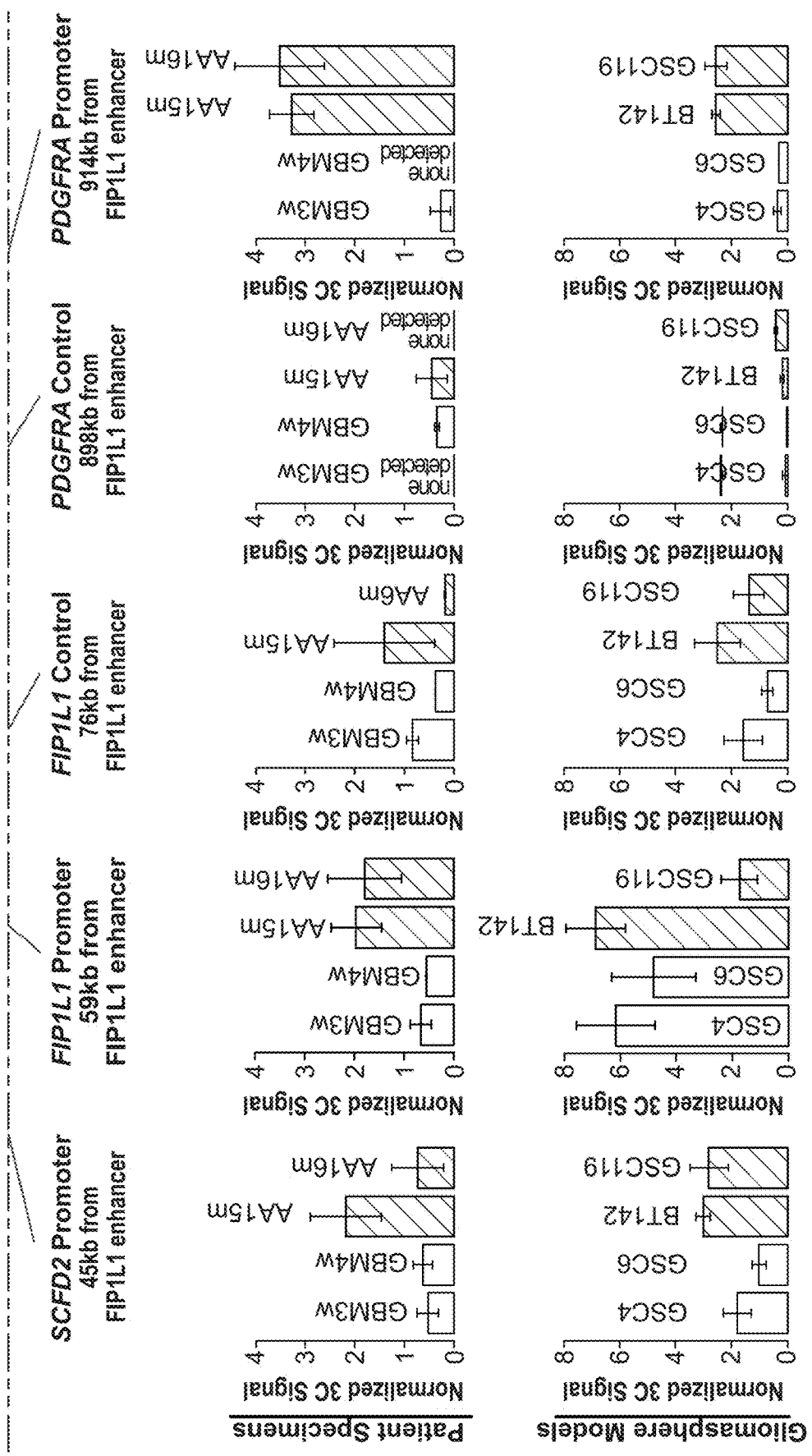

Figure 12

| Glioma | Tissue Type | Tissue Source | Source | IDH1 Status | PDGFRA Status | 1p/19q Status | Grade | Disease |
|---|---|---|---|---|---|---|---|---|
| GBM1w | Autopsy Specimen | Banked | MGH | Wild Type | Amplified | Not tested | IV | Glioblastoma |
| GBM2w | Surgical Specimen | Banked | MGH | Wild Type | Wild Type | Not tested | IV | Glioblastoma |
| GBM3w | Surgical Specimen | Banked | MGH | Wild Type | Wild Type | Not tested | IV | Glioblastoma |
| GBM4w | Surgical Specimen | Banked | MGH | Wild Type | Wild Type | Not tested | IV | Glioblastoma |
| GBM5w | Surgical Specimen | Fresh | MGH | Wild Type | Wild Type | Not tested | IV | Glioblastoma |
| GBM6w | Surgical Specimen | Fresh | MGH | Wild Type | Wild Type | Not tested | IV | Glioblastoma |
| GBM7w | Surgical Specimen | Fresh | MGH | Wild Type | Wild Type | Not tested | IV | Glioblastoma |
| AA15m | Surgical Specimen | Banked | MGH | R132H | Wild Type | Intact | III | Anaplastic Astrocytoma |
| AA16m | Surgical Specimen | Banked | MGH | R132H | Wild Type | Intact | III | Anaplastic Astrocytoma |
| AA17m | Surgical Specimen | Fresh | MGH | R132H | Wild Type | Intact | III | Anaplastic Astrocytoma |
| OD18m | Surgical Specimen | Fresh | MGH | R132H | Wild Type | Lost | II | Oligodendroglioma |
| AA19m | Surgical Specimen | Fresh | MGH | R132H | Wild Type | Intact | III | Anaplastic Astrocytoma |
| GSC4 | Gliomasphere | - | MGH | Wild Type | Wild Type | Intact | IV | Glioblastoma |
| GSC6 | Gliomasphere | - | MGH | Wild Type | Wild Type | Intact | IV | Glioblastoma |
| BT142 | Gliomasphere | - | ATCC | R132H | Wild Type | Intact | III | Anaplastic Oligoastrocytoma |
| GSC119 | Gliomasphere | - | MGH | R132H | Wild Type | Intact | IV | Secondary Glioblastoma |

Figure 13

| Sample Name | Experiment | Sequencing Depth | Sequencing Format | Sequencing Instrument | Total read number (millions) |
|---|---|---|---|---|---|
| GBM1w - CTCF | CTCF ChIP-seq | 38 base pairs | Paired end | Illumina NextSeq 500 | 19.3 |
| GBM2w - CTCF | CTCF ChIP-seq | 38 base pairs | Paired end | Illumina NextSeq 500 | 17.6 |
| GBM3w - CTCF | CTCF ChIP-seq | 38 base pairs | Paired end | Illumina NextSeq 500 | 20.2 |
| GBM5w - CTCF | CTCF ChIP-seq | 38 base pairs | Paired end | Illumina NextSeq 500 | 30 |
| GBM6w - CTCF | CTCF ChIP-seq | 38 base pairs | Paired end | Illumina NextSeq 500 | 35.1 |
| GBM7w - CTCF | CTCF ChIP-seq | 38 base pairs | Paired end | Illumina NextSeq 500 | 36 |
| AA15m - CTCF | CTCF ChIP-seq | 38 base pairs | Paired end | Illumina NextSeq 500 | 8.7 |
| AA16m - CTCF | CTCF ChIP-seq | 38 base pairs | Paired end | Illumina NextSeq 500 | 23.7 |
| AA17m - CTCF | CTCF ChIP-seq | 38 base pairs | Paired end | Illumina NextSeq 500 | 16.3 |
| OD18m - CTCF | CTCF ChIP-seq | 38 base pairs | Paired end | Illumina NextSeq 500 | 9.2 |
| AA19m - CTCF | CTCF ChIP-seq | 38 base pairs | Paired end | Illumina NextSeq 500 | 33 |
| GSC4 - CTCF | CTCF ChIP-seq | 38 base pairs | Paired end | Illumina NextSeq 500 | 19.9 |
| GSC6 - CTCF | CTCF ChIP-seq | 38 base pairs | Paired end | Illumina NextSeq 500 | 21.9 |
| BT142 - CTCF | CTCF ChIP-seq | 38 base pairs | Paired end | Illumina NextSeq 500 | 16 |
| GSC119 - CTCF | CTCF ChIP-seq | 50 base pairs | Single end | Illumina Miseq | 6.39 |
| GBM1w - H3K27ac | H3K27ac ChIP-seq | 38 base pairs | Paired end | Illumina NextSeq 500 | 12.7 |
| GBM2w - H3K27ac | H3K27ac ChIP-seq | 38 base pairs | Paired end | Illumina NextSeq 500 | 10.8 |
| AA15m - H3K27ac | H3K27ac ChIP-seq | 38 base pairs | Paired end | Illumina NextSeq 500 | 11.8 |

Figure 13 (cont.)

| | | | | |
|---|---|---|---|---|
| GSC4 - H3K27ac | H3K27ac ChIP-seq | 38 base pairs | Paired end | Illumina NextSeq 500 | 9.7 |
| GSC6 - H3K27ac | H3K27ac ChIP-seq | 36 base pairs | Single end | Illumina Hiseq 2500 | 10.5 |
| GSC119 - H3K27ac | H3K27ac ChIP-seq | 38 base pairs | Paired end | Illumina NextSeq 500 | 9 |
| GSC6 CRISPR - GFP sgRNA | Locus Sequencing | 50 base pairs | Single end | Illumina Miseq | 0.539 |
| GSC6 CRISPR - insulator sgRNA | Locus Sequencing | 50 base pairs | Single end | Illumina Miseq | 0.639 |
| GSC4 bisulfite | Bisulfite Sequncing | 38 base pairs | Paired end | Illumina NextSeq 500 | 0.149 |
| GSC6 bisulfite | Bisulfite Sequncing | 38 base pairs | Paired end | Illumina NextSeq 500 | 0.149 |
| BT142 bisulfite | Bisulfite Sequncing | 38 base pairs | Paired end | Illumina NextSeq 500 | 0.149 |
| GSC119 bisulfite | Bisulfite Sequncing | 38 base pairs | Paired end | Illumina NextSeq 500 | 0.156 |

SEQUENCE LISTING

<160> NUMBER OF SEQ ID NOS: 65

<210> SEQ ID NO 1
<211> LENGTH: 19
<212> TYPE: DNA
<213> ORGANISM: Artificial
<220> FEATURE:
<223> OTHER INFORMATION: Synthetic

<400> SEQUENCE: 1
atgcagctag atggcgctc                                                    19

<210> SEQ ID NO 2
<211> LENGTH: 40
<212> TYPE: DNA
<213> ORGANISM: Artificial
<220> FEATURE:
<223> OTHER INFORMATION: Synthetic

<400> SEQUENCE: 2
tagaaccaca gataatgcag ctagatggcg ctcacatcca                             40

<210> SEQ ID NO 3
<211> LENGTH: 36
<212> TYPE: DNA
<213> ORGANISM: Artificial
<220> FEATURE:
<223> OTHER INFORMATION: Synthetic

<400> SEQUENCE: 3
tagaaccaca gataatgcag atggcgctca catcca                                 36

<210> SEQ ID NO 4
<211> LENGTH: 27
<212> TYPE: DNA
<213> ORGANISM: Artificial
<220> FEATURE:
<223> OTHER INFORMATION: Synthetic

<400> SEQUENCE: 4
tagaaccaca gatggcgctc acatcca                                           27

<210> SEQ ID NO 5
<211> LENGTH: 30
<212> TYPE: DNA
<213> ORGANISM: Artificial
<220> FEATURE:
<223> OTHER INFORMATION: Synthetic

<400> SEQUENCE: 5
tagaaccaca gataatggcg ctcacatcca                                        30

<210> SEQ ID NO 6
<211> LENGTH: 29
<212> TYPE: DNA
<213> ORGANISM: Artificial
<220> FEATURE:
<223> OTHER INFORMATION: Synthetic

<400> SEQUENCE: 6
tagaaccaca gataatgcgc tcacatcca                                         29

<210> SEQ ID NO 7
<211> LENGTH: 32
<212> TYPE: DNA

<213> ORGANISM: Artificial
<220> FEATURE:
<223> OTHER INFORMATION: Synthetic

<400> SEQUENCE: 7
tagaaccaca gataatgcag cgctcacatc ca                            32

<210> SEQ ID NO 8
<211> LENGTH: 33
<212> TYPE: DNA
<213> ORGANISM: Artificial
<220> FEATURE:
<223> OTHER INFORMATION: Synthetic

<400> SEQUENCE: 8
tagaaccaca gataatgatg gcgctcacat cca                           33

<210> SEQ ID NO 9
<211> LENGTH: 7
<212> TYPE: PRT
<213> ORGANISM: Artificial
<220> FEATURE:
<223> OTHER INFORMATION: Synthetic

<400> SEQUENCE: 9

Pro Lys Lys Lys Arg Lys Val
1               5

<210> SEQ ID NO 10
<211> LENGTH: 16
<212> TYPE: PRT
<213> ORGANISM: Artificial
<220> FEATURE:
<223> OTHER INFORMATION: Synthetic

<400> SEQUENCE: 10

Lys Arg Pro Ala Ala Thr Lys Lys Ala Gly Gln Ala Lys Lys Lys Lys
1               5                   10                  15

<210> SEQ ID NO 11
<211> LENGTH: 9
<212> TYPE: PRT
<213> ORGANISM: Artificial
<220> FEATURE:
<223> OTHER INFORMATION: Synthetic

<400> SEQUENCE: 11

Pro Ala Ala Lys Arg Val Lys Leu Asp
1               5

<210> SEQ ID NO 12
<211> LENGTH: 11
<212> TYPE: PRT
<213> ORGANISM: Artificial
<220> FEATURE:
<223> OTHER INFORMATION: Synthetic

<400> SEQUENCE: 12

Arg Gln Arg Arg Asn Glu Leu Lys Arg Ser Pro
1               5                   10

<210> SEQ ID NO 13
<211> LENGTH: 38
<212> TYPE: PRT
<213> ORGANISM: Artificial
<220> FEATURE:
<223> OTHER INFORMATION: Synthetic

<400> SEQUENCE: 13

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 14
<211> LENGTH: 42
<212> TYPE: PRT
<213> ORGANISM: Artificial
<220> FEATURE:
<223> OTHER INFORMATION: Synthetic

<400> SEQUENCE: 14

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 15
<211> LENGTH: 8
<212> TYPE: PRT
<213> ORGANISM: Artificial
<220> FEATURE:
<223> OTHER INFORMATION: Synthetic

<400> SEQUENCE: 15

Val Ser Arg Lys Arg Pro Arg Pro
1               5

<210> SEQ ID NO 16
<211> LENGTH: 8
<212> TYPE: PRT
<213> ORGANISM: Artificial
<220> FEATURE:
<223> OTHER INFORMATION: Synthetic

<400> SEQUENCE: 16

Pro Pro Lys Lys Ala Arg Glu Asp
1               5

<210> SEQ ID NO 17
<211> LENGTH: 8
<212> TYPE: PRT
<213> ORGANISM: Artificial
<220> FEATURE:
<223> OTHER INFORMATION: Synthetic

<400> SEQUENCE: 17

Pro Gln Pro Lys Lys Lys Pro Leu
1               5

<210> SEQ ID NO 18
<211> LENGTH: 12
<212> TYPE: PRT
<213> ORGANISM: Artificial
<220> FEATURE:
<223> OTHER INFORMATION: Synthetic

<400> SEQUENCE: 18

```
Ser Ala Leu Ile Lys Lys Lys Lys Met Ala Pro
1               5                   10
```

<210> SEQ ID NO 19
<211> LENGTH: 5
<212> TYPE: PRT
<213> ORGANISM: Artificial
<220> FEATURE:
<223> OTHER INFORMATION: Synthetic

<400> SEQUENCE: 19

```
Asp Arg Leu Arg Arg
1               5
```

<210> SEQ ID NO 20
<211> LENGTH: 7
<212> TYPE: PRT
<213> ORGANISM: Artificial
<220> FEATURE:
<223> OTHER INFORMATION: Synthetic

<400> SEQUENCE: 20

```
Pro Lys Gln Lys Lys Arg Lys
1               5
```

<210> SEQ ID NO 21
<211> LENGTH: 10
<212> TYPE: PRT
<213> ORGANISM: Artificial
<220> FEATURE:
<223> OTHER INFORMATION: Synthetic

<400> SEQUENCE: 21

```
Arg Lys Leu Lys Lys Lys Ile Lys Lys Leu
1               5                   10
```

<210> SEQ ID NO 22
<211> LENGTH: 10
<212> TYPE: PRT
<213> ORGANISM: Artificial
<220> FEATURE:
<223> OTHER INFORMATION: Synthetic

<400> SEQUENCE: 22

```
Arg Glu Lys Lys Lys Phe Leu Lys Arg Arg
1               5                   10
```

<210> SEQ ID NO 23
<211> LENGTH: 20
<212> TYPE: PRT
<213> ORGANISM: Artificial
<220> FEATURE:
<223> OTHER INFORMATION: Synthetic

<400> SEQUENCE: 23

```
Lys Arg Lys Gly Asp Glu Val Asp Gly Val Asp Glu Val Ala Lys Lys
1               5                   10                  15

Lys Ser Lys Lys
            20
```

<210> SEQ ID NO 24
<211> LENGTH: 17
<212> TYPE: PRT
<213> ORGANISM: Artificial
<220> FEATURE:
<223> OTHER INFORMATION: Synthetic

<400> SEQUENCE: 24

Arg Lys Cys Leu Gln Ala Gly Met Asn Leu Glu Ala Arg Lys Thr Lys
1               5                   10                  15

Lys

<210> SEQ ID NO 25
<211> LENGTH: 288
<212> TYPE: PRT
<213> ORGANISM: Artificial
<220> FEATURE:
<223> OTHER INFORMATION: Synthetic

<400> SEQUENCE: 25

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

<210> SEQ ID NO 26
<211> LENGTH: 183
<212> TYPE: PRT
<213> ORGANISM: Artificial
<220> FEATURE:
<223> OTHER INFORMATION: Synthetic

<400> SEQUENCE: 26

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 27
<211> LENGTH: 20
<212> TYPE: DNA
<213> ORGANISM: Artificial
<220> FEATURE:
<223> OTHER INFORMATION: Synthetic

<400> SEQUENCE: 27
gtcacagtag aaccacagat                                            20

<210> SEQ ID NO 28
<211> LENGTH: 20
<212> TYPE: DNA
<213> ORGANISM: Artificial
<220> FEATURE:
<223> OTHER INFORMATION: Synthetic

<400> SEQUENCE: 28
taagtatact ggtcctcctc                                            20

<210> SEQ ID NO 29
<211> LENGTH: 20
<212> TYPE: DNA
<213> ORGANISM: Artificial
<220> FEATURE:
<223> OTHER INFORMATION: Synthetic

<400> SEQUENCE: 29
ccttcctagt cactcagtaa                                            20

<210> SEQ ID NO 30
<211> LENGTH: 18
<212> TYPE: DNA

```
<213> ORGANISM: Artificial
<220> FEATURE:
<223> OTHER INFORMATION: Synthetic

<400> SEQUENCE: 30
cagtgttgac tcatccag                                                 18

<210> SEQ ID NO 31
<211> LENGTH: 18
<212> TYPE: DNA
<213> ORGANISM: Artificial
<220> FEATURE:
<223> OTHER INFORMATION: Synthetic

<400> SEQUENCE: 31
cagtaccagc ctctctag                                                 18

<210> SEQ ID NO 32
<211> LENGTH: 18
<212> TYPE: DNA
<213> ORGANISM: Artificial
<220> FEATURE:
<223> OTHER INFORMATION: Synthetic

<400> SEQUENCE: 32
ctaagctagg ccttcaag                                                 18

<210> SEQ ID NO 33
<211> LENGTH: 25
<212> TYPE: DNA
<213> ORGANISM: Artificial
<220> FEATURE:
<223> OTHER INFORMATION: Synthetic

<400> SEQUENCE: 33
gaattataga taatgtagtt agagg                                         25

<210> SEQ ID NO 34
<211> LENGTH: 26
<212> TYPE: DNA
<213> ORGANISM: Artificial
<220> FEATURE:
<223> OTHER INFORMATION: Synthetic

<400> SEQUENCE: 34
aaatatacta atcctcctct cccaaa                                        26

<210> SEQ ID NO 35
<211> LENGTH: 20
<212> TYPE: DNA
<213> ORGANISM: Artificial
<220> FEATURE:
<223> OTHER INFORMATION: Synthetic

<400> SEQUENCE: 35
cgtgagctga attgtgcctg                                               20

<210> SEQ ID NO 36
<211> LENGTH: 20
<212> TYPE: DNA
<213> ORGANISM: Artificial
<220> FEATURE:
<223> OTHER INFORMATION: Synthetic

<400> SEQUENCE: 36
tgggaggaca gtttagggct                                               20
```

```
<210> SEQ ID NO 37
<211> LENGTH: 17
<212> TYPE: DNA
<213> ORGANISM: Artificial
<220> FEATURE:
<223> OTHER INFORMATION: Synthetic

<400> SEQUENCE: 37
ggtcgtgcct ttgtttt                                                  17

<210> SEQ ID NO 38
<211> LENGTH: 19
<212> TYPE: DNA
<213> ORGANISM: Artificial
<220> FEATURE:
<223> OTHER INFORMATION: Synthetic

<400> SEQUENCE: 38
cagggaagag aggaagttt                                                19

<210> SEQ ID NO 39
<211> LENGTH: 23
<212> TYPE: DNA
<213> ORGANISM: Artificial
<220> FEATURE:
<223> OTHER INFORMATION: Synthetic

<400> SEQUENCE: 39
ttaagtaagc aggtaaacta cat                                           23

<210> SEQ ID NO 40
<211> LENGTH: 17
<212> TYPE: DNA
<213> ORGANISM: Artificial
<220> FEATURE:
<223> OTHER INFORMATION: Synthetic

<400> SEQUENCE: 40
agcctttgcc tccttt                                                   17

<210> SEQ ID NO 41
<211> LENGTH: 18
<212> TYPE: DNA
<213> ORGANISM: Artificial
<220> FEATURE:
<223> OTHER INFORMATION: Synthetic

<400> SEQUENCE: 41
ccacagggag aaggaaat                                                 18

<210> SEQ ID NO 42
<211> LENGTH: 19
<212> TYPE: DNA
<213> ORGANISM: Artificial
<220> FEATURE:
<223> OTHER INFORMATION: Synthetic

<400> SEQUENCE: 42
caaggaattc gtagggttc                                                19

<210> SEQ ID NO 43
<211> LENGTH: 9
<212> TYPE: DNA
<213> ORGANISM: Artificial
<220> FEATURE:
```

<223> OTHER INFORMATION: Synthetic

<400> SEQUENCE: 43 ttgtatgcg                                                                                        9

<210> SEQ ID NO 44
<211> LENGTH: 18
<212> TYPE: DNA
<213> ORGANISM: Artificial
<220> FEATURE:
<223> OTHER INFORMATION: Synthetic

<400> SEQUENCE: 44
agatagaagc cagggcaa                                                                             18

<210> SEQ ID NO 45
<211> LENGTH: 20
<212> TYPE: DNA
<213> ORGANISM: Artificial
<220> FEATURE:
<223> OTHER INFORMATION: Synthetic

<400> SEQUENCE: 45
aatacatggt catgatgctc                                                                           20

<210> SEQ ID NO 46
<211> LENGTH: 20
<212> TYPE: DNA
<213> ORGANISM: Artificial
<220> FEATURE:
<223> OTHER INFORMATION: Synthetic

<400> SEQUENCE: 46
aggcattgct taaacataac                                                                           20

<210> SEQ ID NO 47
<211> LENGTH: 9
<212> TYPE: DNA
<213> ORGANISM: Artificial
<220> FEATURE:
<223> OTHER INFORMATION: Synthetic

<400> SEQUENCE: 47 tatcccaac                                                                                        9

<210> SEQ ID NO 48
<211> LENGTH: 15
<212> TYPE: DNA
<213> ORGANISM: Artificial
<220> FEATURE:
<223> OTHER INFORMATION: Synthetic

<400> SEQUENCE: 48
caaatacagg gcttg                                                                                15

<210> SEQ ID NO 49
<211> LENGTH: 20
<212> TYPE: DNA
<213> ORGANISM: Artificial
<220> FEATURE:
<223> OTHER INFORMATION: Synthetic

<400> SEQUENCE: 49
atgataacac caccattcag                                                                           20

```
<210> SEQ ID NO 50
<211> LENGTH: 24
<212> TYPE: DNA
<213> ORGANISM: Artificial
<220> FEATURE:
<223> OTHER INFORMATION: Synthetic

<400> SEQUENCE: 50
tatcccaacc aaatacaggg cttg                                          24

<210> SEQ ID NO 51
<211> LENGTH: 20
<212> TYPE: DNA
<213> ORGANISM: Artificial
<220> FEATURE:
<223> OTHER INFORMATION: Synthetic

<400> SEQUENCE: 51
ttcgtctcag ccaatccctg                                               20

<210> SEQ ID NO 52
<211> LENGTH: 20
<212> TYPE: DNA
<213> ORGANISM: Artificial
<220> FEATURE:
<223> OTHER INFORMATION: Synthetic

<400> SEQUENCE: 52
tttgcccatg gtgaaaacgg                                               20

<210> SEQ ID NO 53
<211> LENGTH: 20
<212> TYPE: DNA
<213> ORGANISM: Artificial
<220> FEATURE:
<223> OTHER INFORMATION: Synthetic

<400> SEQUENCE: 53
ggttcatcat gccgtttgtg                                               20

<210> SEQ ID NO 54
<211> LENGTH: 21
<212> TYPE: DNA
<213> ORGANISM: Artificial
<220> FEATURE:
<223> OTHER INFORMATION: Synthetic

<400> SEQUENCE: 54
ccactcatcg cagtactgtt g                                             21

<210> SEQ ID NO 55
<211> LENGTH: 20
<212> TYPE: DNA
<213> ORGANISM: Artificial
<220> FEATURE:
<223> OTHER INFORMATION: Synthetic

<400> SEQUENCE: 55
gagctggacg gcgacgtaaa                                               20

<210> SEQ ID NO 56
<211> LENGTH: 21
<212> TYPE: DNA
<213> ORGANISM: Artificial
<220> FEATURE:
<223> OTHER INFORMATION: Synthetic
```

```
<400> SEQUENCE: 56
gccacagata atgcagctag a                                              21

<210> SEQ ID NO 57
<211> LENGTH: 20
<212> TYPE: DNA
<213> ORGANISM: Artificial
<220> FEATURE:
<223> OTHER INFORMATION: Synthetic

<400> SEQUENCE: 57
tttgcaatgg gacacggaga                                                20

<210> SEQ ID NO 58
<211> LENGTH: 21
<212> TYPE: DNA
<213> ORGANISM: Artificial
<220> FEATURE:
<223> OTHER INFORMATION: Synthetic

<400> SEQUENCE: 58
agaaatgtgt ggatgtgagc g                                              21

<210> SEQ ID NO 59
<211> LENGTH: 20
<212> TYPE: DNA
<213> ORGANISM: Artificial
<220> FEATURE:
<223> OTHER INFORMATION: Synthetic

<400> SEQUENCE: 59
gctcagccct gtgagaagac                                                20

<210> SEQ ID NO 60
<211> LENGTH: 20
<212> TYPE: DNA
<213> ORGANISM: Artificial
<220> FEATURE:
<223> OTHER INFORMATION: Synthetic

<400> SEQUENCE: 60
attgcggaat aacatcggag                                                20

<210> SEQ ID NO 61
<211> LENGTH: 21
<212> TYPE: DNA
<213> ORGANISM: Artificial
<220> FEATURE:
<223> OTHER INFORMATION: Synthetic

<400> SEQUENCE: 61
tcccacttgc tgaaaaggtc a                                              21

<210> SEQ ID NO 62
<211> LENGTH: 20
<212> TYPE: DNA
<213> ORGANISM: Artificial
<220> FEATURE:
<223> OTHER INFORMATION: Synthetic

<400> SEQUENCE: 62
ccgactcttc cttggcttca                                                20

<210> SEQ ID NO 63
<211> LENGTH: 20
```

```
<212> TYPE: DNA
<213> ORGANISM: Artificial
<220> FEATURE:
<223> OTHER INFORMATION: Synthetic

<400> SEQUENCE: 63
agaaaatctg gcaccacacc                                               20

<210> SEQ ID NO 64
<211> LENGTH: 20
<212> TYPE: DNA
<213> ORGANISM: Artificial
<220> FEATURE:
<223> OTHER INFORMATION: Synthetic

<400> SEQUENCE: 64
agaggcgtac agggatagca                                               20

<210> SEQ ID NO 65
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 65

Ala Xaa Ala Ala Xaa Ala Ala Xaa Ala Ala Xaa Ala
1               5                   10
```

METHODS OF DETECTING INSULATOR DYSFUNCTION AND ONCOGENE ACTIVATION FOR SCREENING, DIAGNOSIS AND TREATMENT OF PATIENTS IN NEED THEREOF

RELATED APPLICATIONS AND INCORPORATION BY REFERENCE

This application is the U.S. national stage pursuant to 35 U.S.C. § 371, of United States International Application Ser. No. PCT/US2016/066574, filed Dec. 14, 2016 and published in English on Jun. 22, 2017 as publication WO 2017/106290, which claims priority and benefit of U.S. provisional application Ser. No. 62/266,908 filed Dec. 14, 2015 and 62/369,282 filed Aug. 1, 2016.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant No. HG006991 awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Mar. 30, 2020, is named 52199_526N01_SL.txt and is 28.9 kB in size.

FIELD OF THE INVENTION

The present invention relates generally to the diagnosis and treatment of diseases resulting from the alteration of chromatin boundaries between topologically-associated domains. In particular, the present invention relates to detection of mutations causing DNA hypermethylation phenotypes, CpG methylation within CTCF binding motifs, and aberrant gene expression caused by altered chromatin topology. The present invention further relates to methods of altering chromatin topology by altering a boundary.

BACKGROUND OF THE INVENTION

Gain-of-function IDH mutations are initiating events that define major clinical and prognostic classes of gliomas[1,2]. Mutant IDH protein produces a novel onco-metabolite, 2-hydroxyglutarate (2-HG), that interferes with iron-dependent hydroxylases, including the TET family of 5'-methylcytosine hydroxylases[3-7]. TET enzymes catalyze a key step in the removal of DNA methylation[8,9]. IDH mutant gliomas thus manifest a CpG island methylator phenotype (G-CIMP)[10,11], though the functional significance of this altered epigenetic state remains unclear.

The human genome is organized into topological domains that represent discrete structural and regulatory units[12]. Such domains are evident in genome-wide contact maps generated by HiC[13], and have been termed 'topologically-associated domains' (TAD) or 'contact domains'[14-16]. Recent studies have solidified the role of the CTCF insulator protein in creating chromatin loops and boundaries that partition such domains[15]. Genomic alterations that remove CTCF-associated boundaries allow aberrant enhancer-gene interactions and alter gene expression[17]. Thus there is a need to understand the regulation of CTCF-associated boundaries in healthy and diseased states.

Citation or identification of any document in this application is not an admission that such document is available as prior art to the present invention.

SUMMARY OF THE INVENTION

It is an object of the present invention to provide novel diagnostic methods and treatments for cancer based on the novel finding that IDH mutations in gliomas cause DNA hypermethylation at CpG sites within CTCF binding motifs resulting in reduced CTCF binding, loss of insulation function, and aberrant oncogene activation.

In one aspect, the present invention provides a method of detecting cancer in a subject comprising detecting in a biological sample obtained from the subject altered chromatin topology within a chromatin region, wherein said chromatin region comprises at least one distinct topologically-associated domain partitioned by insulator sites, wherein at least one of said insulator sites comprises a CpG dinucleotide within a CTCF binding motif, and wherein the chromatin region comprises an oncogene, whereby the detection of altered chromatin topology is indicative of cancer in said subject. The chromatin region may have two or more topologically-associated domains. Each topologically-associated domain may have at least one insulator site comprising a CpG dinucleotide within a CTCF binding motif. At least one other domain may comprise a regulatory element. The regulatory element may be an enhancer. The enhancer may aberrantly interact with the oncogene causing over expression. In one embodiment, two or more topologically-associated domains may be in the chromatin region, such that one may include an oncogene and the other a regulatory element, whereby altered chromatin topology within a chromatin region may allow interaction between the oncogene and regulatory element.

The subject may be at high risk for developing cancer. The subject may be in cancer remission, has a genetic disorder which predisposes a subject to cancer, or has been exposed to a carcinogen. The biological sample may be blood, sputum, saliva, urine, tumor tissue, lymphatic fluid, semen, feces, biopsy, or circulating tumor cells. The detecting altered chromatin topology may comprise detecting 5-methyl cytosine at the CpG dinucleotide. The detecting altered chromatin topology may comprise detecting 5-hydroxymethylcytosine at the CpG dinucleotide. The method may further comprise detecting a gain of function mutation in the gene encoding isocitrate dehydrogenase (IDH) or a loss of function mutation in a gene encoding a succinate dehydrogenase. The cancer may be a cholangiocarcinoma, leukemia, a chondrosarcoma, a gastrointestinal stromal tumor (GIST), a pheochromocytoma, a paraganglioma, breast cancer, thyroid cancer, colon cancer, melanoma, bladder cancer, ovarian cancer, lung cancer, glioma, kidney cancer, stomach cancer, pancreatic cancer, liver cancer, or neuroblastoma. The genetic disorder may be Ollier Disease, Mafucci syndrome, Carney-Stratakis Syndrome, or a variant of Cowden Syndrome which predisposes to breast and thyroid cancer. The oncogene may be PDGFRA, FGFR2, other RTKs, or other tumorigenic drivers. The altered chromatin topology may be detected by chromosome conformation capture (3C), DNA hypersensitivity, CTCF binding, methylation specific PCR, Ms-SNuPE, bisulfite sequencing, methylation sensitive restriction digest, nanopore sequencing or DNA FISH.

In another aspect, the present invention provides a method of monitoring disease progression in a subject diagnosed with cancer or a genetic disorder which predisposes the subject to cancer comprising detecting in a biological sample obtained from the subject after diagnosis, altered chromatin topology within a chromatin region, wherein said chromatin region comprises at least one distinct topologically-associated domain partitioned by insulator sites, wherein at least one of said insulator sites comprises a CpG dinucleotide within a CTCF binding motif, and wherein the chromatin region comprises an oncogene, whereby an increase in the detection of altered chromatin topology is an indication of rapid disease progression. The biological sample may be taken directly after diagnosis, before the initiation of treatment, after intiation of treatment, after the duration of a treatment, or after surgery to resect a tumor. The monitoring may be more than one time point. For example, every week, month, year, five years, or ten years. The chromatin region may comprise a regulatory element. The regulatory element may be an enhancer. The biological sample may be blood, sputum, saliva, urine, tumor tissue, lymphatic fluid, semen, feces, biopsy, or circulating tumor cells. The detecting altered chromatin topology may comprise detecting 5-methyl cytosine at the CpG dinucleotide. The detecting altered chromatin topology may comprise detecting 5-hydroxymethylcytosine at the CpG dinucleotide. The method may further comprise detecting a gain of function mutation in the gene encoding isocitrate dehydrogenase (IDH) or a loss of function mutation in a gene encoding a succinate dehydrogenase. The cancer may be a cholangiocarcinoma, leukemia, a chondrosarcoma, a gastrointestinal stromal tumor (GIST), a pheochromocytoma, a paraganglioma, breast cancer, thyroid cancer, colon cancer, melanoma, bladder cancer, ovarian cancer, lung cancer, glioma, kidney cancer, stomach cancer, pancreatic cancer, liver cancer, or neuroblastoma. The genetic disorder may be Ollier Disease, Mafucci syndrome, Carney-Stratakis Syndrome, or a variant of Cowden Syndrome which predisposes to breast and thyroid cancer. The oncogene may be PDGFRA, FGFR2, other RTKs, or other tumorigenic drivers. The altered chromatin topology may be detected by chromosome conformation capture (3C), DNA hypersensitivity, CTCF binding, methylation specific PCR, Ms-SNuPE, bisulfate sequencing, methylation sensitive restriction digest, nanopore sequencing or DNA FISH.

In another aspect, the present invention provides a diagnostic method for selecting a subject to be administered a pharmaceutical composition, wherein the subject has cancer or a genetic disorder which predisposes the subject to cancer, said method comprising detecting altered chromatin topology within a chromatin region, wherein said chromatin region comprises at least one distinct topologically-associated domain partitioned by insulator sites, wherein at least one of said insulator sites comprises a CpG dinucleotide within a CTCF binding motif, and wherein the chromatin region comprises an oncogene, whereby a subject is selected if altered chromatin topology is detected. The chromatin region may comprise a regulatory element. The regulatory element may be an enhancer. The detecting altered chromatin topology may comprise detecting 5-methyl cytosine at the CpG dinucleotide, whereby a subject is selected if 5-methyl cytosine is detected. The detecting altered chromatin topology may comprise detecting 5-hydroxymethylcytosine at the CpG dinucleotide, whereby a subject is selected if 5-hydroxymethylcytosine is detected. The method may further comprise detecting a gain of function mutation in the gene encoding isocitrate dehydrogenase (IDH) or a loss of function mutation in a gene encoding a succinate dehydrogenase. The altered chromatin topology may be detected in a biological sample, wherein said biological sample is blood, sputum, saliva, urine, tumor tissue, lymphatic fluid, semen, feces, biopsy, or circulating tumor cells. The cancer may be a cholangiocarcinoma, leukemia, a chondrosarcoma, a gastrointestinal stromal tumor (GIST), a pheochromocytoma, a paraganglioma, breast cancer, thyroid cancer, colon cancer, melanoma, bladder cancer, ovarian cancer, lung cancer, glioma, kidney cancer, stomach cancer, pancreatic cancer, liver cancer, or neuroblastoma. The genetic disorder may be Ollier Disease, Mafucci syndrome, Carney-Stratakis Syndrome, or a variant of Cowden Syndrome which predisposes to breast and thyroid cancer. The oncogene may be PDGFRA, FGFR2, other RTKs, or other tumorigenic drivers. The pharmaceutical composition may comprise an agent that alters the topology of a chromatin domain. The agent that alters the topology of a chromatin domain may comprise an agent that alters an epigenetic mark within the chromatin domain. In one embodiment, the epigenetic mark is altered within at least one insulator site at the boundary of a topological associated domain. The agent may alter histone acetylation, histone methylation or DNA methylation. The pharmaceutical composition may comprise an inhibitor of the oncogene. The oncogene may be PDGFRA. The inhibitor may be imatinib, crenolanib, or dasatinib. The pharmaceutical composition may comprise an inhibitor of a dehydrogenase. The dehydrogenase may be isocitrate dehydrogenase (IDH). The pharmaceutical composition may comprise an agent that edits the DNA sequence or the DNA methylation within the insulator site. The agent may be a CRISPR-Cas system, TALE, or Zinc-finger. As described herein, the CRISPR-Cas system may target a nuclease to the insulator or may be bound to a functional domain. The functional domain may allow for demethylation of a CpG. The functional domain may be derived from the Tet gene. Similarly, TALE or zinc finger proteins may be engineered to include functional domains. The functional domains may be nucleases or any function domain described herein. The pharmaceutical composition may comprise more than one agent. The pharmaceutical composition may comprise any combination of agents described herein. The pharmaceutical composition may comprise separate agents. The pharmaceutical composition may be administered sequentially. The agent that alters the topology of a chromatin domain may be administered before an inhibitor of a dehydrogenase. The pharmaceutical composition may comprise an inhibitor of a dehydrogenase and an inhibitor of the oncogene. The altered chromatin topology may be detected by chromosome conformation capture (3C), DNA hypersensitivity, CTCF binding, methylation specific PCR, Ms-SNuPE, bisulfate sequencing, methylation sensitive restriction digest, nanopore sequencing or DNA FISH.

In another aspect, the present invention provides a method of treating a subject in need thereof having cancer or a genetic disorder which predisposes the subject to cancer, said method comprising administering a pharmaceutical composition to the subject, wherein altered chromatin topology within a chromatin region is detected in the subject, wherein said chromatin region comprises at least one distinct topologically-associated domain partitioned by insulator sites, wherein at least one insulator site comprises a CpG dinucleotide within a CTCF binding motif, and wherein the chromatin region comprises an oncogene. The method of treating a subject in need thereof having cancer or a genetic disorder which predisposes the subject to cancer may comprise: detecting altered chromatin topology within a chromatin region, wherein said chromatin region comprises at least one distinct topologically-associated domain partitioned by insulator sites, wherein at least one of said insulator sites comprises a CpG dinucleotide within a CTCF binding motif, and wherein the chromatin region comprises an oncogene; and administering a pharmaceutical composition to the subject if altered chromatin topology is detected. The chromatin region may comprise a regulatory element. The regulatory element may be an enhancer. The detecting altered chromatin topology may comprise detecting 5-methyl cytosine at the CpG dinucleotide. The detecting altered chromatin topology may comprise detecting 5-hydroxymethylcytosine at the CpG dinucleotide. The subject may have a gain of function mutation in the gene encoding isocitrate dehydrogenase (IDH), a loss-of-function mutation in the gene encoding a succinate dehydrogenase, or other genetic mutation that confers DNA hyper-methylation. The subject may have a DNA hypermethylation phenotype. The altered chromatin topology may be detected in a biological sample, wherein said biological sample is blood, sputum, saliva, urine, tumor tissue, lymphatic fluid, semen, feces, biopsy, or circulating tumor cells. The cancer may be a cholangiocarcinoma, leukemia, a chondrosarcoma, a gastrointestinal stromal tumor (GIST), a pheochromocytoma, a paraganglioma, breast cancer, thyroid cancer, colon cancer, melanoma, bladder cancer, ovarian cancer, lung cancer, glioma, kidney cancer, stomach cancer, pancreatic cancer, liver cancer, or neuroblastoma. The genetic disorder may be Ollier Disease, Mafucci syndrome, Carney-Stratakis Syndrome, or a variant of Cowden Syndrome which predisposes to breast and thyroid cancer. The oncogene may be PDGFRA, FGFR2, other RTKs, or other tumorigenic drivers. The pharmaceutical composition may comprise an agent that alters the topology of a chromatin domain. The agent that alters the topology of a chromatin domain may comprise an agent that alters an epigenetic mark within the chromatin domain. In one embodiment, the epigenetic mark is altered within at least one insulator site at the boundary of a topological associated domain. The agent may alter histone acetylation, histone methylation or DNA methylation. The pharmaceutical composition may comprise an inhibitor of the oncogene. The oncogene may be PDGFRA. The inhibitor may be imatinib, crenolanib, or dasatinib. The pharmaceutical composition may comprise an inhibitor of a dehydrogenase. The dehydrogenase may be isocitrate dehydrogenase (IDH). The pharmaceutical composition may comprise an agent that edits the sequence or edits DNA methylation within the insulator site. The agent may be a CRISPR-Cas system, TALE, or Zinc-finger. The pharmaceutical composition may comprise a DNA targeting agent. The agent may comprise a functional domain as described herein. The DNA targeting agent may be a CRISPR-Cas system, TALE, or Zinc-finger. The CRISPR-Cas system may comprise an enzymatically inactive CRISPR enzyme. The enzymatically inactive CRISPR enzyme may be fused to a functional domain. The functional domain may be recruited by a transcript recruitment sequence. The functional domain may be a repressor, activator, DNA modifying enzyme, or histone modifying enzyme. The agent may be inducible, such that the pharmaceutical composition may be active at during a therapeutic window.

The pharmaceutical composition may comprise more than one agent. The pharmaceutical composition may comprise separate agents. The pharmaceutical composition may be administered sequentially. The agent that alters the topology of a chromatin domain may be administered before an inhibitor of a dehydrogenase. The pharmaceutical composition may comprise an inhibitor of a dehydrogenase and an inhibitor of the oncogene. The altered chromatin topology may be detected by chromosome conformation capture (3C), DNA hypersensitivity, CTCF binding, methylation specific PCR, Ms-SNuPE, bisulfate sequencing, methylation sensitive restriction digest, nanopore sequencing or DNA FISH.

Not being bound by a theory, other diseases may be treated that are caused by defects other than having altered chromatin topology. In certain embodiments, removing a boundary may provide a therapeutic effect for a subject with a genetic disease caused by too much or too little gene activity. Removing or disrupting a nearby boundary may offset the defect, regardless of whether the boundary is defective.

The chromatin region of any embodiment described herein may comprise one topologically-associated domain. In certain embodiments, the chromatin region may comprise two, three, four or more topologically-associated domains. In one embodiment, two or more topologically-associated domains may be in the chromatin region, such that one may include an oncogene and the other a regulatory element, whereby altered chromatin topology within a chromatin region may allow interaction between the oncogene and regulatory element. The topologically-associated domains may form a loop. The loop may be anchored at the boundaries of the topologically-associated domain by two convergent insulator sites. The insulator sites may be bound by CTCF and/or CTCF associated proteins or a CTCF associated protein complex. The oncogene may be within a topologically-associated domain or outside of it. The topologically-associated domain may comprise repressive chromatin or heterochromatin, or transcriptionally active chromatin or euchromatin. Disruption of the topologically-associated domain may cause spreading of euchromatin, causing aberrant expression of an oncogene. Disruption of the topologically-associated domain may cause an oncogene present in a repressive chromatin loop to become activated. Disruption of a loop may bring into contact a regulatory element with an oncogene. The regulatory element may be an enhancer.

The altered chromatin topology of any of the methods may comprise a disruption in two or more topologically-associated domains such that the domains have aberrant interactions as compared to chromatin from a normal, non-cancerous subject. At least one chromatin loop within the boundary site that partitions the two or more topologically-associated domains may be disrupted. The altered chromatin topology may be the result of decreased binding of CTCF as compared to a normal, non-cancerous cell. The aberrant interactions between topologically-associated domains may result in altered gene expression. The aberrant interactions may be aberrant enhancer-gene interactions. The topologically-associated domains may be adjacent to each other. The topologically-associated domains having aberrant interactions may be one, two, three, four, five, six, seven, eight, nine, or more than ten domains away.

In another aspect, the present invention provides a method of screening for the onset or predisposition to the onset of cancer in a subject, said method comprising assessing the methylation status of at least one CpG dinucleotide within a CTCF binding motif in a biological sample from said subject, whereby a higher level of methylation of said CTCF binding motif relative to control levels is indicative of cancer or predisposition to the onset of cancer. The method may detect methylation status at one CpG site or any amount of sites within the genome. The methylation status may be assessed at a CTCF binding motif in one or more genomic regions listed in Table S 1. The methylation status may be assessed at sites associated with increased expression of a gene. The methylation status may be assessed at a CTCF binding motif associated with the PDGFRA gene. The methylation status may be assessed at a CTCF binding motif associated with the FGFR2 gene. The methylation status may be assessed by methylation specific PCR, Ms-SNuPE, bisulfite sequencing, methylation sensitive restriction digest, or nanopore sequencing.

In another aspect, the present invention provides a method of screening for the onset or predisposition to the onset of cancer in a subject, said method comprising assessing aberrant chromatin looping in a biological sample from said subject, whereby detection of aberrant chromatin looping is indicative of cancer or predisposition to the onset of cancer. The method may detect aberrant chromatin looping one CTCF binding motif or any amount of sites within the genome. The aberrant chromatin looping may be assessed at a CTCF binding motif in one or more genomic regions listed in Table S 1. The aberrant chromatin looping may be assessed at a CTCF binding motif associated with the PDGFRA gene. The aberrant chromatin looping may be assessed at a CTCF binding motif associated with the FGFR2 gene. The aberrant chromatin looping may be assessed by DNA FISH.

In another aspect, the present invention provides for a method of altering chromatin topology. In one embodiment, CTCF binding to an insulator may be disrupted. Disruption may comprise providing a DNA targeting agent to an insulator element. The DNA targeting agent may be a CRISPR system, zinc finger protein, or TALE. The CRISPR system may comprise a CRISPR enzyme and a guide RNA. The CRISPR enzyme may be enzymatically inactive. Not being bound by a theory, an enzymatically inactive CRISPR enzyme may provide reversible disruption of chromatin topology by disrupting an insulator without editing the target insulator site. The CRISPR enzyme may be inducible or under control of a tissue specific promoter, such that the altered chromatin topology is limited to a specific time period or cell type. The CRISPR enzyme may be fused to a functional domain. The functional domain may be a repressor protein. The repressor protein may be KRAB. The insulator may become enriched for histone H3 lysine 9 tri-methylation (H3K9me3). The CRISPR enzyme may by Cas9. Cas9 may be an enzymatically inactive dCas9.

In alternative embodiments, chromatin topology is altered by recruitment of a DNA targeting agent to an insulator element comprising a CpG dinucleotide within a CTCF binding motif. The DNA targeting agent may include a functional domain. As described herein, the functional domain may include a DNA methyltransferase domain that may be recruited to an insulator to methylate a CpG dinucleotide. In another embodiment, a functional domain may be recruited to remove methylated DNA. The functional domain may be a Tet protein domain as described further herein. Not being bound by a theory, a topologically associated domain may be disrupted by targeting an insulator for DNA methylation and promoted or repaired by targeting an insulator for DNA demethylation.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 12 illustrates clinical specimens and tumor models. Clinical information for glioma specimens and gliomasphere models is shown.

FIG. 13 illustrates the characteristics of sequenced libraries. Pertinent statistics are listed for ChIP, genomic DNA, and bisulfate-converted sequencing libraries.

DETAILED DESCRIPTION OF THE INVENTION

Figure 1:
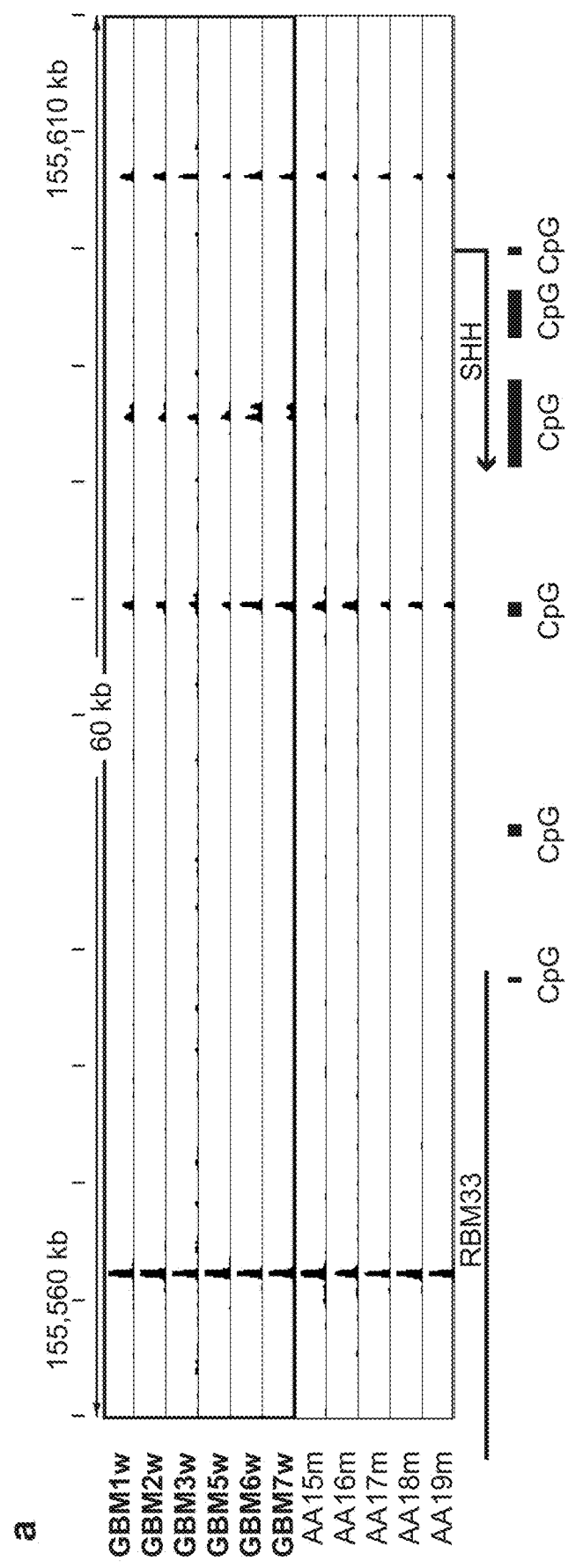
FIG. 1A-1F illustrates that CTCF binding and gene insulation is compromised in IDH mutant gliomas. (a) Binding profiles for the methylation-sensitive insulator CTCF are shown for a representative locus in IDH1 mutant and wildtype tumors, normalized by average signal. (b) Scatterplot compares CTCF binding signals between IDH mutant (y-axis) and IDH1 wildtype gliomas (x-axis) for all detected CTCF sites. A larger fraction of sites is commonly lost in all IDH1 mutants (n=625) than gained (n=300). (c) Histogram compares GC content between CTCF sites that are lost or retained. (d) Box plots show DNA methylation levels over lost CTCF sites, as determined from whole genome bisulfite data for three IDH wildtype and three IDH mutant tumors. (e) Plot depicts average correlation between gene pairs as a function of distance across RNA-seq profiles for human brain[20]. Gene pairs separated by a constitutive CTCF-bound boundary per HiC[15] have lower correlations. (f) Volcano plot depicts the significance (y-axis) of gene pairs that are more (or less) correlated in IDH mutant than IDH wildtype lower-grade gliomas. Gene pairs with significantly increased correlations in IDH mutants (right) tend to cross boundaries (orange), while those with decreased correlations (left) more likely reside in the same domain (blue). These data indicate that IDH mutant G-CIMP gliomas have reduced CTCF binding and altered expression patterns suggestive of defective gene insulation.
Figure 1:
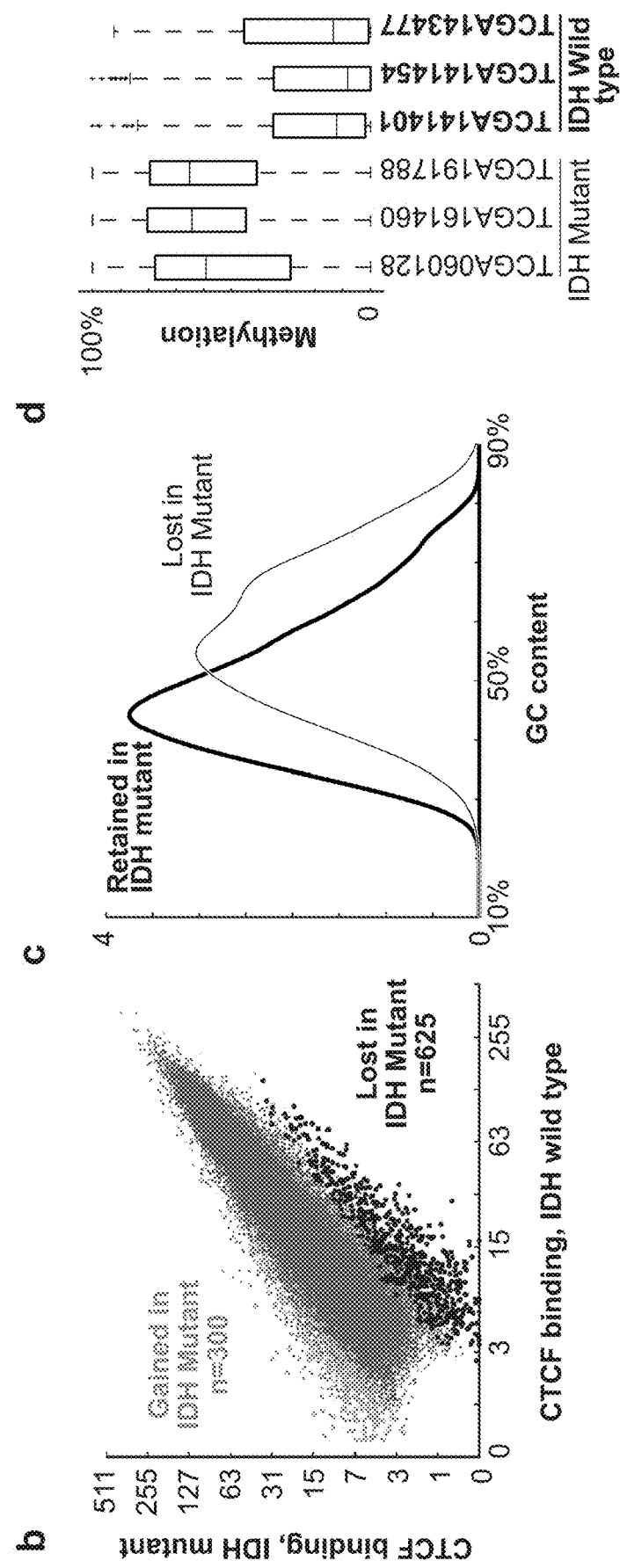
Figure 1:
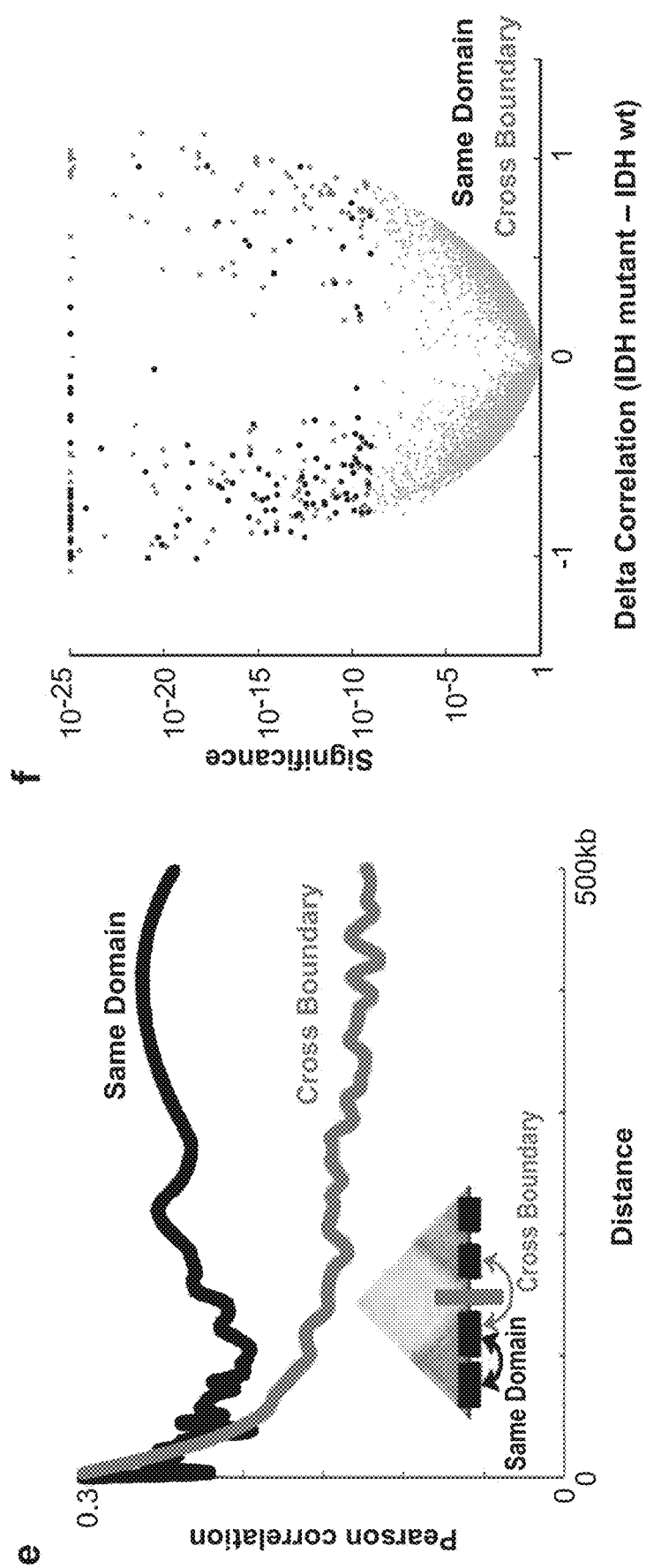

The term "oncogene" refers to any known or unknown gene capable of driving tumorigenesis.

The term "chromatin region" refers to any region of DNA within a genome present in chromatin. Exemplary chromatin regions may be the whole genome, chromosomes, regions of euchromatin, regions of heterochromatin, regions of euchromatin and heterochromatin, or a region with a distinct nuclear localization.

The term "topologically-associated domains" (TAD) refers to regions of the genome that are discrete structural and regulatory units.

The term "altered chromatin topology" refers to a disruption of at least one topologically-associated domain such that the domain may have aberrant interactions. The term "aberrant" refers to a deviation from the normal. In preferred embodiments, chromatin loops and boundaries that partition such domains are disrupted. In an exemplary embodiment, a CTCF-associated boundary is disrupted. The boundary may be disrupted by decreasing binding of CTCF to the boundary. Aberrant interactions may be enhancer-gene interactions between topologically-associated domains resulting in altered gene expression. The topologically-associated domains may be directly adjacent to the boundary region or may be one or more domains away. For example, an oncogene may be aberrantly expressed due to aberrant interaction with a regulatory element, such as an enhancer, two domains away.

The term "insulator" or "insulator site" refers to a genetic boundary element that blocks the interaction between chromatin domains or topologically-associated domains. Insulators partition the genome and are found at the boundaries of topologically-associated domains where they have a role in anchoring loops. The loops are anchored by two convergent CTCF binding motifs recognized by CTCF.

The term "epigenetic state" or "epigenetic mark" may refer to the histone code. An agent that modifies an epigentic mark on chromatin may modify any histone mark for a desired result, such as activation or repression. Exemplary epigenetic marks associated with activation and repression include, but are not limited to:

| Type of modification | Histone | | | | | | | |
|---|---|---|---|---|---|---|---|---|
| | H3K4 | H3K9 | H3K14 | H3K27 | H3K79 | H3K122 | H4K20 | H2BK5 |
| mono-methylation | activation | activation | | activation | activation | | activation | activation |
| di-methylation | activation | repression | | repression | activation | | | |
| tri-methylation | activation | repression | | repression | activation, repression | | | repression |
| acetylation | | activation | activation | activation | | activation | | |

H3K4me3 is enriched in transcriptionally active promoters. H3K9me3 is found in constitutively repressed genes. H3K27me is found in facultatively repressed genes. H3K36me3 is found in actively transcribed gene bodies. H3K9ac is found in actively transcribed promoters. H3K14ac is found in actively transcribed promoters. H3K27ac distinguishes active enhancers from poised enhancers. H3K122ac is enriched in poised promoters and also found in a different type of putative enhancer that lacks H3K27ac.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

By "agent" is meant any small molecule chemical compound, antibody, nucleic acid molecule, or polypeptide, or fragments thereof.

"Combination therapy" is intended to embrace administration of therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. As used herein, the term "simultaneously" is meant to refer to administration of one or more agents at the same time. Simultaneously includes administration contemporaneously, that is during the same period of time. In certain embodiments, the one or more agents are administered simultaneously in the same hour, or simultaneously in the same day. Sequential or substantially simultaneous administration of each therapeutic agent can be effected by any appropriate route including, but not limited to, oral routes, intravenous routes, sub-cutaneous routes, intramuscular routes, direct absorption through mucous membrane tissues (e.g., nasal, mouth, vaginal, and rectal), and ocular routes (e.g., intravitreal, intraocular, etc.). The therapeutic agents can be administered by the same route or by different routes. For example, one component of a particular combination may be administered by intravenous injection while the other component(s) of the combination may be administered orally. The components may be administered in any therapeutically effective sequence. The phrase "combination" embraces groups of compounds or non-drug therapies useful as part of a combination therapy.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, the terms "prevent," "preventing," "prevention," "prophylactic treatment," and the like, refer to reducing the probability of developing a disease or condition in a subject, who does not have, but is at risk of or susceptible to developing a disease or condition.

The terms "treat," "treated," "treating," "treatment," and the like are meant to refer to reducing or ameliorating a disorder and/or symptoms associated therewith (e.g., a neoplasia or tumor). "Treating" may refer to administration of the pharmaceutical composition to a subject after the onset, or suspected onset, of a cancer. "Treating" includes the concepts of "alleviating", which refers to lessening the frequency of occurrence or recurrence, or the severity, of any symptoms or other ill effects related to a cancer and/or the side effects associated with cancer therapy. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "therapeutic effect" refers to some extent of relief of one or more of the symptoms of a disorder (e.g., a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved. An effective amount of the active compound as defined herein may vary according to factors such as the disease state, age, and weight of the subject, and the ability of the active compound to elicit a desired response in the subject and can be determined by the skilled practitioner. Dosage regimens may be adjusted to provide the optimum therapeutic response. An effective amount is also one in which any toxic or detrimental effects of the active compound are outweighed by the therapeutically beneficial effects.

Any compositions or methods provided herein can be combined with one or more of any of the other compositions and methods provided herein.

The present invention provides for methods for treating, preventing, or inhibiting cancer. The present invention further provides for personalized treatment. The personalized methods for diagnosing, screening, and treating are based on the novel discovery that mutations in IDH causes DNA hypermethylation of CpG dinucleotides within CTCF motifs resulting in loss of insulator function, aberrant interactions of topological associated domains, and altered oncogene expression. A subject may be tested for loss of insulator function and/or DNA methylation and/or gene expression. The subject may also be treated with novel pharmaceutical compositions formulated specifically to re-establish normal insulator function, normal gene expression, or normal oncogene activity.

The pharmaceutical compositions may include small molecules, biologics and/or sequence specific targeting molecules. Additionally, the pharmaceutical compositions may include pharmaceutically acceptable salts.

A thorough discussion of pharmaceutically acceptable carriers, diluents, and other excipients is presented in Remington's Pharmaceutical Sciences (17th ed., Mack Publishing Company) and Remington: The Science and Practice of Pharmacy (21st ed., Lippincott Williams & Wilkins), which are hereby incorporated by reference. The formulation of the pharmaceutical composition should suit the mode of administration. In embodiments, the pharmaceutical composition is suitable for administration to humans, and can be sterile, non-particulate and/or non-pyrogenic.

Pharmaceutically acceptable carriers, excipients, or diluents include, but are not limited, to saline, buffered saline, dextrose, water, glycerol, ethanol, sterile isotonic aqueous buffer, and combinations thereof.

The term "pharmaceutically acceptable" refers to approved or approvable by a regulatory agency of the Federal or a state government or listed in the U.S. Pharmacopeia, European Pharmacopia or other generally recognized pharmacopia for use in mammals, and more particularly in humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" as recited herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled tumor specific neoantigens provided herein, including those listed by Remington's Pharmaceutical Sciences, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

Compounds may be provided orally, by intralesional, intraperitoneal, intramuscular or intravenous injection; infusion; liposome-mediated delivery; topical, nasal, anal, vaginal, sublingual, uretheral, transdermal, intrathecal, ocular or otic delivery. In order to obtain consistency in providing the compound of this invention it is preferred that a compound of the invention is in the form of a unit dose.

The compounds of the present invention can be administered orally. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer.

The compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers useful in treatment or prevention of neoplasm. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroblasts. Such compositions will influence the physical state, solubility, stability, rate of in vivo release, and rate of in vivo clearance of the compound or composition. The choice of compositions will depend on the physical and chemical properties of the compound capable of treating or preventing a neoplasm.

The compound of the present invention may be delivered locally via a capsule that allows a sustained release of the compound over a period of time. Controlled or sustained release compositions include formulation in lipophilic depots (for example, fatty acids, waxes, oils).

Imatinib was the first receptor tyrosine kinase (RTK) inhibitor to be introduced into clinical oncology, and was then followed by the drugs sorafenib, dasatinib, sunitinib, nilotinib, pazopanib, and regorafenib. Dosages may be based on the dosages described herein.

Crenolanib besylate (CP-868,596-26; 4-piperidinamine, 1-[2-[5-[(3-Methyl-3-oxetanyl) methoxy]-1H-benzimidazol-1-yl]-8-quinolinyl]-, monobenzenesulfonate) is an investigational inhibitor being developed by AROG Pharmaceuticals, LLC. Crenolanib is an orally bioavailable benzamidazole that selectively and potently inhibits signaling of wild-type and mutant isoforms of class III receptor tyrosine kinases (RTK) FLT3 (FMS-like Tyrosine Kinase 3), PDGFR α (Platelet-Derived Growth Factor Receptor), and PDGFR (3. In clinical trial NCT01522469, subjects take crenolanib in doses of 200 mg/m$^2$/day divided in three doses daily (preferably every eight hours), taken orally at least 30 minutes pre or post meal until disease progression, death, or the patient discontinues treatment for adverse events, investigator's judgment, or other reasons.

In a phase 1 dose-escalation study, 119 patients with imatinib-resistant CIVIL or acute lymphoblastic leukemia (ALL) received nilotinib orally at doses of 50 mg, 100 mg, 200 mg, 400 mg, 600 mg, 800 mg, and 1200 mg once daily and at 400 mg and 600 mg twice daily (Kantarjian, et al. N Engl J Med. 2006 Jun. 15; 354(24):2542-51). Preclinical in vitro studies have shown that nilotinib (AMN107), a BCR-ABL tyrosine kinase inhibitor, is more potent than imatinib against CIVIL cells by a factor of 20 to 50.

Sorafenib (co-developed and co-marketed by Bayer and Onyx Pharmaceuticals as Nexavar), is a kinase inhibitor drug approved for the treatment of primary kidney cancer (advanced renal cell carcinoma), advanced primary liver cancer (hepatocellular carcinoma), and radioactive iodine resistant advanced thyroid carcinoma. Sorafenib is a multi-kinase inhibitor (including VEGF and PDGF receptor kinases), reduces tumor cell proliferation in vitro, and may act at least partially by inhibiting tumor angiogenesis. Dosages may be 400 mg PO q12 hr, or a regimen including: First dose reduction: 600 mg/day (divided as 2 doses of 400 mg and 200 mg 12 hr apart), Second dose reduction: 200 mg q12 hr, Third dose reduction: 200 mg qDay.

Dasatinib is a multikinase inhibitor that inhibits BCR-ABL, SRC family (SRC, LCK, YES, FYN), c-Kit, EPHA2 and PDGFR-beta kinases. Tyrosine kinase inhibition possibly blocks angiogenesis and cellular proliferation. Dosages may be 140 mg PO qDay, but may be increased to 180 mg PO qDay if there is an inadequate response.

Sunitinib is a multikinase inhibitor, including VEGF and PDGF receptor kinases. For GI Stromal Tumor and Metastatic Renal Cell Carcinoma the recommended dose is 50 mg PO qDay for 4 weeks, followed by 2 weeks drug-free, and then repeating the cycle. Dose modification for GI stromal tumor (GIST) or metastic renal cell carcinoma (MRCC) may be an increase or reduction of dose in 12.5-mg increments based on individual safety and tolerability. For Pancreatic Neuroendocrine Tumors the standard dose is 37.5 mg PO qDay continuously without a scheduled off-treatment period. Dose modification for Pancreatic Neuroendocrine Tumors (PNET) may be to increase or reduce the dose in 12.5-mg increments based on individual safety and tolerability.

Pazopanib is a multikinase inhibitor, including VEGF and PDGF receptor kinases. Dosages for advanced Renal Cell Carcinoma are 800 mg PO qDay on an empty stomach (at least 1 hr ac or 2 hr pc). Dosages for Soft Tissue Sarcomas are 800 mg PO qDay on an empty stomach (at least 1 hr ac or 2 hr pc). In RCC, the initial dose reduction should be 400 mg, and an additional dose decrease or increase should be in 200 mg steps based on individual tolerability.

Regorafenib is a tyrosine kinase inhibitor shown to inhibit the activity of membrane-bound and intracellular kinases involved in normal cellular functions and in pathological processes (e.g., oncogenesis, tumor angiogenesis) such as, RET, VEGFR1, VEGFR2, VEGFR3, KIT, PDGFR-alpha, PDGFR-beta, FGFR1, FGFR2, TIE2, DDR2, Trk2A, Eph2A, RAF-1, BRAF, BRAFV600E, SAPK2, PTK5, and Abl. Dosages are 160 mg PO qDay for the first 21 days of each 28-day cycle.

Imatinib mesylate (Gleevec) is a protein tyrosine kinase inhibitor that inhibits the Bcr-Abl tyrosine kinase created by the Philadelphia chromosome abnormality in CIVIL. Imatanib mesylate achieves this inibitory result through binding to the adenosine triphosphate-binding site of the Bcr-Abl tyrosine kinase, which prevents phosphorylation of substrates and related malignant transformation. Through inhibition of this kinase, it is believed that imatib mesylate inhibits cell proliferation and induces apoptosis. T. Schindler et al (2000) Science 289:1938-1942.

According to any of the above methods, in one variation, imatinib mesylate is administered to the subject at a dose of 100-800 mg/day, optionally at a dose of 200-400 mg/day, and optionally at a dose of 500-800 mg/day. Such administrations may optionally last for a period of at least 2, 3, 4, 5, 6, 8, 10 or more days. Preferably, administration is daily. However, upon amelioration of symptoms, it may be useful to administer less frequently unless symptoms re-emerge.

Present dosages recommended for treatment with imatinib mesylate are 400 mg/day for patients with chronic phase CIVIL and 600 mg/day for patients with accelerated phase or blast phase CML. In the event of disease progression, failure to achieve a satisfactory hematologic response after at least 3 months of treatment; or loss of a previously achiever hematologic response, the dose of imatinib mesylate may be increased. Treatment dosage may be increased in patients with chronic phase CIVIL from 400 mg/day to 600 mg/day in the absence of severe adverse drug reaction and sever non-leukemia related neutropenia or thrombocytopenia. Simarlarly, treatment dosage may be increased in patients with chronic phase CIVIL from 600 mg/day to 800 mg/day (Novartis, Gleevec package insert T-2001-14 90012401).

In a further embodiment, the subject is administered between about 200 mg to about 600 mg of imatinib mesylate daily. In one embodiment, the subject is administered either about 600 mg, 400 mg, or 200 mg daily. The skilled artisan will appreciate that certain factors may influence the dosage required to effectively treat a subject, including but not limited to the severity of the symptoms, previous treatments, the general health and/or age of the subject, and other diseases present. Moreover, treatment of a subject with a therapeutically effective amount of the active compound can include a single treatment or a series of treatments. In one example, a subject is treated with an active compound in the range of between about 200-400 mg daily, for between about 1 to 10 weeks, alternatively between 2 to 8 weeks, between about 3 to 7 weeks, or for about 4, 5, or 6 weeks. In some cases, prolonged, indefinite treatment (e.g. for months at a time, 1, 2, 3, 4, etc. 6 months or longer) will be optimal. In some circumstances, the subject should undergo treatment until amelioration of symptoms, with cessation of treatment, and re-initiation of treatment if and when symptoms again manifest. It will also be appreciated that the effective dosage of an active compound used for treatment may increase or decrease over the course of a particular treatment. It may be necessary to adjust dosage when the subject is exposed to drugs that alter imatinib mesylate plasma concentrations, such as inhibitors of cytochrome P450 isoenzyme (CYP3A4) which are expected to increase imatinib mesylate concentrations. Because warfarin is metabolized by CYP2C9 and CYP3A4, patients who require anticoagulation should receive standard heparin or monitor closely PT/INR on warfarin while on imatinib mesylate.

The skilled practitioner will recognize that the dose amounts and frequency of administration can be changed over the course of the regimen, especially as symptoms become alleviated or increase. The regimen can be for weeks or months, continual, intermittent, temporary or permanent, with determination on an individual basis by the skilled practitioner.

Imatinib mesylate is sold under brand name Gleevec®. Gleevec® film-coated tablets contain imatinib mesylate equivalent to 100 mg or 400 mg of imatinib free base. Gleevec® also includes the following inactive ingredients: colloidal silicon dioxide (NF), crospovidone (NF), magnesium stearate (NF) and microcrystalline cellulose (NF). The tablets are coated with ferric oxide, red (NF); ferric oxide, yellow (NF); hydroxyproply methylcellulose (USP); polyethylene glycol (NF) and talc (USP).

Gleevec® is generally prescribed in dosages of 400 mg/day for adult patients in chronic phase CML and 600 mg/day for adult patients in accelerated phase or blast crisis. Additionally, Gleevec® is recommended at dosages of 400 mg/day or 600 mg/day for adult patients with unresectable and/or metastatic, malignant GIST. Gleevec® is generally prescribed to be administered orally, with a meal and a large glass of water, with doses of 400 mg or 600 mg administered once daily, and dosages of 800 mg administered as 400 mg twice a day.

Imatinib has excellent efficacy at low doses (100-400 mg daily) in FIP1L1-PDGFRA-positive neoplasms. Imatinib has a 250-fold lower IC50 as compared to BCR-ABL. Reports suggest that even once weekly doses of imatinib are adequate in the setting of FIP1L1-PDGFRA (Helbig, et al., British Journal of Haematology, 141, 200-204; and Shah et al., Journal of Hematology & Oncology 2014, 7:26). The present invention provides for administering lower doses of Imatinib at intervals of every day to every week to patients with a disrupted insulator at the PDGRFA gene.

Any of these tyrosine kinase inhibitors may be used in treating cancers found to have over-expression of a tyrosine kinase due to disruption of an insulator by DNA hypermethylation within a CTCF binding motif, specifically PDGFRA.

With respect to general information on DNA methylation inhibitors reference is made to Fenaux, Pierre, Inhibitors of DNA methylation: beyond myelodysplastic syndromes. Nature Clinical Practice Oncology (2005) 2, S36-S44, incorporated herein by reference.

DNA methyltransferase (DNMT) inhibitors azacitidine (5-azacytidine) and decitabine (5-aza-2'-deoxycytidine) are the first DNMT inhibitors to be described. These pyrimidine analogs of cytidine incorporate into RNA and DNA, respectively, and form covalent complexes with DNMTs, leading to depletion of active enzymes. Azacitidine also incorporates into RNA, giving rise to defective messenger and transfer RNA, ultimately resulting in inhibition of protein synthesis. Aside from methyltransferase inhibition, these agents are cytotoxic in higher doses, because they directly interfere with DNA synthesis.

Zebularine is another cytidine analog that has a mechanism similar to aza, integrating into DNA and forming a covalent bond with DNMT1. Zebularine is more stable than aza and can be taken orally.

DNA methylation inhibitors may be administered by a variety of routes, including but not limited to orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, or intrathecally.

The DNA methylation inhibitor employed in the present invention may be administered or coadministered in any conventional dosage form. For example, the inhibitor be administered or coadministered parenterally, orally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally.

In a preferred embodiment, the DNA methylation inhibitor is administrated to a patient by injection, including intravenous or subcutaneous injection, such as bolus intravenous injection, continuous intravenous infusion and intravenous infusion over 1 hour. For example, the DNA methylation inhibitor may administered into the patient via an 1-24 hour intravenous infusion per day for 3-5 days per treatment cycle at a dose preferably ranging from 1-100 mg/m$^2$, more preferably ranging from 2-50 mg/m$^2$, and most preferably from 5-20 mg/m$^2$. The preferred dosage below 50 mg/m$^2$ for the DNA methylation inhibitor is considered to be much lower than that used in conventional chemotherapy for cancer.

In another embodiment, the DNA methylation inhibitor is administered via intravenous infusion at a dose ranging from 1 to 100 mg/m$^2$ per day for at least 3 days per treatment cycle. In yet another embodiment, decitabine is administered via intravenous infusion at a dose ranging from 5 to 20 mg/m² for 1 hour per day for 5 consecutive days for 2 weeks per treatment cycle.

The DNA methylation inhibitors employed in the invention may also be administered or coadministered in slow release dosage forms. Furthermore, the DNA methylation inhibitors may be administered or coadministered with conventional pharmaceutical excipients and additives.

The DNA methylation inhibitor may be supplied as sterile powder for injection, together with buffering salt such as potassium dihydrogen and pH modifier such as sodium hydroxide. This formulation is preferably stored at 2-8° C., which should keep the drug stable for at least 2 years. This powder formulation may be reconstituted with 10 ml of sterile water for injection. This solution may be further diluted with infusion fluid known in the art, such as 0.9% sodium chloride injection, 5% dextrose injection and lactated ringer's injection. It is preferred that the reconstituted and diluted solutions be used within 4-6 hours for delivery of maximum potency.

In one variation, the DNA methylation inhibitor is administered to the patient via an intravenous infusion per day at a dose ranging from 1 to 100 mg/m², optionally at a dose ranging from 2 to 50 mg/m², and optionally at a dose ranging from 5 to 20 mg/m². In one particular variation, the DNA methylation inhibitor is administered to the patient via an intravenous infusion per day for at least 3 days per treatment cycle at a dose ranging from 1 to 100 mg/m². In a further example, a DNA methylation inhibitor is administered to the patient via an intravenous infusion at a dose ranging from 5 to 20 mg/m² for 1 hour per day for 5 consecutive days for 2 weeks per treatment cycle.

The present invention allows for lower doses of DNA methylation inhibitor. In one embodiment, the dose is about 0.1 mg/day. In another embodiment, the dose is about 0.15 mg/day. In another embodiment, the dose is about 0.2 mg/day. In another embodiment, the dose is about 0.3 mg/day. In another embodiment, the dose is about 0.5 mg/day. In another embodiment, the dose is about 1 mg/day. In another embodiment, the dose is about 1.5 mg/day. In another embodiment, the dose is about 2 mg/day. In another embodiment, the dose is about 3 mg/day. In another embodiment, the dose is about 5 mg/day. In another embodiment, the dose is about 7 mg/day. In another embodiment, the dose is about 10 mg/day. In another embodiment, the dose is about 15 mg/day. In another embodiment, the dose is about 20 mg/day. In another embodiment, the dose is about 30 mg/day. In another embodiment, the dose is about 50 mg/day. In another embodiment, the dose is about 70 mg/day. In another embodiment, the dose is about 100 mg/day.

In another embodiment, the dose is about 0.1 mg. In another embodiment, the dose is about 0.15 mg. In another embodiment, the dose is about 0.2 mg. In another embodiment, the dose is about 0.3 mg. In another embodiment, the dose is about 0.5 mg. In another embodiment, the dose is about 1 mg. In another embodiment, the dose is about 1.5 mg. In another embodiment, the dose is about 2 mg. In another embodiment, the dose is about 3 mg. In another embodiment, the dose is about 5 mg. In another embodiment, the dose is about 7 mg. In another embodiment, the dose is about 10 mg. In another embodiment, the dose is about 15 mg. In another embodiment, the dose is about 20 mg. In another embodiment, the dose is about 30 mg. In another embodiment, the dose is about 50 mg. In another embodiment, the dose is about 70 mg. In another embodiment, the dose is about 100 mg. The dose administered, the frequency of administration and the duration of the treatment will vary, in another embodiment, as a function of the condition of the patient and is determined according to standard clinical procedures known to the practitioner skilled in the relevant art. Each dose or range thereof represents a separate embodiment of the present invention.

Saiki et al. carried out one of the earliest and largest clinical studies with azacitidine as a single agent for the treatment of leukemia (Saiki J H et al. 1981 Cancer 47: 1739-1742). Five different dosage regimens, ranging from 150 mg/m² for 10 days by continuous intravenous infusion to 750 mg/m² for 1 day by intermittent intravenous infusion, were compared in adult patients with acute leukemia of all cell types who were in relapse. All patients had received prior aggressive chemotherapy.

The overall response rate at the end of the trial was 9.2%, with nine patients achieving complete remission and two achieving partial remission. Lower dose schedules (150 mg/m² times 10 days and 200 mg/m² times 7 days) were associated with higher remission rates. However, the difference in outcomes among the various dose schedules was not statistically significant, perhaps because of the low number of patients assigned to each group.

Shadduck et al. reported on the use of azacitidine in the outpatient setting in 15 adult patients with newly diagnosed AML (Blood 104 (Suppl 1): 499a). Azacitidine was administered at a dose of 75 mg/m² daily subcutaneously for 7 days every 4 weeks as primary induction therapy to patients who ranged in age from 44 to 80 years and with bone marrow blast counts ranging from 20% to 38%. Eight patients experienced either complete or partial remission in an average of three cycles. Duration of response averaged 8 (range, 6-13) and 3 (range, 2-3) cycles in the groups of patients who achieved complete and partial remission, respectively.

As with azacitidine, insight into the potential efficacy of low-dose decitabine in patients with AML is available from experiences reported in high-risk MDS, including RAEBT. In one of the largest studies to correlate cytogenetic status with response to decitabine therapy in patients with MDS, Wijermans et al. reported the highest percentage of responders (14 of 20 patients; 70%) to a 3-day course of decitabine 15 mg/m² daily in the group of patients with RAEBT (J Clin Oncol 18: 956-962).

Lower doses of decitabine were also studied by Issa et al. in a phase I trial involving patients with advanced leukemia or MDS who had failed at least one prior regimen (CML, ALL) or had relapsed after induction (AML, MDS) (Blood 103: 1635-1640). A total of 48 patients received various doses of decitabine ranging from 5 mg/m² daily to 20 mg/m² daily intravenously over 1 h for 10-20 days approximately every 6 weeks.

Overall, objective responses were noted in 16 patients (33%). In 37 patients with AML, 5 (14%) achieved complete response (CR). Three patients (8%) achieved partial response (PR). In seven patients with MDS, two (28.5%) achieved complete response (CR) and two achieved PR. In five patients with CIVIL, two achieved CR and two achieved PR. In eight of nine patients, only one cycle of therapy was required to achieve a CR. Although objective responses were achieved with all doses of decitabine, treatment with higher doses (20 mg/m² for 10 days) and in longer treatment cycles (15 mg/m2 for 20 days) were associated with significantly fewer response rates (45% versus 11%, P=0.01).

Kantarjian et al. carried out a phase II study in which decitabine was administered to 130 patients with CMLs in transformation, 123 of whom had Ph+ CIVIL (64 blastic, 51 accelerated, 8 chronic) (Cancer 98: 522-528). Patients were initially treated with decitabine 100 mg/m$^2$ over 6 h every 12 h for 5 days every 4-8 weeks. The dose was then reduced to 75 mg/m$^2$ over 6 h every 12 h for 5 days after the first 13 patients experienced severe prolonged myelosuppression, and then to 50 mg/m$^2$ in the remaining 84 patients.

The detection of DNA methylation and/or altered chromatin remodeling at insulator sites would allow improved evaluation of the results in each of these trials.

With few exceptions, clinical studies with azacitidine and decitabine demonstrate a greater benefit when these agents are used in lower doses, rather than in their maximum tolerated doses, suggesting that the therapeutic potential of these agents lies largely in their hypomethylating effects, and not in direct inhibition of tumor cells, an effect that becomes more pronounced when higher doses are used. The present invention provides for the first time a mechanism wherein methylation is linked to a common cancer mutation. The discovery allows for the first time a rational treatment regimen that includes a combination of low dose DNA methylation inhibitors with inhibitors of the mutation driving methylation, such as an IDH inhibitor. Additionally, the present invention provides for selecting the best subject candidates for treatment with DNA methylation inhibitors, thus providing improved personalized treatment. Understanding the cause of a subject's cancer also allows for improved monitoring of a subject.

The present invention provides a novel rational dosing strategy for DNA methylation inhibitors. Not being bound by a theory, a subject may be monitored for methylation status of 5-methyl-cytosine at CTCF binding motifs and dosages can be increased or decreased based on the methylation status.

Histone deacetylase inhibitors are the most well studied drugs targeting histone modifying enzymes. Hydroxamic acid inhibitors target Class I and II HDACs and have emerged as promising and potent treatments for cancers. In fact, aminosuberoyl hydroxamic acids, including suberanilohydroxamic acid (SAHA; market name Vorinostat), have been shown to inhibit HDACs and cell proliferation in nanomolar concentrations. In 2006, the US FDA approved Vorinostat as a treatment for progressive, persistent, or recurring cutaneous T-cell lymphoma, or for patients following two systemic chemotherapies (Mann B S, et al., Oncologist. 2007; 12:1247-1252). Previous to the present invention a treatment regimen may include both HDAC inhibitors and DNA methylation inhibitors due to the theory that these treatments result in reactivation of tumor suppressor genes. Not being bound by a theory, based on the present invention, this treatment would not be effective because the use of HDAC inhibitors may result in hyperacetylation of an enhancer in a disrupted topological associated domain and increase enhancer activity. In one embodiment, histone acetylases are inhibited as part of the pharmaceutical composition.

"IDH" refers to an isocitrate dehydrogenase gene. Unless specifically stated otherwise, IDH as used herein, refers to human IDH. There are two isoforms of IDH, IDH1 and IDH2. IDH1 has been assigned accession number NM_005896.2 and IDH2 has been assigned accession number NM_002168.2. Isocitrate dehydrogenase (IDH) 1 and 2 are metabolic enzymes that are mutated in a wide range of hematologic and solid tumor malignancies, including acute myelogenous leukemia (AML) and glioma, a type of aggressive brain tumor with poor prognosis. Agios has identified novel investigational medicines that target the mutated forms of IDH1 and IDH2 (see, www.agios.com/pipeline-idh.php). Reference is also made to Yen, et al., An Inhibitor of Mutant IDH1 Delays Growth and Promotes Differentiation of Glioma Cells. Yen, et al., Science, 2013; and Yen, et al., Targeted Inhibition of Mutant IDH2 in Leukemia Cells Induces Cellular Differentiation. Science, 2013.

AG-221 is an orally available, selective, potent inhibitor of the mutated IDH2 protein, making it a highly targeted investigational medicine for the potential treatment of patients with cancers that harbor an IDH2 mutation. AG-221 has received orphan drug and fast track designations from the U.S. FDA and is currently being evaluated in multiple clinical studies.

AG-120 is a first-in-class, orally available, selective, potent inhibitor of the mutated IDH1 protein, and is a highly targeted investigational medicine for the treatment of patients with cancers that harbor an IDH1 mutation. AG-120 is currently being evaluated in multiple clinical studies.

AG-881 is an orally available inhibitor of the mutated IDH1 and IDH2 proteins. In preclinical studies, it has shown to fully penetrate the blood-brain barrier, which has potential to support ongoing development efforts to provide treatment options to patients with glioma. It also represents a possible second-generation molecule for both AG-221 and AG-120 in IDH mutant tumors. AG-881 is being evaluated in two Phase 1, open-label, dose-escalation and expansion studies, the first in advanced solid tumors and the second in patients with advanced IDH mutant-positive hematologic malignancies whose cancer has progressed on a prior IDH inhibitor therapy. The studies will evaluate the safety, pharmacokinetics, pharmacodynamics and clinical activity of AG-881 in advanced solid tumors and hematologic malignancies.

Not being bound by a theory, the discovery of the impact of DNA methylation within an insulator region allows for more rational and personalized dosage regimens based on determining a dosage that inhibits methylation and/or altered chromatin at these sites in a subject. Furthermore, the combination of DNA methylation inhibitor with that of an inhibitor for IDH allows targeting of more than one cause of the DNA hypermethylation within an insulator. This combination results in a synergistic effect and results in lower toxicity and side effects because of the lower doses of each.

According to the case where the oncogene is a tyrosine kinase and the subject has a mutation in IDH, a pharmaceutical composition comprising an IDH inhibitor, DNA methylation inhibitor and a tyrosine kinase inhibitor may be administered according to any of the methods herein. In other embodiments, the pharmaceutical composition comprises a tyrosine kinase inhibitor and an inhibitor of IDH.

According to any of the methods herein, it is noted that administering an IDH inhibitor and the DNA methylation inhibitor to the patient may comprise administering the IDH inhibitor to the patient for a period of time prior to the administration of the DNA methylation inhibitor, or initiating administration of the DNA methylation inhibitor and the IDH inhibitor to the patient at the same time. It is noted that the method may also comprise administering the IDH inhibitor and the DNA methylation inhibitor to the patient at the same time for at least a portion of the time that the drugs are administered. Not being bound by a theory treating a subject with a DNA methylation inhibitor will allow the demethylation of the CpG site within the CTCF binding motif, thus allowing binding of CTCF and reestablishment of topological associated domains. After the domains are reestablished, treatment with an IDH inhibitor would prevent hypermethylation from reoccurring. Not being bound by a theory, treatment of a subject with an IDH inhibitor after disruption of the insulator has already occurred would not be an effective treatment.

According to any of the methods herein, it is noted that administering imatinib mesylate or any of the tyrosine kinase inhibitors described herein and the DNA methylation inhibitor to the patient may comprise administering imatinib mesylate to the patient for a period of time prior to the administration of the DNA methylation inhibitor, administering the DNA methylation inhibitor to the patient for a period of time prior to the administration of imatinib mesylate, or initiating administration of the DNA methylation inhibitor and imatinib mesylate to the patient at the same time. It is noted that the method may also comprise administering imatinib mesylate and the DNA methylation inhibitor to the patient at the same time for at least a portion of the time that the drugs are administered.

Compositions are also provided. In one embodiment, a composition is provided that comprises a DNA methylation inhibitor and a tyrosine kinase inhibitor. In another variation, the composition is formulated for intravenous, inhalation, oral, or subcutaneous administration. Not being bound by a theory, since any of the tyrosine kinase inhibitor described herein have a strong inhibitory effect on protein tyrosine kinases, a treatment combining the use of a tyrosine kinase inhibitor and DNA methylation inhibitor would have a synergistic effect. Further, lower doses of these two drugs may be used in the combination therapy to reduce side effects associated with an effective monotherapy with either one of these two drugs.

The inventive combination of any of the agents described herein may be administered by a variety of routes, and may be administered or coadministered in any conventional dosage form. Coadministration in the context of this invention is defined to mean the administration of more than one therapeutic in the course of a coordinated treatment to achieve an improved clinical outcome. Such coadministration may also be coextensive, that is, occurring during overlapping periods of time. For example, the DNA methylation inhibitor may be administered to a patient before, concomitantly, or after imatinib mesylate is administered. In one variation, the patient is treated first with imatinib mesylate and then treated with the DNA methylation inhibitor (e.g., decitabine).

Additionally, in some embodiments a DNA targeting molecule is used in combination within the pharmaceutical composition. As described herein, the DNA targeting molecule may be a CRISPR-Cas system, zinc finger, or TALE. The DNA targeting molecules may target a nuclease to the CTCF motif to remove or edit the CpG site. Additionally, as described herein, the DNA targeting molecule may include a functional domain. The functional domain may be configured to demethylate the CpG site within a specific CTCF motif. DNA demethylation may comprise any methods described in Xu et al., "A CRISPR-based approach for targeted DNA demethylation," (Cell Discovery 2, Article number: 16009 (2016) doi:10.1038/celldisc.2016.9). In certain embodiments, the Tet1 catalytic domain is targeted to an insulator. The functional domain may also include a DNA methyltransferase to methylate a CpG dinucleotide within an insulator. DNA methylation may comprise any methods described in McDonald, et al., (2016). "Reprogrammable CRISPR/Cas9-based system for inducing site-specific DNA methylation" Biology Open bio.019067. doi: 10.1242/bio.019067). In one embodiment, targeted DNA methylation may be performed with a CRISPR/Cas9 DNA methyltransferase 3A (DNMT3A) fusion. The functional domain may also modify the epigenetic state of an insulator by modifying histone post translational modifications described herein. Functional domains may add a repressive or active histone mark as described herein. DNA targeting molecules may also target an oncogene. Functional domains may be recruited to a target insulator by a fusion protein of DNA targeting molecule and the functional domain.

In certain embodiments, a CRISPR guide RNA is configured to recruit the functional domain by introduction of a transcript recruitment sequence that forms a loop secondary structure and binds to an adapter protein. In an aspect the invention provides for introduction of an RNA sequence into a transcript recruitment sequence that forms a loop secondary structure and binds to an adapter protein. In an aspect the invention provides a herein-discussed composition, wherein the insertion of distinct RNA sequence(s) that bind to one or more adaptor proteins is an aptamer sequence. In an aspect the invention provides a herein-discussed composition, wherein the aptamer sequence is two or more aptamer sequences specific to the same adaptor protein. In an aspect the invention provides a herein-discussed composition, wherein the aptamer sequence is two or more aptamer sequences specific to a different adaptor protein. In an aspect the invention provides a herein-discussed composition, wherein the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In an aspect the invention provides a herein-discussed composition, wherein the cell is a eukaryotic cell. In an aspect the invention provides a herein-discussed composition, wherein the eukaryotic cell is a mammalian cell, optionally a mouse cell. In an aspect the invention provides a herein-discussed composition, wherein the mammalian cell is a human cell. Aspects of the invention encompass embodiments relating to MS2 adaptor proteins described in Konermann et al. "Genome-scale transcriptional activation by an engineered CRISPR-Cas9 complex" Nature. 2014 Dec. 10. doi: 10.1038/nature14136, the contents of which are herein incorporated by reference in its entirety.

In some embodiments, the adaptor protein domain is an RNA-binding protein domain. The RNA-binding protein domain recognises corresponding distinct RNA sequences, which may be aptamers. For example, the MS2 RNA-binding protein recognises and binds specifically to the MS2 aptamer (or vice versa).

Similarly, an MS2 variant adaptor domain may also be used, such as the N55 mutant, especially the N55K mutant. This is the N55K mutant of the MS2 bacteriophage coat protein (shown to have higher binding affinity than wild type MS2 in Lim, F., M. Spingola, and D. S. Peabody. "Altering the RNA binding specificity of a translational repressor." Journal of Biological Chemistry 269.12 (1994): 9006-9010).

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213, 991), US 2014-0273234 A1 (U.S. application Ser. No. 14/293,674), US2014-0273232 A1 (U.S. application Ser. No. 14/290,575), US 2014-0273231 (U.S. application Ser.

No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15,2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546): 186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

Zetsche et al., "Cpf1 Is a Single RNA-Guided Endonuclease of a Class 2 CRISPR-Cas System," Cell 163, 1-13 (Oct. 22, 2015)

Shmakov et al., "Discovery and Functional Characterization of Diverse Class 2 CRISPR-Cas Systems," Molecular Cell 60, 1-13 (Available online Oct. 22, 2015)

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30C, e.g., 20-25C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention).

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In a classic CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA (s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA (s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example S. pyogenes Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

The nucleic acid molecule encoding a Cas is advantageously codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way how the Cas transgene is introduced in the cell is may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al. (2009).

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 9); the NLS from nucleoplasmin (e.g. the nucleoplasmin bipartite NLS with the sequence KRPAATKKAGQAKKKK) (SEQ ID NO: 10); the c-myc NLS having the amino acid sequence PAAKRVKLD (SEQ ID NO: 11) or RQRRNELKRSP (SEQ ID NO: 12)]; the hRNPA1 M9 NLS having the sequence NQSSNFGPMKGGNFGGRSSGPYGGGGQYFAK-PRNQGGY (SEQ ID NO: 13); the sequence RMRIZFKNKGKDTAELRRRRVEVSVELRKAKKD-EQILKRRNV (SEQ ID NO: 14) of the IBB domain from importin-alpha; the sequences VSRKRPRP (SEQ ID NO: 15) and PPKKARED (SEQ ID NO: 16) of the myoma T protein; the sequence POPKKKPL (SEQ ID NO: 17) of human p53; the sequence SALIKKKKKMAP (SEQ ID NO: 18) of mouse c-abl IV; the sequences DRLRR (SEQ ID NO: 19) and PKQKKRK (SEQ ID NO: 20) of the influenza virus NS1; the sequence RKLKKKIKKL (SEQ ID NO: 21) of the Hepatitis virus delta antigen; the sequence REKKKFLKRR (SEQ ID NO: 22) of the mouse Mx1 protein; the sequence KRKGDEVDGVDEVAKKKSKK (SEQ ID NO: 23) of the human poly(ADP-ribose) polymerase; and the sequence RKCLQAGMNLEARKTKK (SEQ ID NO: 24) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

In certain aspects the invention involves vectors, e.g. for delivering or introducing in a cell the DNA targeting agent according to the invention as described herein, such as by means of example Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly www.genome-engineering.org/taleffectors/. The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html. In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters-especially as to the numbers of RNAs or guides or sgRNAs discussed herein, without any undue experimentation.

A poly nucleic acid sequence encoding the DNA targeting agent according to the invention as described herein, such as by means of example guide RNA(s), e.g., sgRNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Through this disclosure and the knowledge in the art, the DNA targeting agent as described herein, such as, TALEs, CRISPR-Cas systems, etc., or components thereof or nucleic acid molecules thereof (including, for instance HDR template) or nucleic acid molecules encoding or providing components thereof may be delivered by a delivery system herein described both generally and in detail.

Vector delivery, e.g., plasmid, viral delivery: By means of example, the CRISPR enzyme, for instance a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. The DNA targeting agent as described herein, such as Cas9 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^0$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg per 70 kg individual. Plasmids of the invention will generally comprise (i) a promoter; (ii) a sequence encoding a DNA targeting agent as described herein, such as a comprising a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver the DNA targeting agent as described herein, such as Cas9 and gRNA (and, for instance, HR repair template) into cells using liposomes or particles. Thus delivery of the CRISPR enzyme, such as a Cas9 and/or delivery of the RNAs of the invention may be in RNA form and via microvesicles, liposomes or particles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 μmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of $1\times10^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1\times10^9$ transducing units (TU)/ml may be contemplated.

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters Generally

Ways to package nucleic acid molecules, in particular the DNA targeting agent according to the invention as described herein, such as Cas9 coding nucleic acid molecules, e.g., DNA, into vectors, e.g., viral vectors, to mediate genome modification in vivo include:

To achieve NHEJ-mediated gene knockout:
Single virus vector:
Vector containing two or more expression cassettes:
Promoter-Cas9 coding nucleic acid molecule-terminator
Promoter-gRNA1-terminator
Promoter-gRNA2-terminator Promoter-gRNA(N)-terminator (up to size limit of vector)

Double virus vector:
Vector 1 containing one expression cassette for driving the expression of Cas9
Promoter-Cas9 coding nucleic acid molecule-terminator
Vector 2 containing one more expression cassettes for driving the expression of one or more guideRNAs
Promoter-gRNA1-terminator
Promoter-gRNA(N)-terminator (up to size limit of vector)
To mediate homology-directed repair.

In addition to the single and double virus vector approaches described above, an additional vector is used to deliver a homology-direct repair template.

The promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas9.

For ubiquitous expression, can use promoters: CMV, CAG, CBh, PGK, SV40, Ferritin heavy or light chains, etc.

For brain or other CNS expression, can use promoters: SynapsinI for all neurons, CaMKIIalpha for excitatory neurons, GAD67 or GAD65 or VGAT for GABAergic neurons, etc.

For liver expression, can use Albumin promoter.
For lung expression, can use SP-B.
For endothelial cells, can use ICAM.
For hematopoietic cells can use IFNbeta or CD45.
For Osteoblasts can use OG-2.
The promoter used to drive guide RNA can include:
Pol III promoters such as U6 or H1
Use of Pol II promoter and intronic cassettes to express gRNA Adeno Associated Virus (AAV)

The DNA targeting agent according to the invention as described herein, such as by means of example Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of the DNA targeting agent according to the invention as described herein, such as by means of example Cas9 can be driven by a cell-type specific promoter. For example, liver-specific expression might use the Albumin promoter and neuron-specific expression (e.g. for targeting CNS disorders) might use the Synapsin I promoter.

In terms of in vivo delivery, AAV is advantageous over other viral vectors for a couple of reasons:

Low toxicity (this may be due to the purification method not requiring ultra centrifugation of cell particles that can activate the immune response)

Low probability of causing insertional mutagenesis because it doesn't integrate into the host genome.

AAV has a packaging limit of 4.5 or 4.75 Kb. This means that for instance Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Species | Cas9 Size |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows, by means of example for Cas delivery. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50ul of DMEM overnight at 4C. They were then aliquotted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention.

A minimum of $2.5 \times 10^6$ CD34+ cells per kilogram patient weight may be collected and prestimulated for 16 to 20 hours in X-VIVO 15 medium (Lonza) containing 2 μmon-glutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-cm$^2$ tissue culture flasks coated with fibronectin (25 mg/cm$^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The DNA targeting agent according to the invention as described herein, such as the CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7 promoter-GG-guide RNA sequence. To enhance expression and reduce possible toxicity, the CRISPR enzyme-coding sequence and/or the guide RNA can be modified to include one or more modified nucleoside e.g. using pseudo-U or 5-Methyl-C. mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of for instance CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Particles

The DNA targeting agent according to the invention as described herein, such as by means of example CRISPR enzyme mRNA and guide RNA may be delivered simultaneously using particles or lipid envelopes; for instance, CRISPR enzyme and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1×PBS; and separately, DOTAP, DMPC, PEG, and cholesterol as applicable for the formulation are dissolved in alcohol, e.g., 100% ethanol; and, the two solutions are mixed together to form particles containing the complexes).

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured particles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, particles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles that can deliver DNA targeting agents according to the invention as described herein, such as RNA to a cancer cell to stop tumor growth developed by Dan Anderson's lab at MIT may be used/and or adapted to the CRISPR Cas system according to certain embodiments of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32): 12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the DNA targeting agent according to the invention, such as for instance the CRISPR Cas system according to certain embodiments of the present invention. In one aspect, the aminoalcohol lipidoid compounds are combined with an agent to be delivered to a cell or a subject to form microparticles, particles, liposomes, or micelles. The agent to be delivered by the particles, liposomes, or micelles may be in the form of a gas, liquid, or solid, and the agent may be a polynucleotide, protein, peptide, or small molecule. The minoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the DNA targeting agent according to the invention, such as for instance the CRISPR Cas system according to certain embodiments of the present invention.

In another embodiment, lipid particles (LNPs) are contemplated. An antitransthyretin small interfering RNA has been encapsulated in lipid particles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethyl-ammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 µg/ml of LNP or by means of example CRISPR-Cas RNA in or associated with the LNP may be contemplated, especially for a formulation containing DLinKC2-DMA.

Preparation of LNPs and the DNA targeting agent according to the invention as described herein, such as by means of example CRISPR Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethyl-aminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(w-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR Cas RNA may be encapsulated in LNPs containing DLinDAP, DLinDMA, DLinK-DMA, and DLinKC2-DMA (cationic lipid:DSPC: CHOL:PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/1 citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Particle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted particles and quantified at 260 nm. RNA to lipid ratio was determined by measurement of cholesterol content in vesicles using the Cholesterol E enzymatic assay from Wako Chemicals USA (Richmond, Va.). In conjunction with the herein discussion of LNPs and PEG lipids, PEGylated liposomes or LNPs are likewise suitable for delivery of a CRISPR-Cas system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/1, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Spherical Nucleic Acid (SNA™) constructs and other particles (particularly gold particles) are also contemplated as a means to deliver the DNA targeting agent according to the invention as described herein, such as by means of example CRISPR-Cas system to intended targets. Significant data show that AuraSense Therapeutics' Spherical Nucleic Acid (SNA™) constructs, based upon nucleic acid-functionalized gold particles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J.

Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling particles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling particles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclodo-decane-1,4,7,10-tetraacetic acid mono(N-hydroxysuccinimide ester) (DOTA-NHSester) was ordered from Macrocyclics (Dallas, Tex.). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, Calif.) to remove trace metal contaminants. Tf-targeted and nontargeted siRNA particles may be formed by using cyclodextrin-containing polycations. Typically, particles were formed in water at a charge ratio of 3 (+/−) and an siRNA concentration of 0.5 g/liter. One percent of the adamantane-PEG molecules on the surface of the targeted particles were modified with Tf (adamantane-PEG-Tf). The particles were suspended in a 5% (wt/vol) glucose carrier solution for injection.

Davis et al. (Nature, Vol 464, 15 Apr. 2010) conducts a RNA clinical trial that uses a targeted particle-delivery system (clinical trial registration number NCT00689065). Patients with solid cancers refractory to standard-of-care therapies are administered doses of targeted particles on days 1, 3, 8 and 10 of a 21-day cycle by a 30-min intravenous infusion. The particles consist of a synthetic delivery system containing: (1) a linear, cyclodextrin-based polymer (CDP), (2) a human transferrin protein (TF) targeting ligand displayed on the exterior of the particle to engage TF receptors (TFR) on the surface of the cancer cells, (3) a hydrophilic polymer (polyethylene glycol (PEG) used to promote particle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These particles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m' siRNA, respectively. Similar doses may also be contemplated for the CRISPR Cas system of the present invention. The delivery of the invention may be achieved with particles containing a linear, cyclodextrin-based polymer (CDP), a human transferrin protein (TF) targeting ligand displayed on the exterior of the particle to engage TF receptors (TFR) on the surface of the cancer cells and/or a hydrophilic polymer (for example, polyethylene glycol (PEG) used to promote particle stability in biological fluids).

In terms of this invention, it is preferred to have one or more components of the DNA targeting agent according to the invention as described herein, such as by means of example the CRISPR complex, e.g., CRISPR enzyme or mRNA or guide RNA delivered using particles or lipid envelopes. Other delivery systems or vectors are may be used in conjunction with the particle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, particles of the invention have a greatest dimension ranging between 35 nm and 60 nm. In other preferred embodiments, the particles of the invention are not nanoparticles.

Particles encompassed in the present invention may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles). Particles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft particles have been manufactured, and are within the scope of the present invention. A prototype particle of semi-solid nature is the liposome. Various types of liposome particles are currently used clinically as delivery systems for anticancer drugs and vaccines. Particles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising comprising polymer conjugated to a surfactant, hydrophilic polymer or lipid. U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material. U.S. Pat. No. 5,855,913, incorporated herein by reference, provides a particulate composition having aerodynamically light particles having a tap density of less than 0.4 g/cm3 with a mean diameter of between 5 µm and 30 µm, incorporating a surfactant on the surface thereof for drug delivery to the pulmonary system. U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system. U.S. Pat. No. 5,543,158, incorporated herein by reference, provides biodegradable injectable particles having a biodegradable solid core containing a biologically active material and poly(alkylene glycol) moieties on the surface. WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the CRISPR-Cas system to achieve in vitro, ex vivo and in vivo genomic perturbations to modify gene expression, including modulation of protein expression.

In one embodiment, the particle may be epoxide-modified lipid-polymer, advantageously 7C1 (see, e.g., James E. Dahlman and Carmen Barnes et al. Nature Nanotechnology (2014) published online 11 May 2014, doi:10.1038/nnano.2014.84). C71 was synthesized by reacting C15 epoxide-terminated lipids with PEI600 at a 14:1 molar ratio, and was formulated with C14PEG2000 to produce particles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by particle tracking analysis (NTA) and electron microscopy. Alvarez-Erviti et al. obtained 6-12 µg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 µF resulted in the greatest retention of RNA and was used for all subsequent experiments.

Alvarez-Erviti et al. administered 150 µg of each BACE1 siRNA encapsulated in 150 of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the DNA targeting agent according to the invention as described herein, such as by means of example the CRISPR-Cas system of the present invention to therapeutic targets, especially neurodegenerative diseases. A dosage of about 100 to 1000 mg of CRISPR Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing the DNA targeting agent according to the invention as described herein, such as by means of example CRISPR Cas may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the DNA targeting agent according to the invention as described herein, such as by means of example the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the DNA targeting agent according to the invention as described herein, such as by means of example the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1, 2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N; N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at >0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Niotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-

DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate the DNA targeting agent according to the invention as described herein, such as by means of example CRISPR Cas or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11+0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the CRISPR Cas system of the present invention to form lipid particles (LNPs). Lipids include, but are not limited to, DLin-KC2-DMA4, C12-200 and colipids disteroylphosphatidyl choline, cholesterol, and PEG-DMG may be formulated with CRISPR Cas instead of siRNA (see, e.g., Novobrantseva, Molecular Therapy—Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid particles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The DNA targeting agent according to the invention as described herein, such as by means of example CRISPR Cas system or components thereof or nucleic acid molecule(s) coding therefore may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid: fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of the DNA targeting agent according to the invention as described herein, such as by means of example CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified +36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116) (However, pilot experiments varying the dose of protein and RNA should be performed to optimize the procedure for specific cell lines): (1) One day before treatment, plate $1 \times 10^5$ cells per well in a 48-well plate. (2) On the day of treatment, dilute purified +36 GFP protein in serumfree media to a final concentration 200 nM. Add RNA to a final concentration of 50 nM. Vortex to mix and incubate at room temperature for 10 min. (3) During incubation, aspirate media from cells and wash once with PBS. (4) Following incubation of +36 GFP and RNA, add the protein-RNA complexes to cells. (5) Incubate cells with complexes at 37° C. for 4h. (6) Following incubation, aspirate the media and wash three times with 20 U/mL heparin PBS. Incubate cells with serum-containing media for a further 48h or longer depending upon the assay for activity. (7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications: (1) One day before treatment, plate $1 \times 10^5$ per well in a 48-well plate. (2) On the day of treatment, dilute purified þ36 GFP protein in serumfree media to a final concentration 2 mM. Add 1 mg of plasmid DNA. Vortex to mix and incubate at room temperature for 10 min. (3) During incubation, aspirate media from cells and wash once with PBS. (4) Following incubation of þ36 GFP and plasmid DNA, gently add the protein-DNA complexes to cells. (5) Incubate cells with complexes at 37 C for 4h. (6) Following incubation, aspirate the media and wash with PBS. Incubate cells in serum-containing media and incubate for a further 24-48h. (7) Analyze plasmid delivery (e.g., by plasmid-driven gene expression) as appropriate. See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention. These systems of Dr. Lui and documents herein in inconjunction with herein teachints can be employed in the delivery of the DNA targeting agent according to the invention as described herein, such as by means of example CRISPR Cas system(s) or component(s) thereof or nucleic acid molecule(s) coding therefor.

Cell Penetrating Peptides (CPPs)

In yet another embodiment, cell penetrating peptides (CPPs) are contemplated for the delivery of the DNA targeting agent according to the invention as described herein, such as by means of example CRISPR Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles, liposomes, chromophores, small molecules and radioactive materials. In aspects of the invention, the cargo may also comprise any component of the DNA targeting agent according to the invention as described herein, such as by means of example CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl) SEQ ID NO: 65.

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the CRISPR-Cas system or components thereof. That CPPs can be employed to deliver the CRISPR-Cas system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Implantable Devices

In another embodiment, implantable devices are also contemplated for delivery of the the DNA targeting agent according to the invention as described herein, such as by means of example the CRISPR Cas system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the the DNA targeting agent according to the invention as described herein, such as by means of example CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m$^3$ to 1000 mm$^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear—auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR Cas system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the DNA targeting agent according to the invention as described herein, such as by means of example CRISPR Cas system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the DNA targeting agent according to the invention as described herein, such as by means of example CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable device technology herein discussed can be employed with herein teachings and hence by this disclosure and the knowledge in the art, the DNA targeting agent according to the invention as described herein, such as by means of example CRISPR-Cas system or components thereof or nucleic acid molecules thereof or encoding or providing components may be delivered via an implantable device.

The present application also contemplates an inducible CRISPR Cas system. Reference is made to international patent application Serial No. PCT/US13/51418 filed Jul. 21, 2013, which published as WO2014/018423 on Jan. 30, 2014.

In one aspect the invention provides a DNA targeting agent according to the invention as described herein, such as by means of example a non-naturally occurring or engineered CRISPR Cas system which may comprise at least one switch wherein the activity of said CRISPR Cas system is controlled by contact with at least one inducer energy source as to the switch. In an embodiment of the invention the control as to the at least one switch or the activity of said CRISPR Cas system may be activated, enhanced, terminated or repressed. The contact with the at least one inducer energy source may result in a first effect and a second effect.

The first effect may be one or more of nuclear import, nuclear export, recruitment of a secondary component (such as an effector molecule), conformational change (of protein, DNA or RNA), cleavage, release of cargo (such as a caged molecule or a co-factor), association or dissociation. The second effect may be one or more of activation, enhancement, termination or repression of the control as to the at least one switch or the activity of said the DNA targeting agent according to the invention as described herein, such as by means of example CRISPR Cas system. In one embodiment the first effect and the second effect may occur in a cascade.

The invention comprehends that the inducer energy source may be heat, ultrasound, electromagnetic energy or chemical. In a preferred embodiment of the invention, the inducer energy source may be an antibiotic, a small molecule, a hormone, a hormone derivative, a steroid or a steroid derivative. In a more preferred embodiment, the inducer energy source maybe abscisic acid (ABA), doxycycline (DOX), cumate, rapamycin, 4-hydroxytamoxifen (4OHT), estrogen or ecdysone.

The invention provides that the at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4OHT/estrogen inducible systems, ecdysone-based inducible systems and FKBP12/FRAP (FKBP12-rapamycin complex) inducible systems.

In one aspect of the invention the inducer energy source is electromagnetic energy.

The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 mW/cm2, or more preferably at least 4 mW/cm2. In another embodiment, the component of visible light may have a wavelength in the range of 620-700 nm and is red light.

In a further aspect, the invention provides a method of controlling a the DNA targeting agent according to the invention as described herein, such as by means of example a non-naturally occurring or engineered CRISPR Cas system, comprising providing said CRISPR Cas system comprising at least one switch wherein the activity of said CRISPR Cas system is controlled by contact with at least one inducer energy source as to the switch.

In an embodiment of the invention, the invention provides methods wherein the control as to the at least one switch or the activity of said the DNA targeting agent according to the invention as described herein, such as by means of example CRISPR Cas system may be activated, enhanced, terminated or repressed. The contact with the at least one inducer energy source may result in a first effect and a second effect. The first effect may be one or more of nuclear import, nuclear export, recruitment of a secondary component (such as an effector molecule), conformational change (of protein, DNA or RNA), cleavage, release of cargo (such as a caged molecule or a co-factor), association or dissociation. The second effect may be one or more of activation, enhancement, termination or repression of the control as to the at least one switch or the activity of said CRISPR Cas system. In one embodiment the first effect and the second effect may occur in a cascade.

The invention comprehends that the inducer energy source may be heat, ultrasound, electromagnetic energy or chemical. In a preferred embodiment of the invention, the inducer energy source may be an antibiotic, a small molecule, a hormone, a hormone derivative, a steroid or a steroid derivative. In a more preferred embodiment, the inducer energy source maybe abscisic acid (ABA), doxycycline (DOX), cumate, rapamycin, 4-hydroxytamoxifen (4OHT), estrogen or ecdysone. The invention provides that the at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4OHT/estrogen inducible systems, ecdysone-based inducible systems and FKBP12/FRAP (FKBP12-rapamycin complex) inducible systems.

In one aspect of the methods of the invention the inducer energy source is electromagnetic energy. The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 mW/cm2, or more preferably at least 4 mW/cm2. In another embodiment, the component of visible light may have a wavelength in the range of 620-700 nm and is red light.

In another preferred embodiment of the invention, the inducible effector may be a Light Inducible Transcriptional Effector (LITE). The modularity of the LITE system allows for any number of effector domains to be employed for transcriptional modulation. In yet another preferred embodiment of the invention, the inducible effector may be a chemical. The invention also contemplates an inducible multiplex genome engineering using CRISPR (clustered regularly interspaced short palindromic repeats)/Cas systems.

With respect to use of the CRISPR-Cas system generally, mention is made of the documents, including patent applications, patents, and patent publications cited throughout this disclosure as embodiments of the invention can be used as in those documents. CRISPR-Cas System(s) can be used to perform efficient and cost effective functional genomic screens. Such screens can utilize CRISPR-Cas genome wide libraries. Such screens and libraries can provide for determining the function of genes, cellular pathways genes are involved in, and how any alteration in gene expression can result in a particular biological process. An advantage of the present invention is that the CRISPR system avoids off-target binding and its resulting side effects. This is achieved using systems arranged to have a high degree of sequence specificity for the target DNA.

A genome wide library may comprise a plurality of CRISPR-Cas system guide RNAs, as described herein, comprising guide sequences that are capable of targeting a plurality of target sequences in a plurality of genomic loci in a population of eukaryotic cells. The population of cells may be a population of embryonic stem (ES) cells. The target sequence in the genomic locus may be a non-coding sequence. The non-coding sequence may be an intron, regulatory sequence, splice site, 3' UTR, 5' UTR, or polyadenylation signal. Gene function of one or more gene products may be altered by said targeting. The targeting may result in a knockout of gene function. The targeting of a gene product may comprise more than one guide RNA. A gene product may be targeted by 2, 3, 4, 5, 6, 7, 8, 9, or 10 guide RNAs, preferably 3 to 4 per gene. Off-target modifications may be minimized (See, e.g., DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013)), incorporated herein by reference. The targeting may be of about 100 or more sequences. The targeting may be of about 1000 or more sequences. The targeting may be of about 20,000 or more sequences. The targeting may be of the entire genome. The targeting may be of a panel of target sequences focused on a relevant or desirable pathway. The pathway may be an immune pathway. The pathway may be a cell division pathway.

One aspect of the invention comprehends a genome wide library that may comprise a plurality of CRISPR-Cas system guide RNAs that may comprise guide sequences that are capable of targeting a plurality of target sequences in a plurality of genomic loci, wherein said targeting results in a knockout of gene function. This library may potentially comprise guide RNAs that target each and every gene in the genome of an organism.

In some embodiments of the invention the organism or subject is a eukaryote (including mammal including human) or a non-human eukaryote or a non-human animal or a non-human mammal. In some embodiments, the organism or subject is a non-human animal, and may be an arthropod, for example, an insect, or may be a nematode. In some methods of the invention the organism or subject is a plant. In some methods of the invention the organism or subject is a mammal or a non-human mammal. A non-human mammal may be for example a rodent (preferably a mouse or a rat), an ungulate, or a primate. In some methods of the invention the organism or subject is algae, including microalgae, or is a fungus.

The knockout of gene function may comprise: introducing into each cell in the population of cells a vector system of one or more vectors comprising an engineered, non-naturally occurring CRISPR-Cas system comprising I. a Cas protein, and II. one or more guide RNAs, wherein components I and II may be same or on different vectors of the system, integrating components I and II into each cell, wherein the guide sequence targets a unique gene in each cell, wherein the Cas protein is operably linked to a regulatory element, wherein when transcribed, the guide RNA comprising the guide sequence directs sequence-specific binding of a CRISPR-Cas system to a target sequence in the genomic loci of the unique gene, inducing cleavage of the genomic loci by the Cas protein, and confirming different knockout mutations in a plurality of unique genes in each cell of the population of cells thereby generating a gene knockout cell library. The invention comprehends that the population of cells is a population of eukaryotic cells, and in a preferred embodiment, the population of cells is a population of embryonic stem (ES) cells.

The one or more vectors may be plasmid vectors. The vector may be a single vector comprising Cas9, a sgRNA, and optionally, a selection marker into target cells. Not being bound by a theory, the ability to simultaneously deliver Cas9 and sgRNA through a single vector enables application to any cell type of interest, without the need to first generate cell lines that express Cas9. The regulatory element may be an inducible promoter. The inducible promoter may be a doxycycline inducible promoter. In some methods of the invention the expression of the guide sequence is under the control of the T7 promoter and is driven by the expression of T7 polymerase. The confirming of different knockout mutations may be by whole exome sequencing. The knockout mutation may be achieved in 100 or more unique genes. The knockout mutation may be achieved in 1000 or more unique genes. The knockout mutation may be achieved in 20,000 or more unique genes. The knockout mutation may be achieved in the entire genome. The knockout of gene function may be achieved in a plurality of unique genes which function in a particular physiological pathway or condition. The pathway or condition may be an immune pathway or condition. The pathway or condition may be a cell division pathway or condition.

The invention also provides kits that comprise the genome wide libraries mentioned herein. The kit may comprise a single container comprising vectors or plasmids comprising the library of the invention. The kit may also comprise a panel comprising a selection of unique CRISPR-Cas system guide RNAs comprising guide sequences from the library of the invention, wherein the selection is indicative of a particular physiological condition. The invention comprehends that the targeting is of about 100 or more sequences, about 1000 or more sequences or about 20,000 or more sequences or the entire genome. Furthermore, a panel of target sequences may be focused on a relevant or desirable pathway, such as an immune pathway or cell division.

In an additional aspect of the invention, a Cas9 enzyme may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (D10 and H840) in the RuvC and HNH catalytic domains, respectively. Further mutations have been characterized. In one aspect of the invention, the functional domain may be a transcriptional activation domain, which may be VP64. In other aspects of the invention, the functional domain may be a transcriptional repressor domain, which may be KRAB or SID4X. Other aspects of the invention relate to the mutated Cas 9 enzyme being fused to domains which include but are not limited to a transcriptional activator, repressor, a recombinase, a transposase, a histone remodeler, a demethylase, a DNA methyltransferase, a cryptochrome, a light inducible/controllable domain or a chemically inducible/controllable domain. Some methods of the invention can include inducing expression of targeted genes. In one embodiment, inducing expression by targeting a plurality of target sequences in a plurality of genomic loci in a population of eukaryotic cells is by use of a functional domain.

Useful in the practice of the instant invention, reference is made to:
  Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print]; Published in final edited form as: Science. 2014 Jan. 3; 343 (6166): 84-87.
  Shalem et al. involves a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Reference is also made to US patent publication number US20140357530; and PCT Patent Publication WO2014093701, hereby incorporated herein by reference.

With respect to use of the CRISPR-Cas system generally, mention is made of the documents, including patent applications, patents, and patent publications cited throughout this disclosure as embodiments of the invention can be used as in those documents. CRISPR-Cas System(s) can be used to perform saturating or deep scanning mutagenesis of genomic loci in conjunction with a cellular phenotype—for instance, for determining critical minimal features and discrete vulnerabilities of functional elements required for gene expression, drug resistance, and reversal of disease. By saturating or deep scanning mutagenesis is meant that every or essentially every DNA base is cut within the genomic loci. A library of CRISPR-Cas guide RNAs may be introduced into a population of cells. The library may be introduced, such that each cell receives a single guide RNA (sgRNA). In the case where the library is introduced by transduction of a viral vector, as described herein, a low multiplicity of infection (MOI) is used. The library may include sgRNAs targeting every sequence upstream of a (protospacer adjacent motif) (PAM) sequence in a genomic locus. The library may include at least 100 non-overlapping genomic sequences upstream of a PAM sequence for every 1000 base pairs within the genomic locus. The library may include sgRNAs targeting sequences upstream of at least one different PAM sequence. The CRISPR-Cas System(s) may include more than one Cas protein. Any Cas protein as described herein, including orthologues or engineered Cas proteins that recognize different PAM sequences may be used. The frequency of off target sites for a sgRNA may be less than 500. Off target scores may be generated to select sgRNAs with the lowest off target sites. Any phenotype determined to be associated with cutting at a sgRNA target site may be confirmed by using sgRNA's targeting the same site in a single experiment. Validation of a target site may also be performed by using a nickase Cas9, as described herein, and two sgRNAs targeting the genomic site of interest. Not being bound by a theory, a target site is a true hit if the change in phenotype is observed in validation experiments.

The genomic loci may include at least one continuous genomic region. The at least one continuous genomic region may comprise up to the entire genome. The at least one continuous genomic region may comprise a functional element of the genome. The functional element may be within a non-coding region, coding gene, intronic region, promoter, or enhancer. The at least one continuous genomic region may comprise at least 1 kb, preferably at least 50 kb of genomic DNA. The at least one continuous genomic region may comprise a transcription factor binding site. The at least one continuous genomic region may comprise a region of DNase I hypersensitivity. The at least one continuous genomic region may comprise a transcription enhancer or repressor element. The at least one continuous genomic region may comprise a site enriched for an epigenetic signature. The at least one continuous genomic DNA region may comprise an epigenetic insulator. The at least one continuous genomic region may comprise two or more continuous genomic regions that physically interact. Genomic regions that interact may be determined by '4C technology'. 4C technology allows the screening of the entire genome in an unbiased manner for DNA segments that physically interact with a DNA fragment of choice, as is described in Zhao et al. ((2006) Nat Genet 38, 1341-7) and in U.S. Pat. No. 8,642,295, both incorporated herein by reference in its entirety. The epigenetic signature may be histone acetylation, histone methylation, histone ubiquitination, histone phosphorylation, DNA methylation, or a lack thereof.

CRISPR-Cas System(s) for saturating or deep scanning mutagenesis can be used in a population of cells. The CRISPR-Cas System(s) can be used in eukaryotic cells, including but not limited to mammalian and plant cells. The population of cells may be prokaryotic cells. The population of eukaryotic cells may be a population of embryonic stem (ES) cells, neuronal cells, epithelial cells, immune cells, endocrine cells, muscle cells, erythrocytes, lymphocytes, plant cells, or yeast cells.

In one aspect, the present invention provides for a method of screening for functional elements associated with a change in a phenotype. The library may be introduced into a population of cells that are adapted to contain a Cas protein. The cells may be sorted into at least two groups based on the phenotype. The phenotype may be expression of a gene, cell growth, or cell viability. The relative representation of the guide RNAs present in each group are determined, whereby genomic sites associated with the change in phenotype are determined by the representation of guide RNAs present in each group. The change in phenotype may be a change in expression of a gene of interest. The gene of interest may be upregulated, downregulated, or knocked out. The cells may be sorted into a high expression group and a low expression group. The population of cells may include a reporter construct that is used to determine the phenotype. The reporter construct may include a detectable marker. Cells may be sorted by use of the detectable marker.

In another aspect, the present invention provides for a method of screening for genomic sites associated with resistance to a chemical compound. The chemical compound may be a drug or pesticide. The library may be introduced into a population of cells that are adapted to contain a Cas protein, wherein each cell of the population contains no more than one guide RNA; the population of cells are treated with the chemical compound; and the representation of guide RNAs are determined after treatment with the chemical compound at a later time point as compared to an early time point, whereby genomic sites associated with resistance to the chemical compound are determined by enrichment of guide RNAs. Representation of sgRNAs may be determined by deep sequencing methods.

Useful in the practice of the instant invention, reference is made to the article entitled BCL11A enhancer dissection by Cas9-mediated in situ saturating mutagenesis. Canver, M. C., Smith, E. C., Sher, F., Pinello, L., Sanjana, N. E., Shalem, O., Chen, D. D., Schupp, P. G., Vinjamur, D. S., Garcia, S. P., Luc, S., Kurita, R., Nakamura, Y., Fujiwara, Y., Maeda, T., Yuan, G., Zhang, F., Orkin, S. H., & Bauer, D. E. DOI:10.1038/nature15521, published online Sep. 16, 2015, the article is herein incorporated by reference and discussed briefly below:

Canver et al. involves novel pooled CRISPR-Cas9 guide RNA libraries to perform in situ saturating mutagenesis of the human and mouse BCL11A erythroid enhancers previously identified as an enhancer associated with fetal hemoglobin (HbF) level and whose mouse ortholog is necessary for erythroid BCL11A expression. This approach revealed critical minimal features and discrete vulnerabilities of these enhancers. Through editing of primary human progenitors and mouse transgenesis, the authors validated the BCL11A erythroid enhancer as a target for HbF reinduction. The authors generated a detailed enhancer map that informs therapeutic genome editing.

Self-Inactivating Systems

Once all copies of a gene in the genome of a cell have been edited, continued CRISRP/Cas9 expression in that cell is no longer necessary. Indeed, sustained expression would be undesirable in case of off-target effects at unintended genomic sites, etc. Thus time-limited expression would be useful. Inducible expression offers one approach, but in addition Applicants have engineered a Self-Inactivating CRISPR-Cas9 system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self inactivating CRISPR-Cas system includes additional RNA (i.e., guide RNA) that targets the coding sequence for the CRISPR enzyme itself or that targets one or more non-coding guide target sequences complementary to unique sequences present in one or more of the following:

(a) within the promoter driving expression of the non-coding RNA elements,
(b) within the promoter driving expression of the Cas9 gene,
(c) within 100 bp of the ATG translational start codon in the Cas9 coding sequence,
(d) within the inverted terminal repeat (iTR) of a viral delivery vector, e.g., in the AAV genome.

Furthermore, that RNA can be delivered via a vector, e.g., a separate vector or the same vector that is encoding the CRISPR complex. When provided by a separate vector, the CRISPR RNA that targets Cas expression can be administered sequentially or simultaneously. When administered sequentially, the CRISPR RNA that targets Cas expression is to be delivered after the CRISPR RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas enzyme associates with a first gRNA/chiRNA capable of hybridizing to a first target, such as a genomic locus or loci of interest and undertakes the function(s) desired of the CRISPR-Cas system (e.g., gene engineering); and subsequently the Cas enzyme may then associate with the second gRNA/chiRNA capable of hybridizing to the sequence comprising at least part of the Cas or CRISPR cassette. Where the gRNA/chiRNA targets the sequences encoding expression of the Cas protein, the enzyme becomes impeded and the system becomes self inactivating. In the same manner, CRISPR RNA that targets Cas expression applied via, for example liposome, lipofection, nanoparticles, microvesicles as explained herein, may be administered sequentially or simultaneously. Similarly, self-inactivation may be used for inactivation of one or more guide RNA used to target one or more targets.

In some aspects, a single gRNA is provided that is capable of hybridization to a sequence downstream of a CRISPR enzyme start codon, whereby after a period of time there is a loss of the CRISPR enzyme expression. In some aspects, one or more gRNA(s) are provided that are capable of hybridization to one or more coding or non-coding regions of the polynucleotide encoding the CRISPR-Cas system, whereby after a period of time there is a inactivation of one or more, or in some cases all, of the CRISPR-Cas system. In some aspects of the system, and not to be limited by theory, the cell may comprise a plurality of CRISPR-Cas complexes, wherein a first subset of CRISPR complexes comprise a first chiRNA capable of targeting a genomic locus or loci to be edited, and a second subset of CRISPR complexes comprise at least one second chiRNA capable of targeting the polynucleotide encoding the CRISPR-Cas system, wherein the first subset of CRISPR-Cas complexes mediate editing of the targeted genomic locus or loci and the second subset of CRISPR complexes eventually inactivate the CRISPR-Cas system, thereby inactivating further CRISPR-Cas expression in the cell.

Thus the invention provides a CRISPR-Cas system comprising one or more vectors for delivery to a eukaryotic cell, wherein the vector(s) encode(s): (i) a CRISPR enzyme; (ii) a first guide RNA capable of hybridizing to a target sequence in the cell; (iii) a second guide RNA capable of hybridizing to one or more target sequence(s) in the vector which encodes the CRISPR enzyme; (iv) at least one tracr mate sequence; and (v) at least one tracr sequence, The first and second complexes can use the same tracr and tracr mate, thus differing only by the guide sequence, wherein, when expressed within the cell: the first guide RNA directs sequence-specific binding of a first CRISPR complex to the target sequence in the cell; the second guide RNA directs sequence-specific binding of a second CRISPR complex to the target sequence in the vector which encodes the CRISPR enzyme; the CRISPR complexes comprise (a) a tracr mate sequence hybridised to a tracr sequence and (b) a CRISPR enzyme bound to a guide RNA, such that a guide RNA can hybridize to its target sequence; and the second CRISPR complex inactivates the CRISPR-Cas system to prevent continued expression of the CRISPR enzyme by the cell.

Further characteristics of the vector(s), the encoded enzyme, the guide sequences, etc. are disclosed elsewhere herein. For instance, one or both of the guide sequence(s) can be part of a chiRNA sequence which provides the guide, tracr mate and tracr sequences within a single RNA, such that the system can encode (i) a CRISPR enzyme; (ii) a first chiRNA comprising a sequence capable of hybridizing to a first target sequence in the cell, a first tracr mate sequence, and a first tracr sequence; (iii) a second guide RNA capable of hybridizing to the vector which encodes the CRISPR enzyme, a second tracr mate sequence, and a second tracr sequence. Similarly, the enzyme can include one or more NLS, etc.

The various coding sequences (CRISPR enzyme, guide RNAs, tracr and tracr mate) can be included on a single vector or on multiple vectors. For instance, it is possible to encode the enzyme on one vector and the various RNA sequences on another vector, or to encode the enzyme and one chiRNA on one vector, and the remaining chiRNA on another vector, or any other permutation. In general, a system using a total of one or two different vectors is preferred.

Where multiple vectors are used, it is possible to deliver them in unequal numbers, and ideally with an excess of a vector which encodes the first guide RNA relative to the second guide RNA, thereby assisting in delaying final inactivation of the CRISPR system until genome editing has had a chance to occur.

The first guide RNA can target any target sequence of interest within a genome, as described elsewhere herein. The second guide RNA targets a sequence within the vector which encodes the CRISPR Cas9 enzyme, and thereby inactivates the enzyme's expression from that vector. Thus the target sequence in the vector must be capable of inactivating expression. Suitable target sequences can be, for instance, near to or within the translational start codon for the Cas9 coding sequence, in a non-coding sequence in the promoter driving expression of the non-coding RNA elements, within the promoter driving expression of the Cas9 gene, within 100 bp of the ATG translational start codon in the Cas9 coding sequence, and/or within the inverted terminal repeat (iTR) of a viral delivery vector, e.g., in the AAV genome. A double stranded break near this region can induce a frame shift in the Cas9 coding sequence, causing a loss of protein expression. An alternative target sequence for the "self-inactivating" guide RNA would aim to edit/inactivate regulatory regions/sequences needed for the expression of the CRISPR-Cas9 system or for the stability of the vector. For instance, if the promoter for the Cas9 coding sequence is disrupted then transcription can be inhibited or prevented. Similarly, if a vector includes sequences for replication, maintenance or stability then it is possible to target these. For instance, in a AAV vector a useful target sequence is within the iTR. Other useful sequences to target can be promoter sequences, polyadenlyation sites, etc.

Furthermore, if the guide RNAs are expressed in array format, the "self-inactivating" guide RNAs that target both promoters simultaneously will result in the excision of the intervening nucleotides from within the CRISPR-Cas expression construct, effectively leading to its complete inactivation. Similarly, excision of the intervening nucleotides will result where the guide RNAs target both ITRs, or targets two or more other CRISPR-Cas components simultaneously. Self-inactivation as explained herein is applicable, in general, with CRISPR-Cas9 systems in order to provide regulation of the CRISPR-Cas9. For example, self-inactivation as explained herein may be applied to the CRISPR repair of mutations, for example expansion disorders, as explained herein. As a result of this self-inactivation, CRISPR repair is only transiently active.

Addition of non-targeting nucleotides to the 5' end (e.g. 1-10 nucleotides, preferably 1-5 nucleotides) of the "self-inactivating" guide RNA can be used to delay its processing and/or modify its efficiency as a means of ensuring editing at the targeted genomic locus prior to CRISPR-Cas9 shutdown.

In one aspect of the self-inactivating AAV-CRISPR-Cas9 system, plasmids that co-express one or more sgRNA targeting genomic sequences of interest (e.g. 1-2, 1-5, 1-10, 1-15, 1-20, 1-30) may be established with "self-inactivating" sgRNAs that target an SpCas9 sequence at or near the engineered ATG start site (e.g. within 5 nucleotides, within 15 nucleotides, within 30 nucleotides, within 50 nucleotides, within 100 nucleotides). A regulatory sequence in the U6 promoter region can also be targeted with an sgRNA. The U6-driven sgRNAs may be designed in an array format such that multiple sgRNA sequences can be simultaneously released. When first delivered into target tissue/cells (left cell) sgRNAs begin to accumulate while Cas9 levels rise in the nucleus. Cas9 complexes with all of the sgRNAs to mediate genome editing and self-inactivation of the CRISPR-Cas9 plasmids.

One aspect of a self-inactivating CRISPR-Cas9 system is expression of singly or in tandam array format from 1 up to 4 or more different guide sequences; e.g. up to about 20 or about 30 guides sequences. Each individual self inactivating guide sequence may target a different target. Such may be processed from, e.g. one chimeric pol3 transcript. Pol3 promoters such as U6 or H1 promoters may be used. Pol2 promoters such as those mentioned throughout herein. Inverted terminal repeat (iTR) sequences may flank the Pol3 promoter—sgRNA(s)-Pol2 promoter—Cas9.

One aspect of a chimeric, tandem array transcript is that one or more guide(s) edit the one or more target(s) while one or more self inactivating guides inactivate the CRISPR/Cas9 system. Thus, for example, the described CRISPR-Cas9 system for repairing expansion disorders may be directly combined with the self-inactivating CRISPR-Cas9 system described herein. Such a system may, for example, have two guides directed to the target region for repair as well as at least a third guide directed to self-inactivation of the CRISPR-Cas9. Reference is made to Application Ser. No. PCT/US2014/069897, entitled "Compositions And Methods Of Use Of Crispr-Cas Systems In Nucleotide Repeat Disorders," published Dec. 12, 2014 as WO/2015/089351.

One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to FokI cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In advantageous embodiments of the invention, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-($X_{12}X_{13}$)-$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as ($X_{1-11}$-($X_{12}X_{13}$)-$X_{14-33}$ or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine and thymine with comparable affinity.

Figure 8:
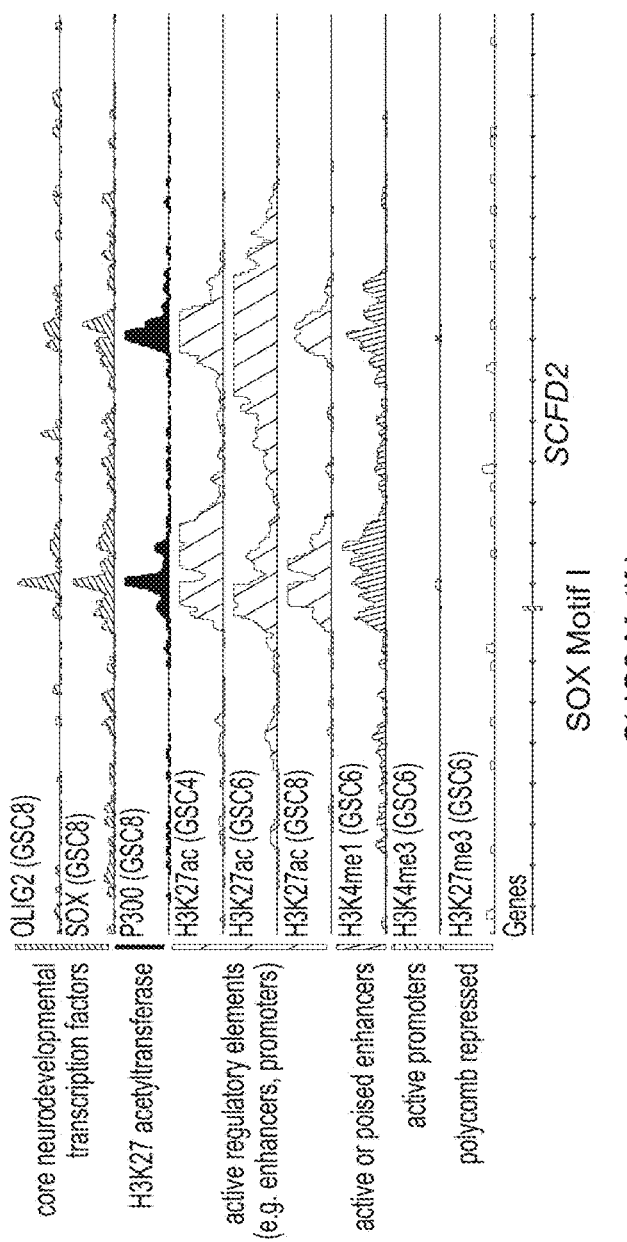
FIG. 8A-8C illustrates characterization of the FIP1L1 enhancer. (a) H3K27ac ChIP-seq track for GSC6 gliomaspheres reveals strong enrichment over the FIP1L1 enhancer. CTCF ChIP-seq track reveals location of the boundary element insulator (as in FIG. 3a). FIP1L1 enhancer (i) and promoter (ii) are indicated. (b) H3K27ac ChIP-seq tracks for IDH mutant and wild-type gliomaspheres and glioma specimens reveal enrichment over the FIP1L1 enhancer. (c) ChIP-seq tracks for glioma master transcription factors and other histone modifications support the enhancer identity of the element (H3K27ac, H3K4me1, SOX2, OLIG2; lacks H3K4me3, lacks H3K27me3). In contrast, the FIP1L1 promoter has a distinct 'promoter-like' chromatin state.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8). Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                                  (SEQ ID NO: 25[[147]])
M D P I R S R T P S P A R E L L S G P Q P D G V Q P T A D R G V S P

P A G G P L D G L P A R R T M S R T R L P S P P A P S P A F S A D S

F S D L L R Q F D P S L F N T S L F D S L P P F G A H H T E A A T G

E W D E V Q S G L R A A D A P P P T M R V A V T A A R P P R A K P A

P R R R A A Q P S D A S P A A Q V D L R T L G Y S Q Q Q Q E K I K P

K V R S T V A Q H H E A L V G H G F T H A H I V A L S Q H P A A L G

T V A V K Y Q D M I A A L P E A T H E A I V G V G K Q W S G A R A L

E A L L T V A G E L R G P P L Q L D T G Q L L K I A K R G G V T A V

E A V H A W R N A L T G A P L N
```

An exemplary amino acid sequence of a C-terminal capping region is:

```
                                                  (SEQ ID NO: 26[[148]])
R P A L E S I V A Q L S R P D P A L A A L T N D H L V A L A C L G

G R P A L D A V K K G L P H A P A L I K R T N R R I P E R T S H R

V A D H A Q V V R V L G F F Q C H S H P A Q A F D D A M T Q F G M

S R H G L L Q L F R R V G V T E L E A R S G T L P P A S Q R W D R

I L Q A S G M K R A K P S P T S T Q T P D Q A S L H A F A D S L E

R D L D A P S P M H E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides, Zinc finger proteins and CRISPR systems described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, histone methyltransferase, histone demethylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, histone methyltransferase activity, histone demethylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

The detection of DNA methylation within CTCF binding motifs for use in a diagnostic or screening protocol may use any method known in the art. For techniques useful in detecting DNA methylation in a biological sample reference is made to: Methods in Molecular Biology, Volume 507, 2009, DNA Methylation Methods and Protocols, Editors: Jörg Tost, ISBN: 978-1-934115-61-9 (Print) 978-1-59745-522-0 (Online). Exemplary techniques include, but are not limited to Methylated DNA Immunoprecipitation (MeDIP), The MIRA Method for DNA Methylation Analysis, The Help Assay, Differential Methylation Hybridization: Profiling DNA Methylation with a High-Density CpG Island Microarray, Analysis of DNA Methylation by Amplification of Intermethylated Sites (AIMS), Methylation-Sensitive Representational Difference Analysis (MS-RDA), Restriction Landmark Genomic Scanning: Analysis of CpG Islands in Genomes by 2D Gel Electrophoresis, GoldenGate® Assay for DNA Methylation Profiling, 5'-Azacytidine Expression Arrays, DNA Methylation Analysis by Bisulfite Conversion, Cloning, and Sequencing of Individual Clones, Identification and Quantification of Differentially Methylated Loci by the Pyrosequencing™ Technology, Mass Spectrometric Analysis of Cytosine Methylation by Base-Specific Cleavage and Primer Extension Methods, Melting Curve Assays for DNA Methylation Analysis, Methylation SNaPshot: A Method for the Quantification of Site-Specific DNA Methylation Levels, Bio-COBRA: Absolute Quantification of DNA Methylation in Electrofluidics Chips, Restriction Digestion and Real-Time PCR (qAMP), MethylQuant: A Real-Time PCR-Based Method to Quantify DNA Methylation at Single Specific Cytosines, Methylation-Specific PCR, MethyLight, Quantification of Methylated DNA by HeavyMethyl Duplex PCR, bisulfate sequencing, and Methylation-sensitive single-nucleotide primer extension (Ms-SNuPE) (Nat Protoc. 2007; 2(8):1931-6).

Methods of detecting DNA methylation in biological samples are known in the art. For preparing DNA for methylation analysis from urine reference is made to U.S. Pat. No. 9,096,905.

Chromosome conformation capture, or 3C, is a high-throughput molecular biology technique used to analyze the organization of chromosomes in a cell's natural state (Dekker J, Rippe K, Dekker M, Kleckner N (2002). "Capturing chromosome conformation". Science 295 (5558): 1306-1311. doi:10.1126/science.1067799. PMID 11847345). Studying the structural properties and spatial organization of chromosomes is important for the understanding and evaluation of the regulation of gene expression, DNA replication and repair, and recombination. Reference is also made to methods of HiC described in Rao et al., A 3D Map of the Human Genome at Kilobase Resolution Reveals Principles of Chromatin Looping. Cell 159, 1665-1680, Dec. 18, 2014; and Sanborn et al., Chromatin extrusion explains key features of loop and domain formation in wild-type and engineered genomes. PNAS, Published online Oct. 23, 2015, incorporated herein by reference in its entirety.

One example of chromosomal interactions influencing gene expression is a chromosomal region which can fold in order to bring an enhancer and associated transcription factors within close proximity of a gene, as was first shown in the beta-globin locus. Chromosome conformation capture has enabled researchers to study the influences of chromosomal activity on the aforementioned cellular mechanisms. This technology has aided the genetic and epigenetic study of chromosomes both in model organisms and in humans.

Several techniques have been developed from 3C to increase the throughput of quantifying a chromosome's interactions with other chromosomes and with proteins. All the 3C related technologies are broadly categorized into four groups. (1) 3C and ChIP version of 3C (ChIP-loop assay), (2) 4C and ChIP version of 4C (enhanced 4C), (3) 5C and 3D assays and (4) Genome conformation capture (GCC)

related (Hi-C), ChIP version of GCC as 6C. The application of analyzing DNA segments by microarray and high-throughput sequencing in the 4C, 5C and Hi-C methodologies has brought the assessment of chromosome interactions to the genome-wide scale. Genomic regions that interact may be determined by '4C technology'. 4C technology allows the screening of the entire genome in an unbiased manner for DNA segments that physically interact with a DNA fragment of choice, as is described in Zhao et al. ((2006) Nat Genet 38, 1341-7) and in U.S. Pat. No. 8,642,295, both incorporated herein by reference in its entirety.

Detecting aberrant looping may also use 3D DNA FISH (Giorgetti L, Piolot T, Heard E., High-resolution 3D DNA FISH using plasmid probes and computational correction of optical aberrations to study chromatin structure at the sub-megabase scale, Methods Mol Biol. 2015; 1262:37-53). Not being bound by a theory, the conditions preserve 3D nuclear structure and single cells may be quantitated for aberrant chromatin looping at specific topological associated domains using 3D DNA FISH.

Detecting aberrant gene expression of genes within a topological associated domain may also be used to detect aberrant chromatin topology. Not being bound by a theory, disruption of insulators allows topological associated domain to interact, such that an enhancer interacts with an oncogene, thus changing the gene expression of the oncogene.

CTCF binding to an insulator region may be performed by a combination of FISH and immunofluorescence as described in U.S. patent application publication 20150065371 and international application publication number WO2013101612. Not being bound by a theory a section of a patient tumor can be analyzed at any time during, before or after treatment for the presence of cells that have lost CTCF binding to a specific insulator.

Isolation of circulating tumor cells (CTC) for use in any of the diagnostic methods described herein may be performed. Exemplary technologies that achieve specific and sensitive detection and capture of CTCs may be used in the present invention have been described (Mostert B, et al., Circulating tumor cells (CTCs): detection methods and their clinical relevance in breast cancer. Cancer Treat Rev. 2009; 35:463-474; and Talasaz A H, et al., Isolating highly enriched populations of circulating epithelial cells and other rare cells from blood using a magnetic sweeper device. Proc Natl Acad Sci USA. 2009; 106:3970-3975). As few as one CTC may be found in the background of 105-106 peripheral blood mononuclear cells (Ross A A, et al., Detection and viability of tumor cells in peripheral blood stem cell collections from breast cancer patients using immunocytochemical and clonogenic assay techniques. Blood. 1993; 82:2605-2610). The CellSearch® platform uses immunomagnetic beads coated with antibodies to Epithelial Cell Adhesion Molecule (EpCAM) to enrich for EPCAM-expressing epithelial cells, followed by immunostaining to confirm the presence of cytokeratin staining and absence of the leukocyte marker CD45 to confirm that captured cells are epithelial tumor cells (Momburg F, et al., Immunohistochemical study of the expression of a Mr 34,000 human epithelium-specific surface glycoprotein in normal and malignant tissues. Cancer Res. 1987; 47:2883-2891; and Allard W J, et al., Tumor cells circulate in the peripheral blood of all major carcinomas but not in healthy subjects or patients with nonmalignant diseases. Clin Cancer Res. 2004; 10:6897-6904). The number of cells captured in this assay has been prospectively demonstrated to have prognostic significance for breast, colorectal and prostate cancer patients with advanced disease Cohen S J, et al., J Clin Oncol. 2008; 26:3213-3221; Cristofanilli M, et al. N Engl J Med. 2004; 351:781-791; Cristofanilli M, et al., J Clin Oncol. 2005; 23:1420-1430; and de Bono J S, et al. Clin Cancer Res. 2008; 14:6302-6309).

The present invention also provides for isolating CTCs with CTC-Chip Technology. CTC-Chip is a microfluidic based CTC capture device where blood flows through a chamber containing thousands of microposts coated with anti-EpCAM antibodies to which the CTCs bind (Nagrath S, et al. Isolation of rare circulating tumour cells in cancer patients by microchip technology. Nature. 2007; 450:1235-1239). CTC-Chip provides a significant increase in CTC counts and purity in comparison to the CellSearch® system (Maheswaran S, et al. Detection of mutations in EGFR in circulating lung-cancer cells. N Engl J Med. 2008; 359:366-377). Both platforms may be used for downstream molecular analysis. Examples include immunofluorescence for IGF-1R and the DNA damage response marker, gH2AX, in Phase I studies (de Bono J S, et al. Clin Cancer Res. 2007; 13:3611-3616; Wang L H, et al. Clin Cancer Res. 16:1073-1084), EGFR (Smith G D, et al. J Clin Pathol. 2008; 61:487-493) and HER2 (Pestrin M, et al. Breast Cancer Res Treat. 2009; 118:523-530) status in breast cancer, FISH for PTEN and FISH and RNA for TMPRSS2-ERG fusion in prostate cancer (Attard G, et al. Cancer Res. 2009; 69:2912-2918; (Stott S L, et al. Sci Transl Med. 2:25ra23), and genotyping for EGFR mutations in lung cancer (Maheswaran S, et al. N Engl J Med. 2008; 359:366-377).

The practice of the present invention employs, unless otherwise indicated, conventional techniques of immunology, biochemistry, chemistry, molecular biology, microbiology, cell biology, genomics and recombinant DNA, which are within the skill of the art. See MOLECULAR CLONING: A LABORATORY MANUAL, 2nd edition (1989) (Sambrook, Fritsch and Maniatis); MOLECULAR CLONING: A LABORATORY MANUAL, 4th edition (2012) (Green and Sambrook); CURRENT PROTOCOLS IN MOLECULAR BIOLOGY (1987) (F. M. Ausubel, et al. eds.); the series METHODS IN ENZYMOLOGY (Academic Press, Inc.); PCR 2: A PRACTICAL APPROACH (1995) (M. J. MacPherson, B. D. Hames and G. R. Taylor eds.); ANTIBODIES, A LABORATORY MANUAL (1988) (Harlow and Lane, eds.); ANTIBODIES A LABORATORY MANUAL, 2nd edition (2013) (E. A. Greenfield ed.); and ANIMAL CELL CULTURE (1987) (R.I. Freshney, ed.).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

The present invention advantageously provides for new therapeutic regimens for cancers or genetic diseases having a mutation in IDH. IDH mutant tumors can be advantageously treated with a combination of an IDH inhibitor plus an inhibitor of an oncogene, preferably a receptor tyrosine kinase, that is indirectly over-expressed as a result of the IDH mutation.

The present invention also advantageously provides for methods of guiding therapy detection of disrupted insulators and overexpressed oncogenes that are activated due to loss of insulator function. Thus, the present invention provides novel diagnostics and screening tools for detecting cancer, monitoring disease progression, and effectively treating a patient in need thereof.

The present invention also advantageously provides for diagnostic methods to assess DNA hypermethylation at CTCF binding motifs cancer, CTCF binding, and chromatin interaction.

The present also advantageously provides for novel therapeutic compositions for treating cancer or preventing the onset of cancer. Insulator disrupted tumors may be now be chosen as targets for DNA demethylating agents alone or in combination with inhibitors of oncogenes or mutated genes found in tumors.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1. CTCF Binding and Gene Insulation is Compromised in IDH Mutant Gliomas Since CTCF binding is methylation-sensitive[18,19], its localization might be altered by DNA hyper-methylation in IDH mutant gliomas. Applicants therefore used ChIP-seq to map CTCF binding genome-wide in eleven primary tumors and four glioma lines. Although CTCF binding patterns tend to be relatively stable, Applicants detected highly overlapping subsets of CTCF sites lost in IDH mutants (FIG. 1a-b; see Methods). Significantly more sites were commonly lost than gained (625 vs 300, $p<10^{-12}$). Applicants used whole genome bisulfite sequencing data from the Cancer Genome Atlas (TCGA)[10] to assess the methylation status of 625 loci with reduced CTCF binding in mutant tumors. Applicants found that these loci have higher GC content, and exhibit significantly higher levels of DNA methylation in IDH mutant gliomas, relative to IDH wildtype (FIG. 1c-d).

Applicants considered that altered DNA methylation and CTCF binding might disrupt topological domain boundaries and gene insulation in IDH mutant tumors. Applicants collated a set of constitutive domain boundaries based on kilobase-resolution HiC maps[15]. Applicants then examined published RNA-seq expression data for 357 normal brain tissue samples[20]. Consistent with prior studies[16], Applicants found that genes in the same domain correlate across samples, but that genes separated by a boundary show lower correlation (FIG. 1e). Applicants next incorporated expression data for 230 IDH mutant and 56 wildtype lower-grade gliomas, generated by the Cancer Genome Atlas (TCGA)[2]. Here again Applicants found that the presence of an intervening boundary reduces correlation between neighboring genes. Applicants next scanned the genome for pairs of proximal genes separated by less than 180 kb (the average contact domain size[15]) that correlate much more strongly in IDH mutants than in wildtype gliomas (FIG. 1f; see Methods). Remarkably, the resulting set is strongly enriched for gene pairs that cross domain boundaries (90% vs 69% expected at random; $p<10^{-4}$). Conversely, gene pairs that correlate less strongly in IDH mutants are more likely to reside in the same domain (52% vs 31% expected at random; $p<10^{-5}$). Notably, CTCF knock-down has been shown to increase cross-boundary interactions and decrease intra-domain interactions[21]. Thus, altered expression patterns in IDH mutant gliomas may reflect reduced CTCF binding and consequent disruption of domain boundaries and topologies.

A similar mutation in the succinate dehydrogenase genes (SDHA, SDHB, SDHC, SDHD) also leads to hypermethylation in several tumors, including gastrointestinal stromal tumors (GISTs), pheochromocytomas, and paragangliomas. There are also genetic syndromes caused by germline SDH mutations which predispose to these tumors (Carney-Stratakis Syndrome), or a variant of Cowden Syndrome which predisposes to breast and thyroid cancer.

Figure 5:
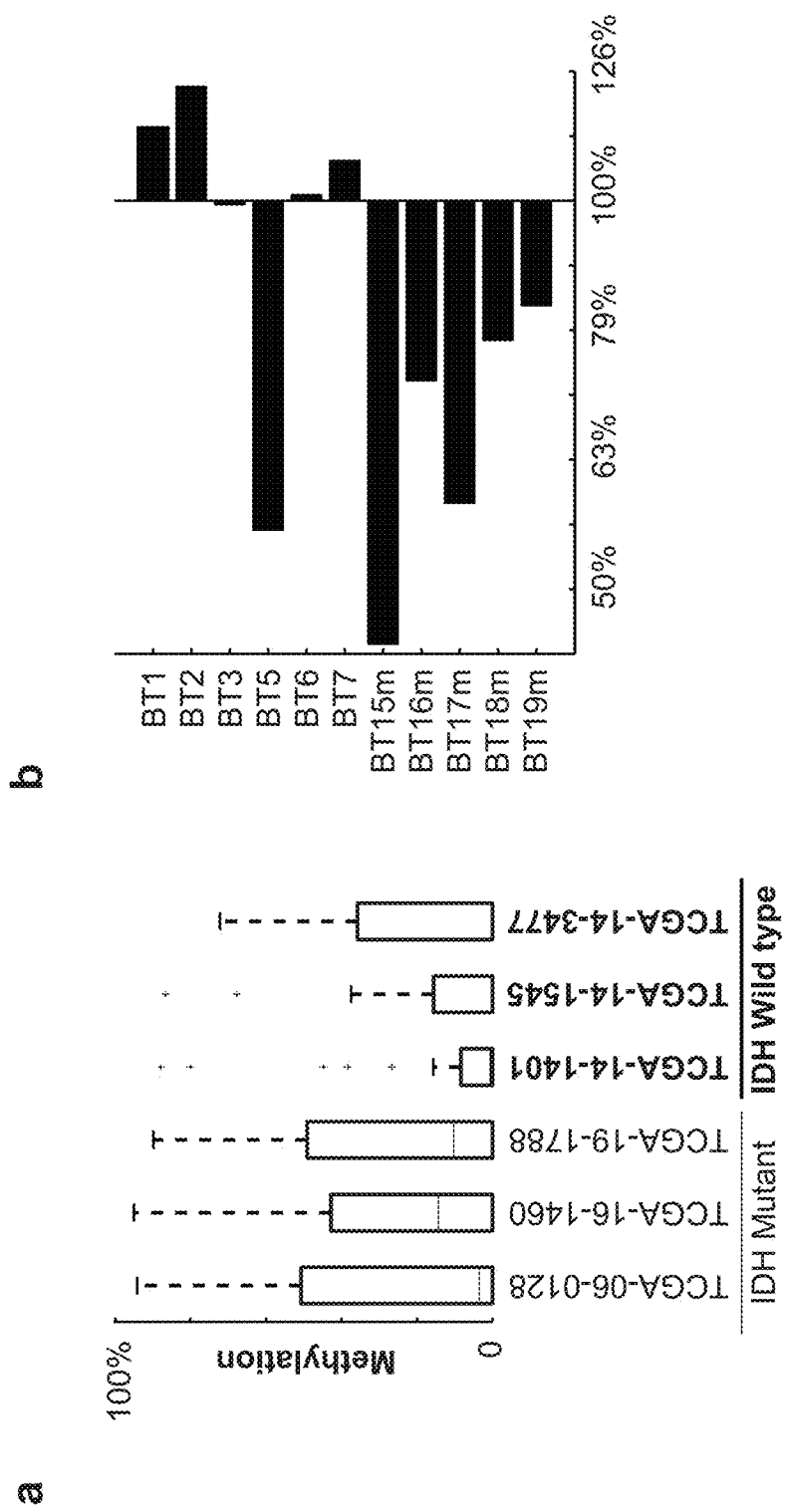
FIG. 5A-5B illustrates DNA methylation and CTCF binding at deregulated boundaries. (a) Box plots show DNA methylation levels over CTCF sites (200 bp window centered on the peak) within boundaries predicted by gene pair correlation analysis to be disrupted. All CTCF sites located within a 1 kb window centered on a disrupted boundary were considered. Methylation levels were determined from whole genome bisulfate data for three IDH mutant (red labels) and three IDH wildtype (black labels) tumors. (b) Bars show average normalized ChIP-seq signal over all CTCF sites located inside a 1 kb window centered on a disrupted boundary.

Example 2. Topological Domain Boundaries are Disrupted in IDH1 Mutant Gliomas Applicants next sought to pinpoint specific boundaries disrupted by IDH mutation. For all pairs of genes separated by <1 MB, Applicants computed their correlation across IDH mutant gliomas and across wildtype gliomas. Applicants then scanned for loci in which cross-boundary gene pairs correlate more strongly in mutant tumors (FDR<1%), while intra-domain gene pairs correlate less strongly (FDR<1%). This analysis highlighted 203 domain boundaries (FIG. 2a; Table S1; see Methods). The putatively disrupted boundaries exhibit higher DNA methylation and lower CTCF binding in IDH mutant tumors, relative to wildtype (FIG. 5). These data suggest that the methylator phenotype disrupts CTCF binding and domain boundaries, thereby affecting gene expression in IDH mutant gliomas.

Figure 2:
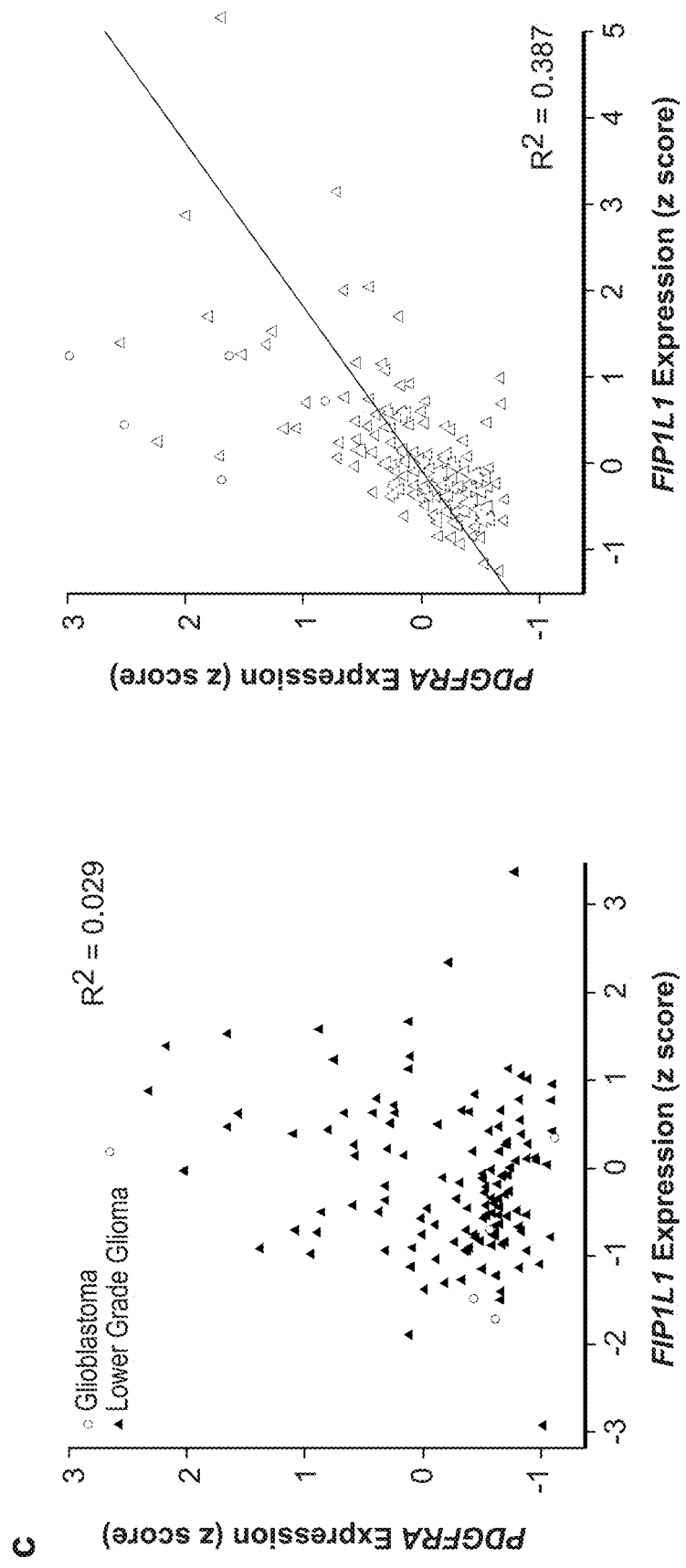
FIG. 2A-2C illustrates that topological domain boundaries are disrupted in IDH1 mutant gliomas. (a) Scatterplot depicts significance of deregulated boundaries in IDH mutant tumors (y-axis) against fold-change of most up-regulated gene in adjacent domains (x-axis). PDGFRA is adjacent to a significantly deregulated boundary and up-regulated in IDH mutants. (b) Boxplots compare PDGFRA expression (left) or copy number (right) for 443 glioblastoma tumors, classified by IDH status and expression subtype[24]. IDH mutants (red) have elevated PDGFRA expression, despite normal copy number. (c) Plots compare PDGFRA (y-axis) and FIP1L1 (x-axis) expression in IDH wildtype (left) and mutant (right) gliomas. The genes correlate specifically in IDH mutants, consistent with deregulation of the intervening boundary/insulator.

Applicants hypothesized that altered domain topologies might contribute to gliomagenesis by activating oncogenes that are normally insulated by domain boundaries. Applicants therefore scanned the domains adjacent to the disrupted boundaries for genes with higher expression in IDH mutant than wild-type gliomas (FIG. 2a). Genes in top scoring domains include PDGFRA ($p<10^{-21}$), an established glioma oncogene[22], and other candidate regulators of gliomagenesis (Table S1).

Figure 6:
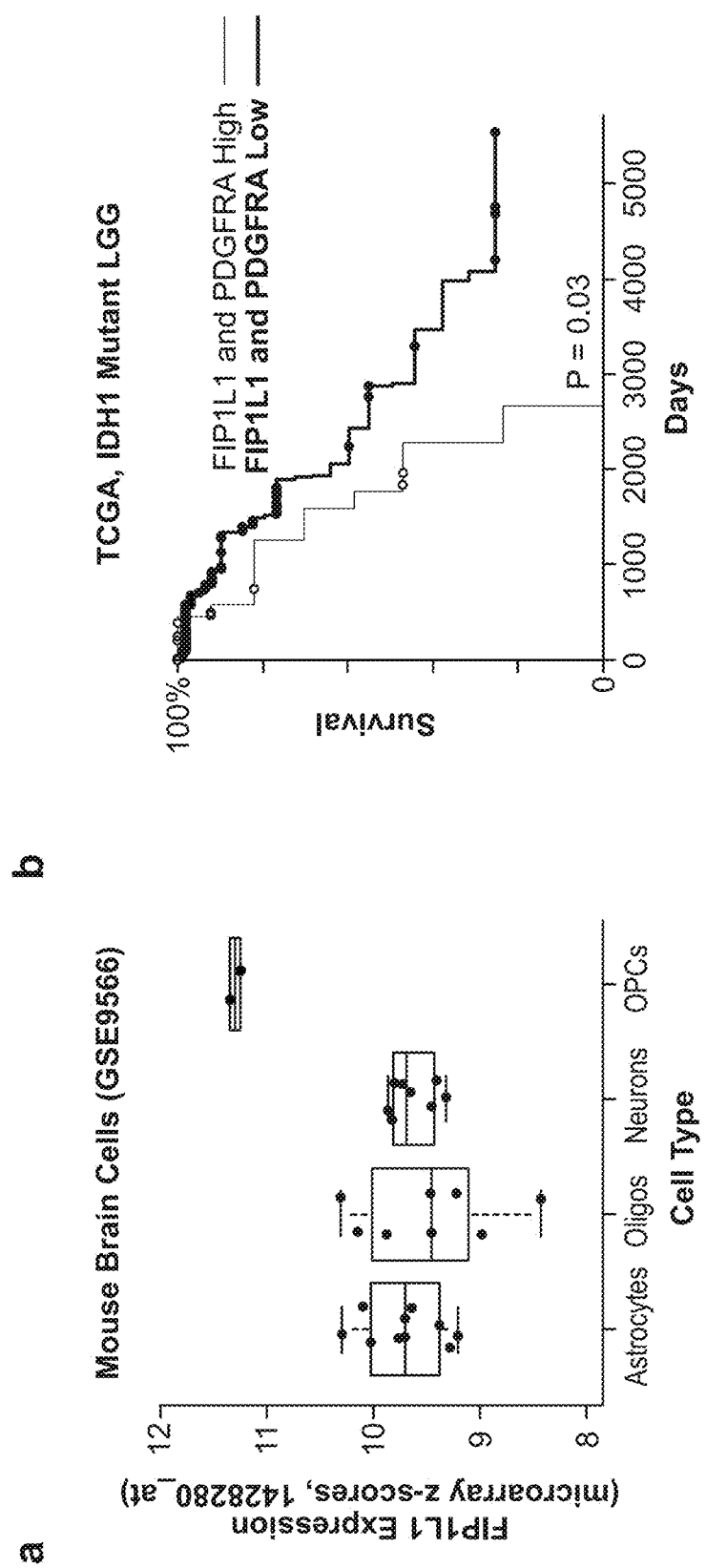
FIG. 6A-6B illustrates expression of FIP1L1 in mouse brain cells and survival effects of PDGFRA and FIP1L1 (a) Expression of FIP1L1 in isolated mouse brain cell types[44]. (b) Kaplan-Meier Plot based on TCGA data3 indicates that combined FIP1L1 and PDGFRA expression is a negative prognostic factor in IDH1 mutant lower-grade gliomas. Multivariate analysis including the known prognostic factor 1p/19q deletion diminished this effect into non-significance, suggesting that other predictors of survival may also play a role in this model.

The identification of PDGFRA as a potential target of epigenetic deregulation in IDH mutants was of particular interest, given its prominence as a glioma oncogene and established roles for PDGFA signaling in normal brain. Although PDGFRA is a frequent target of genomic amplification and gain-of-function mutations in glioblastoma (15%), such alterations are rare in IDH mutant tumors[23,24]. Nonetheless, IDH mutant gliomas strongly express PDGFRA (FIG. 2b), and share the proneural transcriptional program characteristic of PDGFRA-amplified tumors[23,24]. Closer examination of expression patterns in IDH mutant gliomas reveals a striking correlation between PDGFRA and FIP1L1, despite an intervening boundary (FIG. 2c). FIP1L1 encodes an RNA processing protein that is constitutively expressed in neural tissues, and particularly active in oligodendrocyte precursors, a putative glioma cell-of-origin[22] (FIG. 6a). Moreover, combined expression of PDGFRA and FIP1L1 is associated with poorer outcome in IDH mutant lower-grade gliomas (FIG. 6b). This suggests that an aberrant interaction with this constitutive locus may drive PDGFRA expression in IDH mutant tumors.

Supplementary Table 1. List of deregulated boundaries and genes. Table lists domains whose boundaries are predicted to be lost based on cross-boundary gene pairs that gain correlation and intra-domain gene pairs that lose correlation. All supporting gene pairs (FDR <1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 1 | 6.00E−42 | BUB1B-CHST14(9e−06); BUB1B-GPR176(6e−05); BUB1B-RAD51(6e−28) | BMF-BUB1B(1e−14) | | 15 | 40330000; 40500000 |
| 2 | 6.00E−34 | ATP5B-DCTN2(1e−05); BAZ2A-DTX3(1e−04); BAZ2A-MBD6(2e−07); BAZ2A-SLC26A10(8e−05); DCTN2-PTGES3(4e−06); DTX3-LRP1(1e−04); DTX3-TSFM(4e−05); OS9-R3HDM2(6e−07); OS9-TSFM(6e−05) | DCTN2-DDIT3(5e−20); DCTN2-MBD6(4e−27); DCTN2-TSPAN31(2e−20); DDIT3-MBD6(3e−26); DDIT3-TSPAN31(4e−21); MBD6-TSPAN31(4e−27) | | 12 | 57910000; 58140000 |
| 3 | 2.00E−33 | ACRBP-ATN1(7e−06); ACRBP-COPS7A(3e−05); ACRBP-GNB3(6e−05); ACRBP-IFFO1(3e−04); ACRBP-LEPREL2(5e−06); ACRBP-MLF2(1e−08); ATN1-CHD4(2e−05); ATN1-COPS7A(2e−09); ATN1-ING4(6e−07); ATN1-LEPREL2(4e−18); ATN1-MLF2(2e−15); ATN1-PTMS(7e−05); ATN1-USP5(9e−14); ATN1-ZNF384(4e−12); C12orf57-COPS7A(4e−06); C12orf57-MLF2(2e−04); C12orf57-USP5(8e−05); C1R-COPS7A(4e−12); C1R-ING4(3e−10); C1R- | GNB3-LEPREL2(1e−09) | | 12 | 6680000; 6970000; 6830000; 6960000 |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| | | LEPREL2(6e−07); C1R-MLF2(4e−13); C1R-USP5(3e−13); C1R-ZNF384(2e−05); C1RL-COPS7A(2e−09); C1RL-ING4(2e−06); C1RL-LEPREL2(1e−08); C1RL-MLF2(1e−11); C1RL-PTMS(1e−04); C1RL-USP5(4e−11); C1S-COPS7A(7e−14); C1S-ING4(9e−12); C1S-LEPREL2(6e−10); C1S-MLF2(3e−16); C1S-PTMS(3e−05); C1S-USP5(2e−16); C1S-ZNF384(3e−07); CD163-LPAR5(3e−04); CD4-LPAR5(6e−07); CD9-COPS7A(5e−06); CD9-LEPREL2(6e−06); CD9-MLF2(4e−07); CD9-USP5(1e−05); CHD4-COPS7A(2e−08); CHD4-GPR162(3e−05); CHD4-LEPREL2(3e−04); CHD4-MLF2(1e−08); CHD4-TPI1(3e−05); CLSTN3-ZNF384(2e−05); COPS7A-EMG1(2e−20); COPS7A-IFFO1(2e−06); COPS7A-ING4(1e−09); COPS7A- | | | | |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| | | LPCAT3(1e−16); COPS7A-LRRC23(6e−12); COPS7A-MRPL51(3e−13); COPS7A-NCAPD2(2e−11); COPS7A-NOP2(4e−12); COPS7A-PEX5(3e−08); COPS7A-PHB2(9e−13); COPS7A-RPL13P5(1e−08); COPS7A-SPSB2(7e−16); COPS7A-TAPBPL(3e−10); COPS7A-TNFRSF1A(5e−11); COPS7A-USP5(9e−08); COPS7A-ZNF384(3e−14); EMG1-GPR162(3e−04); EMG1-ING4(6e−07); EMG1-LEPREL2(8e−17); EMG1-MLF2(6e−16); EMG1-PTMS(4e−06); EMG1-USP5(7e−19); EMG1-ZNF384(3e−05); GAPDH-ZNF384(3e−04); GNB3-IFFO1(5e−06); GNB3-ING4(9e−06); GNB3-SCARNA12(3e−05); GNB3-ZNF384(3e−04); GPR162-PHB2(3e−05); GPR162-ZNF384(5e−06); IFFO1-ING4(3e−06); IFFO1-LEPREL2(2e−08); IFFO1-MLF2(2e−06); IFFO1-USP5(2e−08); ING4-LEPREL2(7e−19); ING4- | | | | |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Overall Rank | significance | Pairs gaining correlation (Significance) | Pairs losing correlation (significance) | Upregulated genes (fold change, distance to lost boundary) | Chr | Boundaries lost |
|---|---|---|---|---|---|---|
| | | LPCAT3(2e−13); ING4-LRRC23(3e−09); ING4-MLF2(2e−07); ING4-MRPL51(1e−06); ING4-NOP2(1e−05); ING4-PEX5(1e−05); ING4-RPL13P5(1e−05); ING4-SPSB2(4e−05); ING4-TAPBPL(4e−07); ING4-TNFRSF1A(2e−08); ING4-TPI1(5e−07); LEPREL2-LPCAT3(2e−08); LEPREL2-LRRC23(9e−20); LEPREL2-MRPL51(7e−11); LEPREL2-NCAPD2(5e−10); LEPREL2-NOP2(3e−13); LEPREL2-PEX5(2e−17); LEPREL2-PHB2(4e−07); LEPREL2-RPL13P5(7e−13); LEPREL2-SPSB2(2e−22); LEPREL2-TNFRSF1A(1e−04); LEPREL2-USP5(3e−13); LEPREL2-ZNF384(1e−16); LPAR5-LTBR(8e−06); LPCAT3-MLF2(2e−24); LPCAT3-PTMS(4e−05); LPCAT3-USP5(6e−22); LPCAT3-ZNF384(2e−08); LRRC23-MLF2(1e−18); LRRC23-PTMS(2e−05); LRRC23-USP5(5e−13); LRRC23-ZNF384(4e−05); MLF2-MRPL51(2e−12); | | | | |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| | | MLF2-NCAPD2(2e-08); MLF2-NOP2(7e-12); MLF2-PEX5(8e-13); MLF2-PHB2(8e-07); MLF2-PTPN6(1e-05); MLF2-RPL13P5(4e-12); MLF2-SPSB2(8e-16); MLF2-TAPBPL(9e-11); MLF2-TNFRSF1A(3e-14); MLF2-USP5(5e-07); MLF2-ZNF384(7e-12); MRPL51-USP5(3e-11); NCAPD2-PTMS(2e-04); NCAPD2-USP5(5e-08); NOP2-PTMS(2e-04); NOP2-USP5(1e-12); PEX5-PTMS(9e-07); PEX5-USP5(4e-13); PEX5-ZNF384(1e-05); PHB2-USP5(2e-09); PTMS-RPL13P5(2e-06); RPL13P5-USP5(8e-10); SPSB2-USP5(5e-15); TAPBPL-USP5(1e-10); TAPBPL-ZNF384(2e-04); TNFRSF1A-USP5(4e-12); TPI1-ZNF384(7e-07) | | | | |
| 4 | 1.00E-32 | BUB1B-RAD51(6e-28); DISP2-DNAJC17(3e-07); DNAJC17-RTF1(1e-06); GCHFR-ITPKA(4e-07); GCHFR-PAK6(2e-09); | GCHFR-ZFYVE19(2e-05) | | 15 | 40820000; 41660000; 40860000; 41190000 |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 5 | 8.00E−28 | GPR176-RAD51(3e−04) ARHGAP30-OLFML2B(4e−05); IGSF8-KLHDC9(4e−07); IGSF8-TSTD1(3e−12); KCNJ9-TSTD1(4e−09); KLHDC9-PCP4L1(7e−05); PCP4L1-TSTD1(2e−14); TOMM40L-TSTD1(4e−07) | F11R-KLHDC9(2e−06); F11R-NIT1(1e−04); F11R-TSTD1(5e−14); KLHDC9-UFC1(7e−10); TSTD1-USP21(2e−04) | KCNJ9(2.1-fold, 909 kb) | 1 | 160960000; 161130000 |
| 6 | 2.00E−24 | COX4I2-FOXS1(5e−05); COX4I2-MYLK2(4e−06) | BCL2L1-COX4I2(5e−19) | | 20 | 30380000 |
| 7 | 3.00E−22 | PDGFRA-SCFD2(7e−05) | CHIC2-PDGFRA(4e−18) | PDGFRA(3.7-fold, 315 kb) | 4 | 54780000 |
| 8 | 1.00E−20 | DIAPH1-PCDHGC4(2e−04); PCDHA1-PCDHGC3(4e−06); PCDHA1-PCDHGC4(2e−04); PCDHA1-TAF7(1e−04); PCDHB7-PCDHGA11(2e−04); PCDHGC4-SPRY4(4e−05) | PCDHGA1-PCDHGA2(2e−04); PCDHA1-PCDHGB1(6e−05); PCDHGA2-PCDHGA4(3e−05); PCDHA1-PCDHGA3-PCDHGA4(3e−04); PCDHGA3-PCDHGA5(3e−15); PCDHGA4-PCDHGA5(5e−05) | PCDHA1(2.3-fold, 524 kb) | 5 | 140690000; 140960000 |
| 9 | 7.00E−20 | CCDC106-ZNF542(7e−05); CCDC106-ZSCAN5A(8e−05); EPN1-HSPBP1(8e−06); EPN1-NAT14(9e−06); LENG8-SHISA7(1e−05); NAT14-TMEM86B(2e−04); SHISA7-ZNF542(3e−04); SHISA7-ZNF582(6e−08); SHISA7-ZNF583(1e−04); SHISA7-ZNF784(4e−05); UBE2S-ZSCAN5A(2e−04) | BRSK1-SHISA7(6e−05); BRSK1-TNNT1(2e−08); CCDC106-TNNT1(2e−04); PPP1R12C-TNNT1(7e−06); SYT5-TNNT1(1e−12) | SHISA7(3.6-fold, 25.8 kb) | 19 | 55600000; 56170000; 55610000; 55980000 |
| 10 | 5.00E−19 | ABHD1-DPYSL5(2e−04); ASXL2-KCNK3(1e−04); CAD-KCNK3(3e−04); GTF3C2-KCNK3(2e−07); | KCNK3-MAPRE3(2e−09) | KCNK3(5.8-fold, 286 kb) | 2 | 26630000; 27260000 |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 11 | 3.00E−18 | HADHA-KCNK3(2e−10); KCNK3-MPV17(4e−05); KCNK3-ZNF512(1e−06); KCNK3-ZNF513(4e−06); SLC5A6-TMEM214(3e−05) FAM178A-TLX1(5e−05) | DPCD-KAZALD1(6e−14); DPCD-POLL(3e−10) | | 10 | 102800000 |
| 12 | 3.00E−17 | ANKHD1-PCDHA1(5e−05); DIAPH1-PCDHA1(1e−04); IK-PCDHA1(3e−04); NRG2-PCDHA1(8e−08); PCDHA1-PCDHGC3(4e−06); PCDHA1-PCDHGC4(2e−04); PCDHA1-SLC35A4(6e−05); PCDHA1-TAF7(1e−04); PCDHA1-WDR55(5e−10); PCDHB7-PCDHGA11(2e−04) | PCDHB12-PCDHB13(1e−04); PCDHB13-PCDHB8(7e−08); PCDHB14-PCDHB8(2e−04); PCDHB16-PCDHB7(3e−04) | PCDHA1(2.3-fold, 45.9 kb) | 5 | 140120000; 140690000 |
| 13 | 4.00E−17 | APBA3-FSD1(2e−04); APBA3-SEMA6B(6e−05); ATCAY-C19orf71(3e−05); ATCAY-CCDC94(5e−11); ATCAY-DPP9(3e−04); ATCAY-FEM1A(3e−11); ATCAY-GNA11(7e−05); ATCAY-NCLN(2e−04); ATCAY-PIAS4(5e−06); ATCAY-SH3GL1(3e−07); ATCAY-ZNF57(5e−10); ATCAY-ZNF77(3e−05); CCDC94-ZFR2(6e−09); FEM1A-ZFR2(1e−06); FSD1-SIRT6(2e−04); | ANKRD24-MATK(6e−05); ATCAY-MATK(1e−06); MAP2K2-MRPL54(9e−05); MATK-ZFR2(2e−05) | ATCAY(4-fold, 89.4 kb); SEMA6B(3-fold, 320 kb) | 19 | 3650000; 4240000; 3720000; 3970000 |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 14 | 4.00E−17 | NCLN-ZFR2(2e−04); PIAS4-SEMA6B(9e−05); PIAS4-ZFR2(2e−04); SEMA6B-SIRT6(1e−04); ZFR2-ZNF57(3e−05); AK2-YARS(1e−05); BSDC1-KPNA6(2e−05); BSDC1-PHC2(1e−06); BSDC1-TXLNA(2e−04); CSMD2-S100PBP(1e−07); EIF31-YARS(1e−06); FAM167B-SYNC(1e−04); HPCA-KIAA1522(1e−12); PHC2-RBBP4(2e−06); PHC2-S100PBP(5e−05); PHC2-YARS(6e−05); TXLNA-YARS(4e−05) | RBBP4-ZBTB8A(5e−05) | | 1 | 32860000; 33320000 |
| 15 | 6.00E−17 | MDM2-RAB3IP(5e−05); RAB3IP-SLC35E3(3e−04) | MDM2-SLC35E3(1e−12) | RAB3IP(2-fold, 893 kb) | 12 | 69240000 |
| 16 | 1.00E−16 | RGN-SYN1(2e−10) | RGN-RP2(5e−07) | SYN1(2.8-fold,489kb) | X | 46990000; 46970000 |
| 17 | 2.00E−16 | CDK5R2-TTLL4(4e−05); CYP27A1-DNAJB2(4e−05); FAM134A-TTLL4(5e−05); PTPRN-TTLL4(6e−05) | CDK5R2-TUBA4A(3e−07); DNAJB2-FAM134A(3e−05); PTPRN-TUBA4A(5e−12) | CDK5R2(2.6-fold, 4.35 kb); PTPRN(2.9-fold, 144 kb) | 2 | 219820000; 220030000 |
| 18 | 4.00E−16 | HIPK1-MAGI3(3e−04); HIPK1-SYT6(2e−08) | HIPK1-PHTF1(2e−08) | SYT6(2.1-fold, 175 kb) | 1 | 114270000; 114520000 |
| 19 | 5.00E−16 | RAB21-TBC1D15(1e−08); TBC1D15-TMEM19(9e−05) | RAB21-THAP2(7e−08); RAB21-TMEM19(4e−05); THAP2-TMEM19(3e−08); TMEM19-ZFC3H1(2e−04) | | 12 | 72150000 |
| 20 | 2.00E−15 | ANKHD1-PCDHA1(5e−05); IK-PCDHA1(3e−04); | CD14-HBEGF(3e−06) | PCDHA1(2.3-fold, 65.9 kb) | 5 | 140100000 |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 21 | 2.00E−15 | PCDHA1-SLC35A4(6e−05); PCDHA1-WDR55(5e−10); C16orf89-VASN(6e−05); HMOX2-VASN(7e−05); NAGPA-VASN(6e−10) | GLIS2-VASN(2e−06) | | 16 | 4460000; 4460000 |
| 22 | 4.00E−15 | C16orf58-PRSS53(1e−06); C16orf93-STX1B(6e−05); GDPD3-PRSS53(5e−10); PHKG2-PRSS53(1e−04) | PRSS53-VKORC1(9e−06) | STX1B(2.2-fold, 61.8 kb) | 16 | 30960000; 31200000 |
| 23 | 5.00E−15 | CHRNB2-CREB3L4(5e−10); PBXIP1-RAB13(1e−05) | CREB3L4-RAB13(2e−04); CREB3L4-SLC39A1(1e−05) | CHRNB2(2.8-fold, 580 kb) | 1 | 153960000 |
| 24 | 9.00E−15 | NNAT-VSTM2L(3e−11) | NNAT-SRC(3e−04) | | 20 | 36180000 |
| 25 | 1.00E−14 | KHNYN-STXBP6(2e−04); MYH7-RABGGTA(2e−05) | CIDEB-LTB4R(9e−05); IRF9-RNF31(7e−06); KHNYN-RNF31(6e−06); KHNYN-SDR39U1(2e−06); KHNYN-TINF2(4e−10); KHNYN-TM9SF1(9e−05); KHNYN-TSSK4(3e−05) | MYH7(2.7-fold, 675 kb) | 14 | 24580000; 24920000 |
| 26 | 1.00E−14 | CCDC61-EML2(2e−04); CCDC8-EML2(8e−09); CCDC8-RTN2(5e−10); OPA3-PNMAL1(5e−05) | GPR4-VASP(2e−05) | | 19 | 46200000 |
| 27 | 1.00E−14 | ABHD1-DPYSL5(2e−04); AGBL5-SLC5A6(9e−05); CAD-KCNK3(3e−04); CGREF1-GTF3C2(2e−05); CGREF1-HADHA(7e−05); CGREF1-ZNF513(4e−05); EPT1-SLC5A6(6e−05); GPN1-SLC5A6(5e−05); KCNK3-MPV17(4e−05); | CGREF1-SLC30A3(3e−08) | CGREF1(2.5-fold, 41.8 kb); KCNK3(5.8-fold, 384 kb) | 2 | 27300000; 27550000 |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 28 | 2.00E−14 | SLC4A1AP-SLC5A6(2e−05); SLC5A6-SUPT7L(5e−07); SLC5A6-TMEM214(3e−05) CHMP2A-ZNF329(4e−06); MZF1-ZSCAN1(2e−04); SLC27A5-ZSCAN1(2e−04); SLC27A5-ZSCAN18(1e−04); TRAPPC2P1-ZNF329(3e−06); TRAPPC2P1-ZSCAN18(4e−05); UBE2M-ZNF256(1e−04); UBE2M-ZNF274(1e−04); UBE2M-ZNF329(1e−05); UBE2M-ZNF544(3e−05); UBE2M-ZNF776(6e−05); UBE2M-ZSCAN18(5e−10); ZBTB45-ZNF329(1e−04); ZBTB45-ZSCAN1(2e−04); ZBTB45-ZSCAN18(2e−05); ZIK1-ZNF329(1e−04); ZNF132-ZNF329(6e−05); ZNF134-ZNF329(2e−05); ZNF135-ZNF154(4e−05); ZNF135-ZNF211(1e−04); ZNF135-ZNF587(5e−05); ZNF17-ZNF329(6e−07); ZNF211-ZNF329(4e−07); ZNF211-ZSCAN1(8e−05); ZNF256-ZNF329(1e−05); ZNF264-ZNF329(3e−05); ZNF274-ZNF584(8e−05); ZNF304-ZNF329(4e−06); ZNF324-ZNF329(7e−06); | ZNF135-ZSCAN1(3e−05) | | 19 | 57900000; 58790000; 58460000; 58690000 |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| | | ZNF324B-ZNF329(1e−05); ZNF329-ZNF416(9e−08); ZNF329-ZNF419(4e−07); ZNF329-ZNF446(3e−05); ZNF329-ZNF530(2e−05); ZNF329-ZNF544(7e−06); ZNF329-ZNF549(2e−04); ZNF329-ZNF584(6e−08); ZNF329-ZNF671(6e−06); ZNF329-ZNF749(8e−05); ZNF329-ZNF773(5e−09); ZNF329-ZNF776(2e−09); ZNF329-ZNF8(2e−04); ZNF329-ZNF805(8e−07); ZNF329-ZNF814(2e−06); ZNF329-ZSCAN22(5e−05); ZNF419-ZSCAN1(2e−04); ZNF547-ZSCAN18(2e−04) | | | | |
| 29 | 2.00E−14 | GPN1-SLC5A6(5e−05); KCNK3-ZNF512(1e−06); SLC4A1AP-SLC5A6(2e−05); SLC5A6-SUPT7L(5e−07) | CCDC121-IFT172(5e−08); IFT172-PPM1G(5e−05) | KCNK3(5.8-fold, 694 kb) | 2 | 27610000 |
| 30 | 3.00E−14 | APOL2-CSF2RB(1e−04); CACNG2-EIF3D(2e−04); CACNG2-FOXRED2(9e−10); CACNG2-GGA1(9e−06); CACNG2-NOL12(4e−06); CACNG2-TRIOBP(4e−06); CACNG2-TXN2(1e−07) | CACNG2-PVALB(3e−05) | CACNG2(6.8-fold, 169 kb) | 22 | 36930000; 37410000 |
| 31 | 4.00E−14 | DISP2-DNAJC17(3e−07); DNAJC17-RTF1(1e−06); GCHFR-ITPKA(4e−07); | GCHFR-ZFYVE19(2e−05) | | 15 | 41020000; 41190000 |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 32 | 8.00E−14 | GCHFR-PAK6(2e−09); CACNA1A-WDR83(4e−05); CACNA1A-ZNF44(2e−06); CACNA1A-ZNF442(1e−07); CACNA1A-ZNF443(9e−06); CACNA1A-ZNF490(3e−07); CACNA1A-ZNF564(2e−06); CACNA1A-ZNF709(3e−06); CACNA1A-ZNF791(2e−05); CACNA1A-ZNF799(2e−05); MAST1-WDR83(2e−04); MAST1-ZNF136(4e−05); MAST1-ZNF433(2e−06); MAST1-ZNF44(4e−05); MAST1-ZNF442(7e−05); MAST1-ZNF490(9e−06); MAST1-ZNF563(1e−05); MAST1-ZNF564(6e−05); MAST1-ZNF625(7e−06); MAST1-ZNF700(1e−07); MAST1-ZNF844(1e−04) | ZNF433-ZNF823(8e−07); ZNF439-ZNF443(2e−04); ZNF439-ZNF799(2e−04); ZNF439-ZNF823(4e−05); ZNF44-ZNF823(2e−04); ZNF440-ZNF788(2e−04); ZNF440-ZNF823(1e−06); ZNF441-ZNF788(4e−05); ZNF442-ZNF788(2e−06); ZNF442-ZNF823(1e−05); ZNF564-ZNF823(1e−04); ZNF788-ZNF823(3e−06); ZNF823-ZNF844(2e−04) | MAST1(3.2-fold, 159 kb) | 19 | 12790000 |
| 33 | 9.00E−14 | PAFAH2-TMEM57(2e−04); PDIK1L-TMEM57(2e−05); SH3BGRL3-TMEM50A(4e−06) | LDLRAP1-TMEM57(2e−08) | | 1 | 26150000 |
| 34 | 1.00E−13 | C2-HCP5(3e−08) | MICA-TCF19(5e−06) | | 6 | 31460000 |
| 35 | 2.00E−13 | C16orf89-VASN(6e−05); HMOX2-VASN(7e−05); NAGPA-VASN(6e−10) | ALG1-NUDT16L1(3e−04) | | 16 | 4530000; 4740000 |
| 36 | 2.00E−13 | GABARAPL1-MAGOHB(5e−06) | KLRC2-KLRK1(5e−08) | | 12 | 10380000 |
| 37 | 2.00E−13 | DLX1-RAPGEF4(4e−07) | DLX1-HAT1(5e−07) | RAPGEF4(3-fold, 686 kb) | 2 | 173000000 |
| 38 | 2.00E−13 | ASPHD1-NFATC2IP(1e−05); ASPHD1-ZNF747(2e−04); | ASPHD1-DOC2A(6e−05); DOC2A-SEZ6L2(2e−04) | | 16 | 29820000; 30040000 |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| | | ASPHD1-ZNF785(1e−04); C16orf93-DOC2A(1e−04); C16orf93-PRRT2(2e−04); DCTPP1-SEZ6L2(2e−04); LAT-SEZ6L2(2e−04); NFATC2IP-SEZ6L2(4e−09); SEZ6L2-SPNS1(6e−06); SEZ6L2-SRCAP(1e−04); SEZ6L2-TBX6(9e−05); SEZ6L2-ZNF747(2e−04); SEZ6L2-ZNF764(3e−05); SEZ6L2-ZNF785(1e−05) | | | | |
| 39 | 2.00E−13 | ACP2-KBTBD4(1e−05); AMBRA1-NR1H3(1e−04); ARFGAP2-ARHGAP1(6e−07); ARFGAP2-KBTBD4(2e−05); ARFGAP2-MDK(2e−04); ARFGAP2-MTCH2(2e−04); ARFGAP2-NUP160(2e−04); ARFGAP2-PTPMT1(3e−05); ARFGAP2-PTPRJ(7e−05); ARFGAP2-ZNF408(3e−04); ARHGAP1-MADD(1e−04); C11orf49-NR1H3(3e−05); CHRM4-NR1H3(1e−04); FNBP4-MADD(2e−04); KBTBD4-MADD(2e−04); LRP4-NR1H3(2e−06); MADD-MDK(6e−06); MADD-NUP160(4e−06); MADD-SLC39A13(3e−05); MADD-ZNF408(4e−07); | NR1H3-SPI1(7e−07) | CHRM4(2.7-fold, 782 kb) | 11 | 47190000; 47430000 |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 40 | 3.00E−13 | NDUFS3-NR1H3(2e−04) CENPT-FBXL8(2e−04); CENPT-HSF4(3e−06); CENPT-KIAA0895L(8e−05); E2F4-FAM65A(1e−04); KIAA0895L-SLC12A4(2e−04); KIAA0895L-TSNAXIP1(4e−05); LRRC29-PARD6A(1e−04); PARD6A-TMEM208(1e−04); RLTPR-TPPP3(2e−04) | ATP6V0D1-SLC9A5(1e−07); NOL3-RRAD(7e−06); TPPP3-ZDHHC1(2e−04) | | 16 | 67510000 |
| 41 | 8.00E−13 | CCAR1-DNAJC12(5e−08) | DDX50-TET1(1e−04); SLC25A16-STOX1(1e−05); STOX1-TET1(2e−04) | DNAJC12(2.4-fold, 542 kb) | 10 | 70140000 |
| 42 | 8.00E−13 | AMT-CELSR3(4e−07); CELSR3-TCTA(2e−04); DAG1-IP6K1(2e−04); IP6K1-USP19(2e−04); IP6K1-USP4(2e−04); KLHDC8B-RHOA(1e−04) | AMT-RHOA(7e−05); CCDC71-RHOA(4e−05); LAMB2-TCTA(1e−04); RHOA-TCTA(2e−06) | CELSR3(2.9-fold, 440 kb) | 3 | 49140000; 49520000; 49340000; 49510000 |
| 43 | 8.00E−13 | CHRNB2-SLC27A3(3e−05); S100A2-TPM3(2e−04); S100A3-TPM3(1e−06); S100A6-TPM3(7e−05) | S100A13-S100A2(6e−07); S100A13-S100A6(2e−04); S100A13-SNAPIN(5e−05) | CHRNB2(2.8-fold, 790 kb) | 1 | 153750000; 153630000 |
| 44 | 9.00E−13 | CELF3-SETDB1(2e−05); ECM1-SV2A(3e−04); MLLT11-TARS2(5e−05); PRPF3-SEMA6C(5e−05); PRPF3-SV2A(2e−04); SEMA6C-SETDB1(1e−08); SEMA6C-TARS2(2e−05); SETDB1-TDRKH(1e−05) | CTSK-CTSS(8e−05); CTSK-MCL1(8e−05) | CELF3(3.5-fold, 709 kb); MLLT11(2.1-fold, 59.7 kb) | 1 | 150280000; 150980000; 150530000; 150970000 |
| 45 | 1.00E−12 | C1orf56-CELF3(3e−05); | C1orf56-PRUNE(1e−04) | CELF3(3.5-fold, 529 kb); | 1 | 150980000; 151160000 |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| | | CELF3-SEMA6C(2e−05); GABPB2-SNX27(1e−04); MLLT11-MRPS21(1e−04); MLLT11-PI4KB(2e−04); MLLT11-RFX5(1e−06); MLLT11-TARS2(5e−05); MRPL9-SEMA6C(4e−05); PI4KB-SEMA6C(1e−04); POGZ-SEMA6C(1e−05); PRPF3-SEMA6C(5e−05); RFX5-SEMA6C(2e−04); SEMA6C-SETDB1(1e−08); SEMA6C-SNX27(1e−05); SEMA6C-TARS2(2e−05); SEMA6C-TDRKH(4e−08); SEMA6C-VPS72(8e−09) | | MLLT11(2.1-fold, 59.7 kb) | | |
| 46 | 1.00E−12 | CD33-PPP2R1A(1e−04); ZNF320-ZNF468(2e−05); ZNF468-ZNF480(2e−04); ZNF468-ZNF616(2e−06); ZNF468-ZNF701(3e−08); ZNF528-ZNF766(1e−05); ZNF701-ZNF808(2e−05) | ZNF28-ZNF468(1e−08); | | 19 | 52630000 |
| 47 | 2.00E−12 | HERC1-TRIP4(2e−05) | CSNK1G1-TRIP4(7e−08); KIAA0101-TRIP4(3e−07) | | 15 | 64460000 |
| 48 | 2.00E−12 | CDH24-EFS(4e−05); CDH24-MYH7(3e−07); HAUS4-JPH4(1e−04) | ACIN1-C14orf119(6e−06) | EFS(2.4-fold, 255 kb); MYH7(2.7-fold, 325 kb); JPH4(3.8-fold, 468 kb) | 14 | 23580000 |
| 49 | 2.00E−12 | C19orf57-CACNA1A(4e−05); CACNA1A-RFX1(8e−07); CACNA1A-SAMD1(3e−04); CC2D1A-CCDC130(2e−04); | CC2D1A-IL27RA(3e−06); IL27RA-PALM3(3e−05) | | 19 | 13970000; 14620000; 13980000; 14230000 |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 50 | 3.00E-12 | LPHN1-RFX1(2e-05); LPHN1-ZNF333(4e-06) EPN1-HSPBP1(8e-06); LENG8-SHISA7(1e-05); SHISA7-ZNF542(3e-04); SHISA7-ZNF582(6e-08); SHISA7-ZNF583(1e-04); SHISA7-ZNF784(4e-05); UBE2S-ZSCAN5A(2e-04) | BRSK1-SHISA7(6e-05) | SHISA7(3.6-fold, 5.77 kb) | 19 | 55790000; 55960000 |
| 51 | 3.00E-12 | AQP6-SPATS2(2e-06); DDX23-SPATS2(2e-05) | MCRS1-TROAP(1e-06) | | 12 | 49690000; 49980000 |
| 52 | 4.00E-12 | BMP8B-PPIE(9e-05); MYCBP-PABPC4(7e-05); PABPC4-SMAP2(3e-07); PPIE-SMAP2(4e-05) | HEYL-PABPC4(1e-05) | | 1 | 40040000; 40220000 |
| 53 | 5.00E-12 | IFT46-RNF26(5e-07); MFRP-TRAPPC4(1e-06) | H2AFX-HMBS(1e-05) | | 11 | 118930000; 118930000; 119210000 |
| 54 | 5.00E-12 | C2-PSMB8(3e-04); C2-PSMB9(1e-06); C2-TAP1(2e-06); COL11A2-RGL2(1e-04); TAP1-TAP2(6e-06) | RING1-RPS18(4e-06) | 33240000 | 6 | 32810000; |
| 55 | 6.00E-12 | CDH22-SNX21(1e-06); SLC35C2-ZNF334(5e-05) | ELMO2-ZNF334(6e-06); | CDH22(2.4-fold, 327 kb) | 20 | 44610000 |
| 56 | 9.00E-12 | ARL4D-G6PC3(4e-05); ARL4D-NAGS(3e-04); HDAC5-SLC25A39(4e-05); IFI35-MPP2(2e-04); MPP3-TMUB2(4e-08) | HDAC5-MPP2(2e-04) | 42270000 | 17 | 41940000; |
| 57 | 1.00E-11 | AGAP3-LRRC61(2e-05); AGAP3-RARRES2(8e-05); CDK5-LRRC61(8e-07) | LRRC61-REPIN1(3e-04); RARRES2-REPIN1(1e-05) | | 7 | 150150000 |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 58 | 1.00E−11 | C16orf70-TPPP3(1e−04); E2F4-SLC9A5(3e−04); RLTPR-TPPP3(2e−04) | ATP6V0D1-SLC9A5(1e−07); TPPP3-ZDHHC1(2e−04) | | 16 | 67270000; 67510000 |
| 59 | 1.00E−11 | BAIAP2L2-GGA1(3e−04); CACNG2-GGA1(9e−06); CACNG2-NOL12(4e−06); CACNG2-TRIOBP(4e−06); ELFN2-TRIOBP(3e−06); KCNJ4-LGALS1(2e−04) | GGA1-LGALS1(5e−05); LGALS1-TRIOBP(4e−06) | CACNG2(6.8-fold, 901 kb); ELFN2(3.9-fold, 228 kb) | 22 | 38000000; 38200000 |
| 60 | 2.00E−11 | C16orf70-TPPP3(1e−04); CENPT-FBXL8(2e−04); CENPT-HSF4(3e−06); CENPT-KIAA0895L(8e−05); E2F4-FAM65A(1e−04); E2F4-SLC9A5(3e−04); KIAA0895L-LRRC29(2e−04); KIAA0895L-SLC12A4(2e−04); KIAA0895L-TSNAXIP1(4e−05) | NOL3-RRAD(7e−06) | | 16 | 67230000 |
| 61 | 2.00E−11 | MAST1-ZNF433(2e−06); MAST1-ZNF625(7e−06); MAST1-ZNF700(1e−07); MAST1-ZNF844(1e−04) | ZNF440-ZNF788(2e−04) | MAST1(3.2-fold, 679 kb) | 19 | 12270000 |
| 62 | 2.00E−11 | AMIGO1-AMPD2(2e−06); AMIGO1-GSTM5(2e−04); AMPD2-CELSR2(2e−07); AMPD2-CLCC1(4e−06); AMPD2-KCNC4(7e−06); AMPD2-KIAA1324(3e−05); AMPD2-SARS(3e−04); AMPD2-TAF13(2e−04); AMPD2-WDR47(8e−07); CELSR2-GSTM5(3e−05); | GSTM2-GSTM5(1e−04) | | 1 | 110080000; 110320000 |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
|  |  | GNAI3-SARS(2e−06); GSTM4-SARS(6e−06); GSTM5-KCNA2(1e−05); GSTM5-KCNC4(1e−05); GSTM5-KIAA1324(1e−04); GSTM5-SLC6A17(1e−05); GSTM5-SORT1(5e−05) |  |  |  |  |
| 63 | 3.00E−11 | CHD3-PLSCR3(1e−05); DVL2-NLGN2(2e−04); KDM6B-NLGN2(2e−05); NEURL4-SLC25A35(9e−05) | FGF11-TMEM102(3e−06) |  | 17 | 7220000; 7480000 |
| 64 | 3.00E−11 | BCORL1-OCRL(1e−05); RAB33A-RBMX2(6e−05) | ELF4-UTP14A(3e−06) | RAB33A(3.1-fold, 54.2 kb) | X | 128700000; 129360000 |
| 65 | 5.00E−11 | AMT-CELSR3(4e−07); CELSR3-TCTA(2e−04) | CCDC51-PLXNB1(1e−04); PLXNB1-UOCRC1(2e−04) | CELSR3(2.9-fold, 19.7 kb) | 3 | 48720000 |
| 66 | 7.00E−11 | ANKMY1-MTERFD2(3e−04); ANKMY1-STK25(4e−06) | CAPN10-RNPEPL1(2e−05) |  | 2 | 241760000 |
| 67 | 8.00E−11 | AK1-PTGES2(5e−05); COQ4-LRSAM1(4e−07); NAIF1-STXBP1(2e−04); PTGES2-PTRH1(3e−07) | AK1-PTRH1(3e−04) |  | 9 | 130690000 |
| 68 | 8.00E−11 | PHC2-RBBP4(2e−06) | RBBP4-ZBTB8A(5e−05) |  | 1 | 33120000 |
| 69 | 9.00E−11 | LRRC34-SLC7A14(1e−04); MYNN-SLC7A14(2e−06) | GPR160-LRRC34(4e−05) | SLC7A14(3-fold, 494 kb) | 3 | 169810000 |
| 70 | 9.00E−11 | ARHGEF2-SMG5(5e−05); GBA-SLC25A44(3e−04) | C1orf85-LMNA(2e−06) |  | 1 | 156050000 |
| 71 | 9.00E−11 | C19orf12-CCNE1(9e−07); POP4-VSTM2B(1e−04) | PLEKHF1-POP4(1e−04) | VSTM2B(2.3-fold, 62.5 kb) | 19 | 30080000; 30220000 |
| 72 | 1.00E−10 | ARHGAP27-FZD2(2e−05); CCDC43-MPP3(3e−05); DBF4B-MPP3(6e−06); FMNL1-FZD2(1e−06); | ATXN7L3-RUNDC3A(1e−04) |  | 17 | 42270000; 42790000 |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 73 | 1.00E−10 | HDAC5-SLC25A39(4e−05) EHMT1-LCNL1(7e−05); GPSM1-MAMDC4(1e−05); INPP5E-LCNL1(2e−04) | C9orf142-EDF1(1e−05) | LCNL1(2.4-fold, 62.6 kb) | 9 | 139660000; 139940000 |
| 74 | 1.00E−10 | AVPI1-PYROXD2(6e−05) | EXOSC1-PI4K2A(1e−05); EXOSC1-ZFYVE27(2e−06) | | 10 | 99500000 |
| 75 | 2.00E−10 | BET1-CASD1(6e−05); BET1-PPP1R9A(8e−06) | PEG10-SGCE(2e−05) | | 7 | 94080000 |
| 76 | 2.00E−10 | NLGN3-PDZD11(1e−05) | GDPD2-IGBP1(1e−05); GDPD2-PDZD11(4e−05) | | X | 69660000 |
| 77 | 2.00E−10 | SEC23IP-SFXN4(3e−05) | RGS10-SFXN4(7e−06) | | 10 | 121310000 |
| 78 | 3.00E−10 | AFF3-MRPL30(1e−04) MITD1-REV1(5e−06) | LIPT1-MITD1(2e−06); | | 2 | 100150000 |
| 79 | 4.00E−10 | CEACAM19-ZNF404(2e−04); ZNF226-ZNF428(1e−05) | ZNF180-ZNF235(2e−04); ZNF180-ZNF45(9e−05); ZNF224-ZNF234(1e−04); ZNF234-ZNF284(3e−05) | | 19 | 44320000; 45050000 |
| 80 | 4.00E−10 | PHOSPHO2-UBR3(2e−04) | BBS5-SSB(3e−06); PHOSPHO2-SSB(1e−04) | | 2 | 170790000; 170670000 |
| 81 | 4.00E−10 | C2-MICB(6e−06); C4A-MICB(2e−04); IER3-TNF(7e−06) | AIF1-LTB(7e−05); MICB-NFKBIL1(3e−04) | | 6 | 31460000; 31610000 |
| 82 | 5.00E−10 | DMGDH-HOMER1(5e−06) | BHMT2-DMGDH(9e−05) | | 5 | 78470000 |
| 83 | 5.00E−10 | B3GNT1-EFEMP2(8e−05); C11orf68-SYVN1(1e−04); EFEMP2-KLC2(1e−05); EFEMP2-PELI3(2e−06); EFEMP2-PPP2R5B(1e−05); EFEMP2-SNX32(5e−05); EFEMP2-SPTBN2(1e−04); EFEMP2-TMEM151A(8e−05); FIBP-RBM4B(2e−05); FIBP- | DRAP1-FIBP(3e−04) | SPTBN2(2.4-fold, 669 kb) | 11 | 65390000; 65820000; 65630000; 65780000 |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
|  |  | SPTBN2(2e-04); FIBP-TIGD3(5e-05); GAL3ST3-TIGD3(1e-04); NRXN2-PCNXL3(1e-05); SF3B2-SPTBN2(2e-04) |  |  |  |  |
| 84 | 6.00E-10 | ABR-SERPINF1(7e-06); SERPINF1-SLC43A2(1e-04) | RPA1-SMYD4(9e-05) |  | 17 | 1560000; 1570000 |
| 85 | 7.00E-10 | MTMR3-OSBP2(2e-04); OSBP2-PISD(2e-05) | LIMK2-TUG1(3e-05) |  | 22 | 30900000; 31680000 |
| 86 | 8.00E-10 | ABHD14A-PARP3(7e-05); PARP3-PCBP4(2e-04) | ACY1-PPM1M(1e-05); GLYCTK-POC1A(3e-04); PCBP4-TWF2(2e-04) |  | 3 | 51990000 |
| 87 | 1.00E-09 | E124-PKNOX2(4e-06) | CCDC15-TMEM218(3e-04) |  | 11 | 125320000 |
| 88 | 1.00E-09 | ARHGEF2-SMG5(5e-05); DAP3-UBQLN4(8e-05) | GON4L-RIT1(1e-04); KIAA0907-RIT1(2e-05) |  | 1 | 155700000; 156040000 |
| 89 | 1.00E-09 | BET1-CASD1(6e-05) | PEG10-SGCE(2e-05) |  | 7 | 94120000 |
| 90 | 1.00E-09 | COX412-FOXS1(5e-05); COX412-MYLK2(4e-06) | PDRG1-TM9SF4(3e-04) |  | 20 | 30400000 |
| 91 | 1.00E-09 | ABCA17P-ZNF263(5e-06); ABCA3-ZNF200(1e-04); ABCA3-ZNF263(2e-04); PDPK1-ZNF597(2e-04) | ZNF263-ZNF75A(2e-04) |  | 16 | 3230000 |
| 92 | 1.00E-09 | HNRNPR-LYPLA2(1e-05); ID3-ZNF436(1e-04); LUZP1-TCEA3(1e-04); LYPLA2-ZNF436(5e-06); PNRC2-ZNF436(2e-05) | C1orf213-TCEA3(3e-04) | 23810000 | 1 | 23620000; |
| 93 | 1.00E-09 | CDKN2D-RAB3D(1e-04); ILF3-S1PR2(8e-05) | KRI1-QTRT1(1e-04); QTRT1-TMED1(2e-05) | 10980000 | 19 | 10520000; |
| 94 | 2.00E-09 | LHFPL4-TADA3(2e-04); SRGAP3-TADA3(5e-05) | ARPC4-TADA3(4e-05) |  | 3 | 9750000 |
| 95 | 2.00E-09 | CHRNB2-FLAD1(3e-04); EFNA1- | ADAM15-EFNA4(2e-04) | CHRNB2(2.8-fold, 370 kb) | 1 | 154910000; 155040000 |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| | | PYGO2(2e−04); PBXIP1-RAB13(1e−05) | | | | |
| 96 | 2.00E−09 | APBA1-PIP5K1B(3e−05) | FAM189A2-PTAR1(8e−05) | | 9 | 71990000 |
| 97 | 3.00E−09 | EIF3I-ZCCHC17(2e−05); TXLNA-ZCCHC17(2e−04) | NKAIN1-SERINC2(1e−04) | | 1 | 32030000 |
| 98 | 3.00E−09 | APBA3-SEMA6B(6e−05); CCDC94-SEMA6B(2e−05); FEM1A-SEMA6B(1e−05); KDM4B-SEMA6B(2e−04); PIAS4-SEMA6B(9e−05); SEMA6B-SH3GL1(2e−04); SEMA6B-SIRT6(1e−04) | SEMA6B-TNFAIP8L1(2e−04) | SEMA6B(3-fold, 59.8 kb) | 19 | 4500000; 4680000 |
| 99 | 3.00E−09 | CD33-PPP2R1A(1e−04) | ZNF350-ZNF613(1e−04); ZNF350-ZNF614(2e−05); ZNF613-ZNF614(2e−04) | | 19 | 52390000 |
| 100 | 3.00E−09 | NEK8-NLK(3e−04) | DHRS13-TRAF4(1e−05) | | 17 | 27050000 |
| 101 | 4.00E−09 | CHST6-CNTNAP4(4e−05) | CHST6-TMEM231(9e−05) | | 16 | 75660000 |
| 102 | 4.00E−09 | HDAC5-SLC25A39(4e−05) | ATXN7L3-RUNDC3A(1e−04) | | 17 | 42270000 |
| 103 | 4.00E−09 | PRODH-TUBA8(5e−05) | SLC25A1-UFD1L(7e−05) | | 22 | 18910000 |
| 104 | 5.00E−09 | HCFC1-L1CAM(1e−04) | L1CAM-PDZD4(3e−05) | L1CAM(6-fold, 83.6 kb) | X | 153220000 |
| 105 | 6.00E−09 | ADCY6-PFKM(7e−05); C12orf68-RHEBL1(2e−04);-CCNT1-PFKM(9e05); DDX23-PFKM(1e−04); LMBR1L-PFKM(6e−05); PFKM-PRKAG1(7e−05); PFKM-RPAP3(1e−04) | C12orf68-PFKM(9e−05) | | 12 | 48110000; 48590000; 48380000; 48590000 |
| 106 | 6.00E−09 | CDH3-HAS3(3e−04); COG8-SMPD3(3e−05); RANBP10-SMPD3(3e−04); SMPD3-TERF2(4e−05) | CDH3-SMPD3(2e−04) | SMPD3(2.3-fold, 92.4 kb) | 16 | 68390000; 69170000; 68390000; 68880000 |
| 107 | 6.00E−09 | BCAT2-RCN3(7e−05); CA11- | BAX-NUCB1(2e−04) | 49490000 | 19 | 49140000; |

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|
| 108 | 6.00E−09 | EMP3(3e−04); GRWD1-MAMSTR(6e−05); MED25-NUCB1(3e−05) CDK5R2-TTLL4(4e−05); CYP27A1-DNAJB2(4e−05); FAM134A-TTLL4(5e−05); PTPRN-TTLL4(6e−05); TMEM198-TTLL4(6e−05) | CYP27A1-TTLL4(2e−04) | CDK5R2(2.6-fold, 94.3 kb); PTPRN(2.9-fold, 444 kb) | 2 | 219730000 |
| 109 | 6.00E−09 | CDKN2D-RAB3D(1e−04) | ACP5-CNN1(1e−04); DOCK6-TMEM205(6e−05) | | 19 | 11330000 |
| 110 | 7.00E−09 | NEK8-NLK(3e−04); NLK-RAB34(1e−04); POLDIP2-UNC119(1e−04); TMEM199-UNC119(2e−04) | IFT20-TMEM199(7e−05) | | 17 | 26690000 |
| 111 | 8.00E−09 | NR1H2-VSIG10L(1e−04) | SIGLEC10-SIGLEC14(6e−05) | | 19 | 51790000 |
| 112 | 9.00E−09 | KDM4B-SEMA6B(2e−04) | PLIN3-UHRF1(6e−05) | SEMA6B(3-fold, 240 kb) | 19 | 4800000 |
| 113 | 1.00E−08 | C12orf10-CALCOCO1(4e−05) | PRR13-RARG(2e−04) | | 12 | 53910000 |
| 114 | 1.00E−08 | CYGB-RNF157(7e−05) | EXOC7-SRP68(2e−04); FBF1-FOXJ1(2e−04) | | 17 | 74430000 |
| 115 | 2.00E−08 | PALM-UQCR11(1e−04) | MBD3-UOCR11(2e−04) | | 19 | 1520000 |
| 116 | 2.00E−08 | MTMR3-OSBP2(2e−04) | ASCC2-UOCR10(1e−04); NF2-UQCR10(3e−04) | | 22 | 30490000 |
| 117 | 2.00E−08 | ACTR5-K1AA1755(3e−04); PPP1R16B-SNHG11(1e−04) | PPP1R16B-SLC32A1(2e−04) | | 20 | 37210000 |
| 118 | 3.00E−08 | ARHGEF11-PRCC(2e−04) | CRABP2-PEAR1(1e−04) | | 1 | 156910000 |
| 119 | 3.00E−08 | ACTR5-KIAA1755(3e−04); CTNNBL1-NDRG3(2e−04); PPP1R16B-SNHG11(1e−04) | NNAT-SRC(3e−04) | | 20 | 35820000; 37080000 |
| 120 | 4.00E−08 | BAIAP2L2-GGA1(3e−04); KCNJ4-LGALS1(2e−04) | KDELR3-MAFF(2e−04) | | 22 | 38390000 |
| 121 | 7.00E−08 | PAK2-TNK2(3e−04) | PAK2-PIGX(2e−04) | TN K2(2.4-fold, 687 kb) | 3 | 196300000 |
| 122 | 9.00E−08 | C19orf66-ICAM5(3e−04) | ICAM1-ICAM3(3e−04) | | 19 | 10370000 |

-continued

Supplementary Table 1. List of deregulated boundaries and genes. Table lists domain whose boundaries are predicted to be lost based on cross-boundary gene pairs that gain correlation and intra-domain gene pairs that lose correlation. All supporting gene pairs (FDR < 1%) are listed along with their significance. The overall significance of each domain is also shown. Genes that are up-regulated by at least 2-fold in IDH mutant gliomas, relative to the median of the wild-type, are indicated. For each domain, the coordinates of boundaries predicted to be lost are also listed.

| Overall Rank | Overall significance | Pairs gaining correlation (Significance) | Pairs losing correlation (significance) | Upregulated genes (fold change, distance to lost boundary) | Chr | Boundaries lost |
|---|---|---|---|---|---|---|

SE

Figure 3:
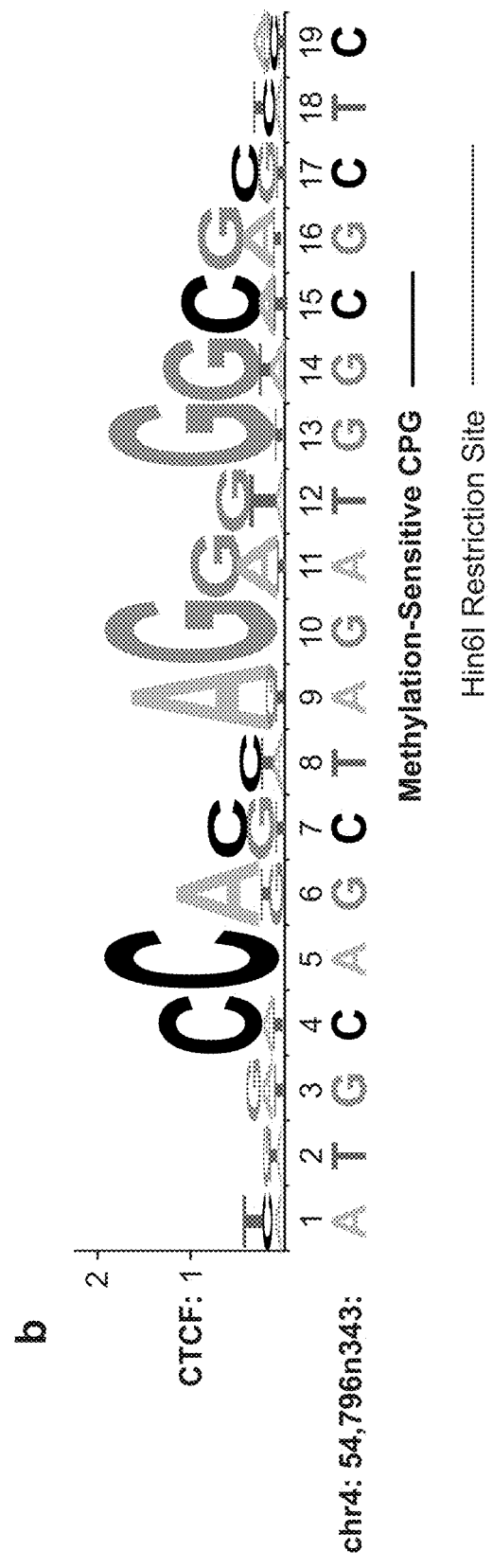
FIG. 3A-3K illustrates that insulator loss allows PDGFRA to interact with a constitutive enhancer. (a) Contact domain structure shown for a 1.7 MB region containing PDGFRA. Heat depicts HiC interaction scores between triangulated loci in IMR90 cells[15]. Domains are visible as triangle-shaped regions of high interaction scores. Convergent CTCF sites anchor a loop that separates PDGFRA and FIP1L (black circle). H3K27ac and CTCF profiles are aligned to the contact map. Interaction trace (below) depicts HiC signals between the PDGFRA promoter and all other positions in the region. Genes, FIP1L1 enhancer (per H3K27ac) and insulator (per HiC and CTCF binding) are indicated. (b) The right CTCF peak in the insulator contains a CTCF motif with a CpG at a methylation-sensitive position (SEQ ID NO: 1). (c,d) ChIP-qPCR data show that CTCF occupancy over the boundary is reduced in IDH mutant (red) gliomas and models, relative to wildtype (black). (e) Methylation levels of the CpG in the CTCF motif were measured in gliomaspheres by bisulfite sequencing, and plotted as percent of alleles protected from conversion. (f) Methylation levels of the CpG in the CTCF motif were measured in glioma specimens by methylation-sensitive restriction, and plotted as relative protection. (g) Expanded views of FIP1L1 enhancer locus and PDGFRA locus shown with H3K27ac tracks. Vertical black bars indicate the locations of the common PDGFRA promoter primer and four complementary primers tested in 3C. (h-k) Plots show normalized 3C interaction frequencies between PDGFRA promoter and indicated regions. A strong interaction between PDGFRA promoter and FIP1L1 enhancer is evident in IDH mutant tumors and models. (Error bars in all panels reflect standard deviations of triplicate observations).
Figure 3:
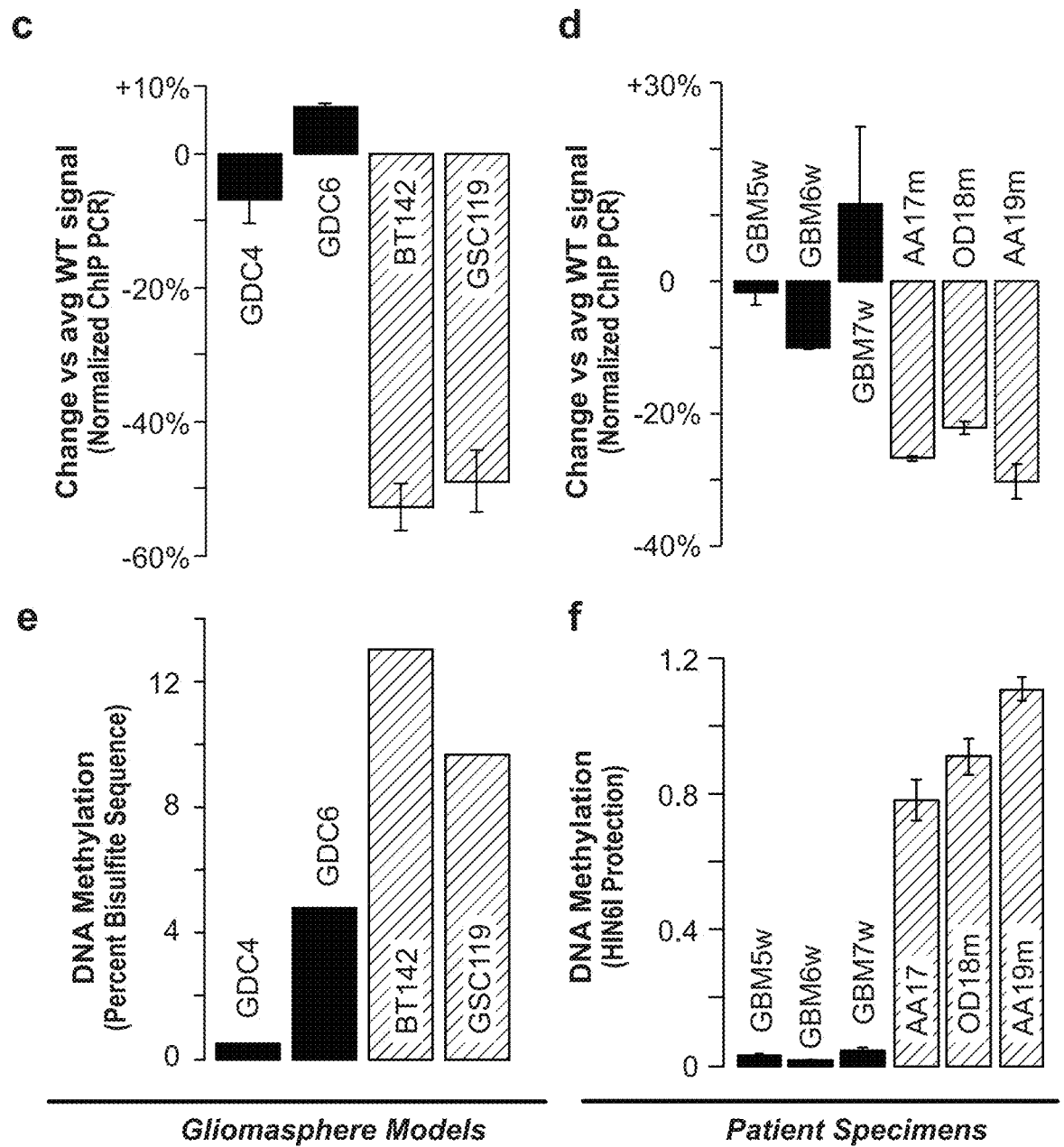
Figure 3:
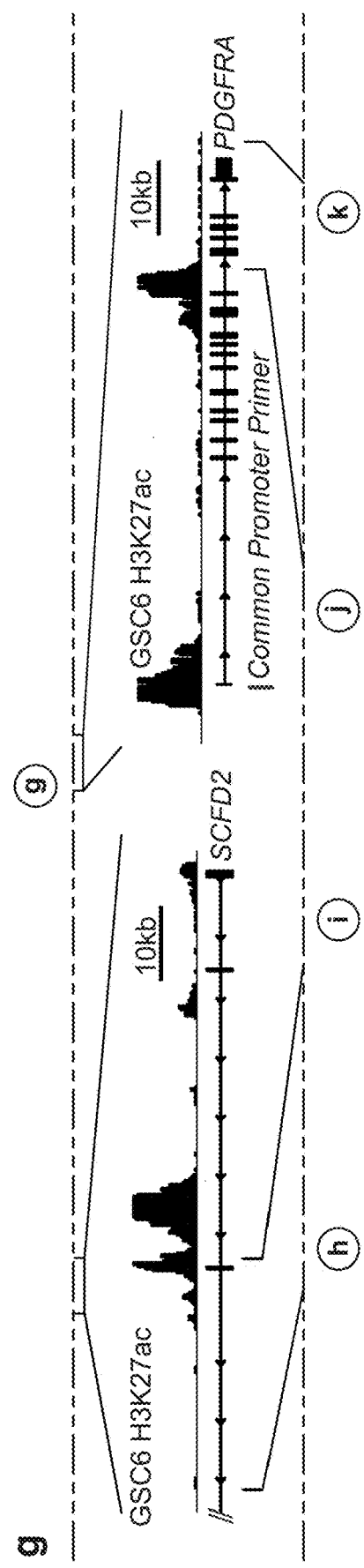
Figure 3:
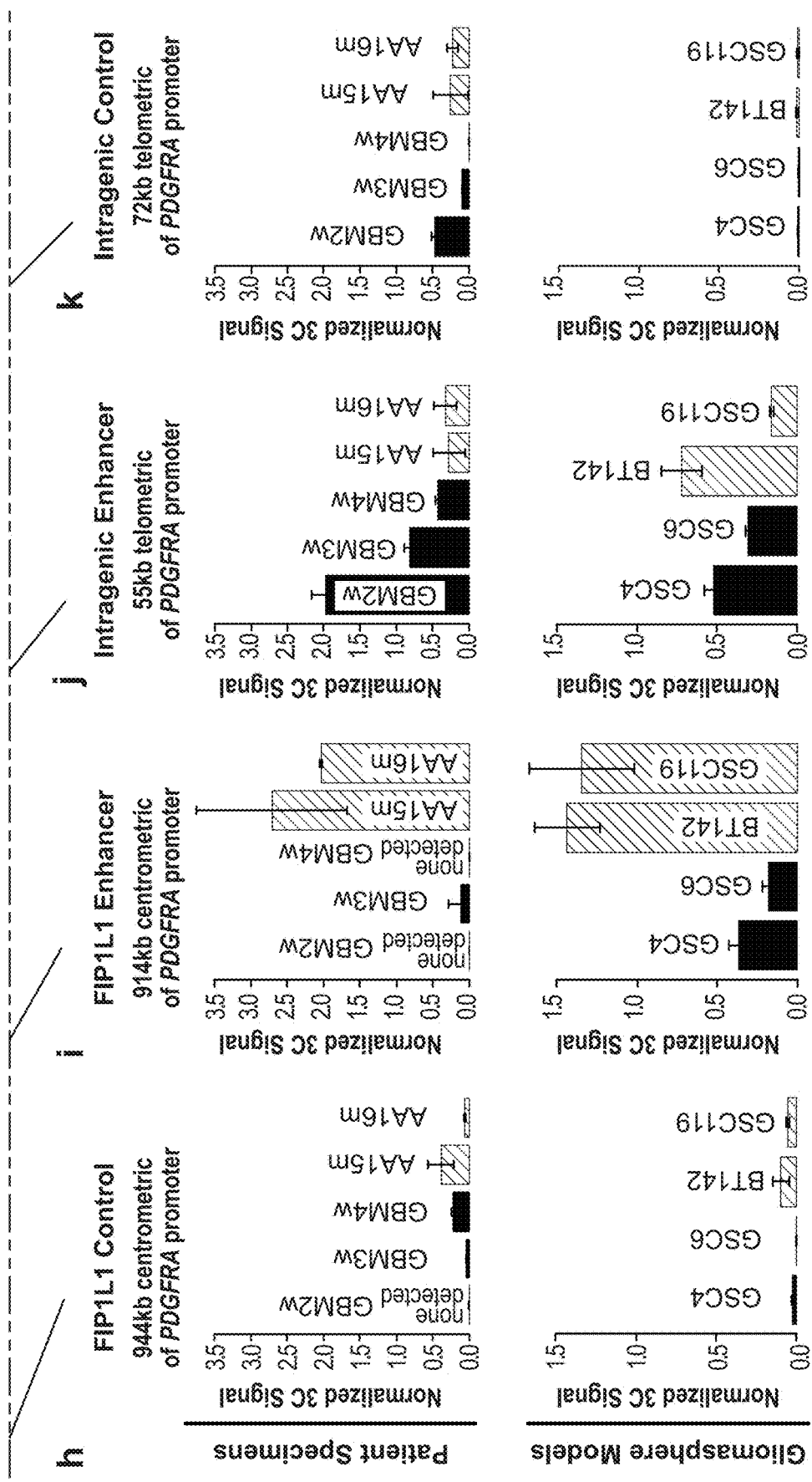
Figure 7:
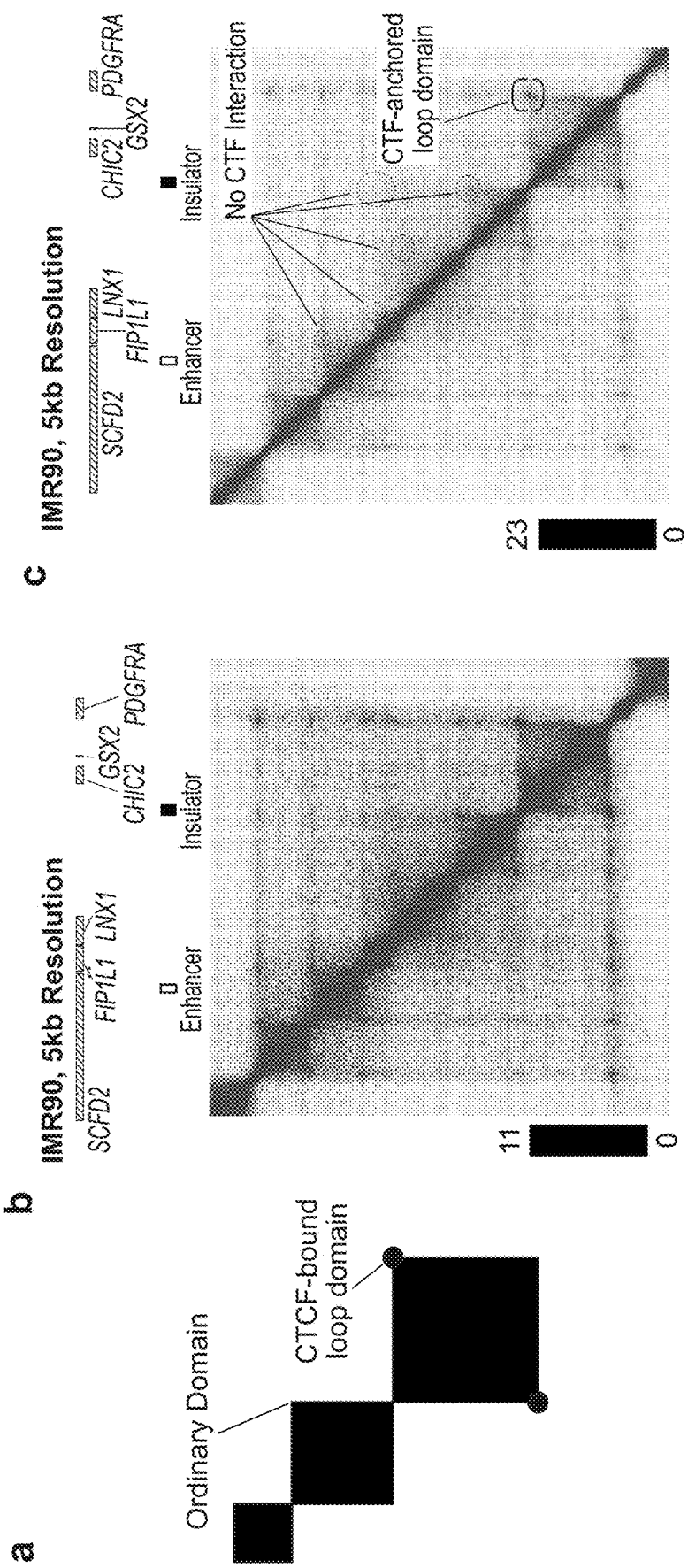
FIG. 7A-7E illustrates a CTCF anchored loop in the PDGFRA region. (a) Schematic depiction of a HiC interaction signature of a CTCF-anchored loop domain, compared to an ordinary domain, as described by Rao et al., *Cell* 2014. CTCF-anchored loop domains are characterized by an increased interaction score at the apex of the domain, representing a CTCF-CTCF dimeric interaction. (b) IMR90 HiC contact matrix for the PDGFRA/FIP1L1 locus, as presented in FIG. 3*a*. Solid circle indicates CTCF dimer interaction point. Dashed circles indicate lack of CTCF dimeric anchor signature. (c) IMR90 HiC contact matrix as in (b), but with expanded heatmap scale, more clearly conveys the CTCF-anchored loop that insulates PDGFRA. (d,e) HiC contact matrix for GM12878 cells for the same region confirms a single CTCF-anchored loop (solid circle) between PDGFRA and FIP1L1. These data support the significance of this specific boundary in locus topology and PDGFRA insulation.
Figure 7:
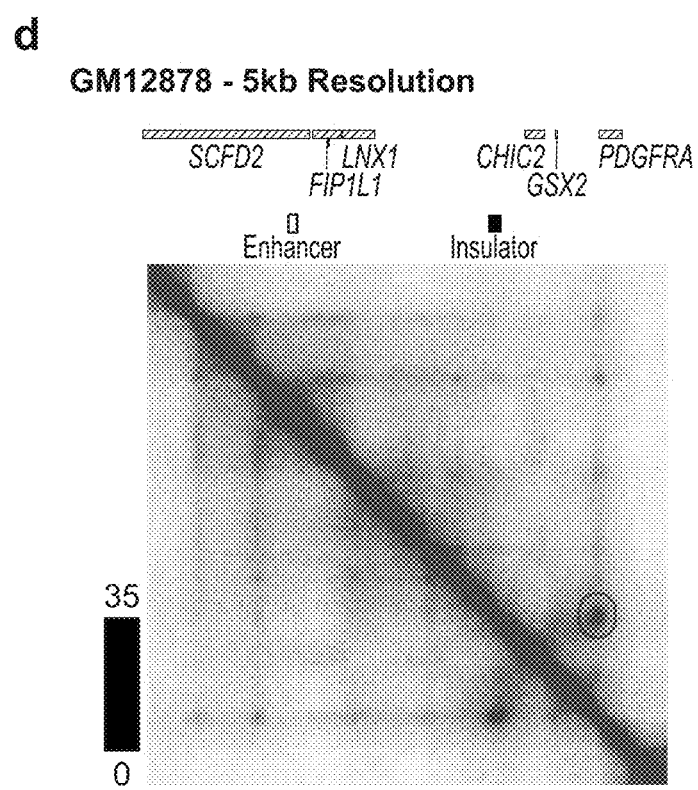
Figure 7:
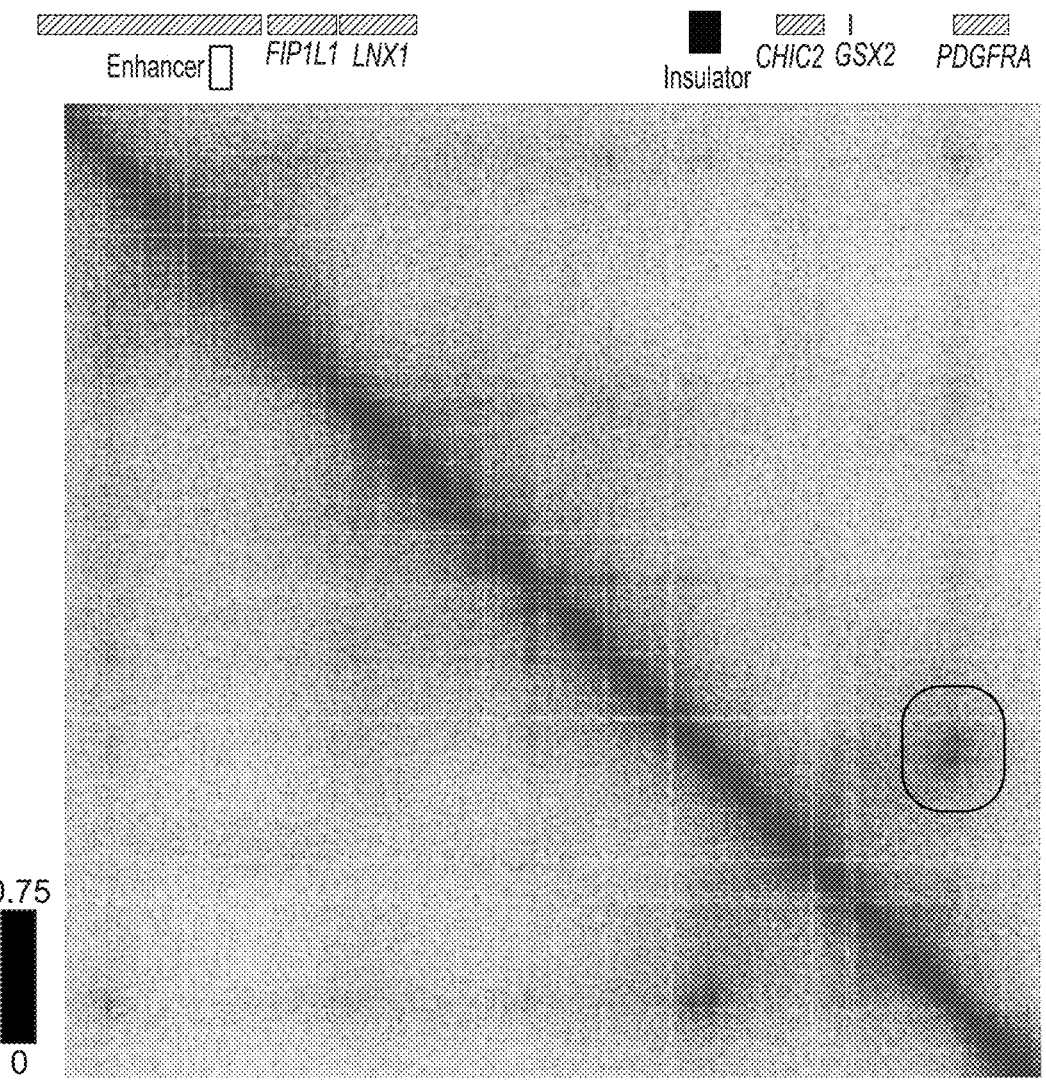

Example 3. Insulator Loss Allows PDGFRA to Interact with a Constitutive Enhancer Applicants therefore investigated the topology of the region using kilobase-resolution HiC data[15]. In all six cell types examined, PDGFRA and FIP1L1 reside in distinct domains, separated by one CTCF-anchored constitutive boundary (FIG. 3a, FIG. 7). Our ChIP-seq data confirm that this boundary contains a strong CTCF binding site over a canonical CTCF motif with a CpG dinucleotide in a position previously linked to methylation-sensitivity[25] (FIG. 3b). Quantitative ChIP-PCR reveals that CTCF occupancy at this site is reduced between 30% and 50% in IDH mutant tumors and gliomasphere models, relative to wildtype (FIG. 3c,d). Moreover, the CpG in this motif becomes highly methylated in IDH mutants (FIG. 3e,f). This suggests that reduced CTCF binding may compromise the boundary flanking PDGFRA in IDH mutant, hyper-methylated tumors.

To identify regulatory elements that might underlie PDGFRA induction, Applicants mapped the enhancer-associated histone modification, H3 lysine 27 acetylation (H3K27ac), in glioma specimens and models. Applicants identified a large enhancer ~50 kb upstream of FIP1L1 with strong acetylation in wildtype and mutant tumors (FIG. 3a; FIG. 8). In support of an enhancer identity, the element is enriched for H3 lysine 4 mono-methylation (H3K4me1), but lacks H3K4me3, and contains conserved motifs bound by the glioma master transcription factors, OLIG2 and SOX2. Although this enhancer is normally insulated from PDGFRA, Applicants reasoned that disruption of the intervening boundary might allow it to interact with the oncogene in IDH mutant gliomas. To test this, Applicants used chromosome conformation capture (3C) to query the relative frequencies with which the PDGFRA promoter interacts with the FIP1L1 enhancer, with an intragenic PDGFRA enhancer, or with nearby control sites (FIG. 3g). Applicants fixed IDH mutant and wildtype glioma specimens and gliomaspheres, digested their chromatin with HinDIII, and performed proximity ligation to re-ligate physically interacting DNA sequences. Applicants used qPCR to measure ligation frequencies between elements, normalizing against control ligations performed with bacterial artificial chromosome DNA.

Figure 9:
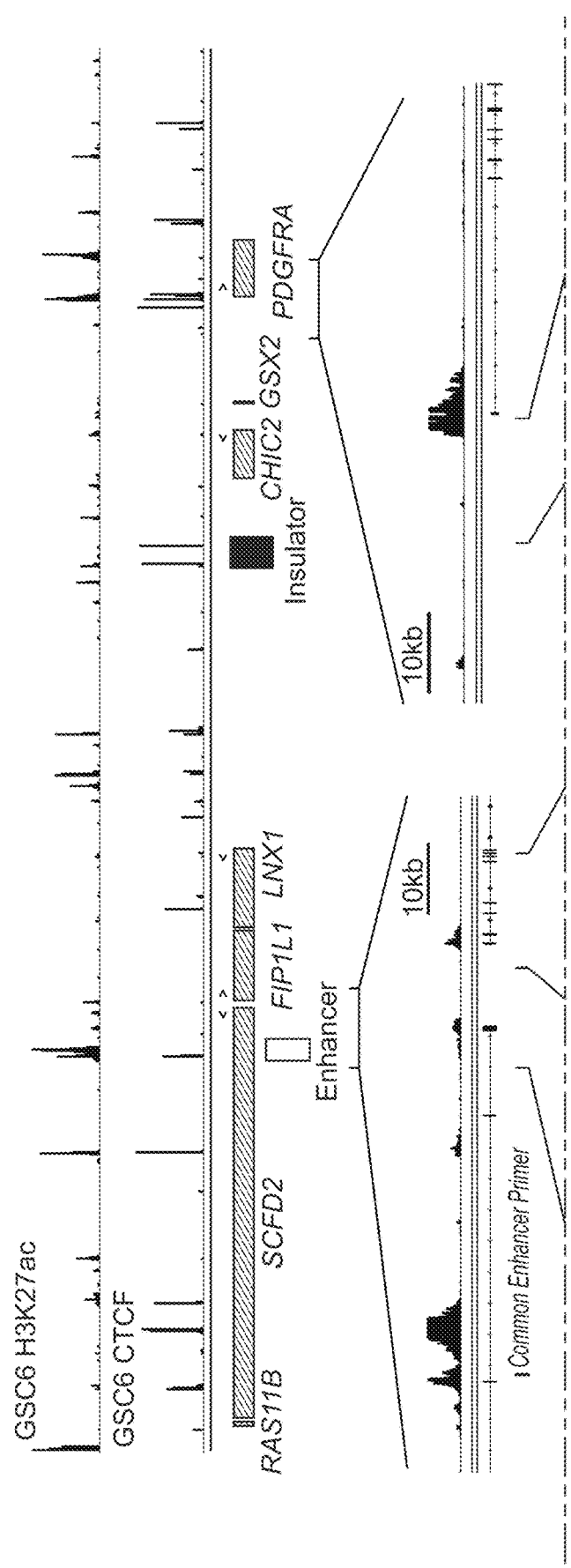
FIG. 9 illustrates interaction of the FIP1L1 enhancer with nearby promoters and PDGFRA quantified by reciprocal chromatin conformation capture (3C). (top) The H3K27ac, CTCF and genetic architecture of the FIP1L1/PDGFRA locus is indicated, highlighting the 3C strategy. (bottom) Plots indicate the interaction signal of the indicated sites (black lines) with the common enhancer primer. The FIP1L1 enhancer interacts with local promoters in wild-type and mutant tumors and models. In IDH wild-type gliomas, it shows essentially no interaction with the PDGFRA promoter. In IDH mutant gliomas, it interacts with the PDGFRA promoter with comparable strength to the local interactions, despite the much larger intervening distance (900 kb). Error bars reflect standard deviations.

In wildtype gliomas, 3C revealed a strong interaction between the PDGFRA promoter and its intragenic enhancer, which are ~50 kb apart (FIG. 3j,k). In contrast, the PDGFRA promoter does not interact with the FIP1L1 enhancer in wildtype tumors, consistent with retention of the intervening boundary (FIG. 3h,i). However, the interaction patterns were markedly different in IDH mutant tumors. Here, 3C revealed a strong interaction between the PDGFRA promoter and the FIP1L1 enhancer, despite a separation of ~900 kb (FIG. 3i). For comparison, this interaction is ~5-fold stronger than that between PDGFRA promoter and its intragenic enhancer. To confirm this interaction, Applicants designed and normalized reciprocal probe and primers to compare the relative strength with which the FIP1L1 enhancer interacts with nearby promoters and PDGFRA (FIG. 9). Remarkably, Applicants found that the FIP1L1 enhancer-PDGFRA promoter interaction is stronger than the FIP1L1 enhancer-FIP1L1 promoter interaction in IDH mutant tumors. This suggests that disruption of a boundary element by IDH mutation and hyper-methylation allows a potent constitutive enhancer to aberrantly interact with, and up-regulate PDGFRA.

Figure 4A:
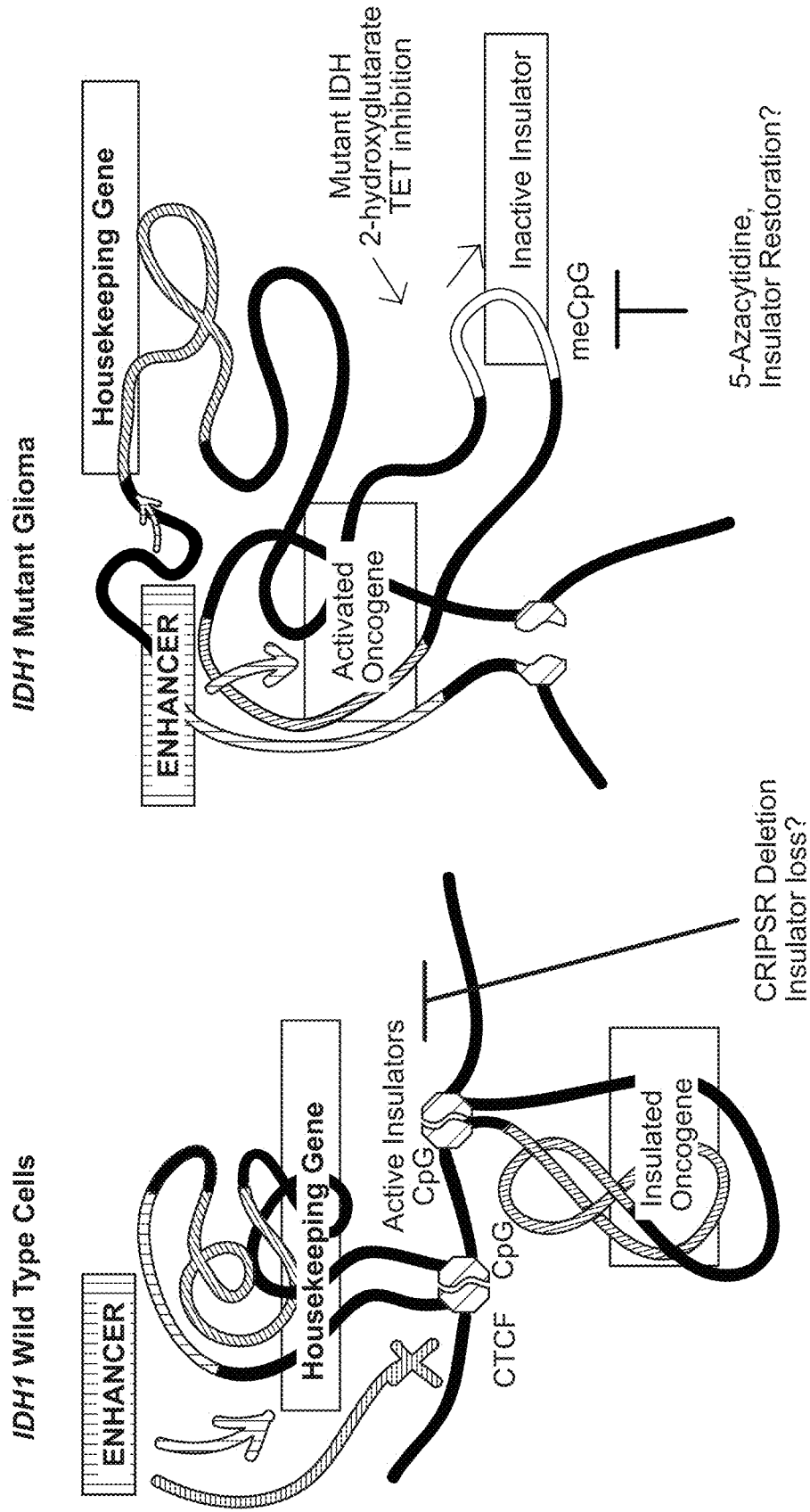
FIG. 4A-4K illustrates that boundary methylation and CTCF occupancy affect PDGFRA expression and proliferation. (a) Schematic depicts chromatin loops and boundaries in the PDGFRA locus. In IDH wildtype cells (left), intact boundary insulates oncogene. Disruption of boundary by removing CTCF motif should activate the oncogene. In IDH mutant (right), hyper-methylation blocks CTCF, compromising boundary and allowing enhancer to activate oncogene. Demethylation should restore CTCF-mediated insulation. (b) Plot compares methylation of the CpG in the CTCF motif in IDH wildtype gliomaspheres (black), IDH mutant gliomaspheres (red) and IDH mutant gliomaspheres treated with 5 µM 5-aza for 8 days (purple). (c) Plot compares CTCF occupancy over the boundary. (d) Plot compares PDGFRA expression. Demethylation restores PDGFRA insulation in IDH mutant gliomaspheres. (e) CTCF binding shown for the FIP1L1/PDGFRA region. Expanded view shows CTCF motif in the insulator targeted for CRISPR-based deletion (SEQ ID NO: 2). gRNA and protospacer adjacent motif (PAM) direct Cas9 nuclease to the motif. (f) Surveyor assay detects target site alterations in GSC6 gliomaspheres infected with Cas9 and sgRNA (but not in control cells infected with GFP-targeting sgRNA). (g) Sequencing of target site reveals the indicated deletions. CTCF motif disrupted on ~25% of alleles (compare to <0.01% in control) (SEQ ID NOs: 3-8, numbered sequentially from top to bottom). (h) Plot depicts fraction of reads in insulator CRISPR cells with a deletion of indicated size. (i) qPCR reveals increased PDGFRA expression in insulator CRISPR cells. (j) Flow cytometry reveals ~2-fold greater PDGFRa in insulator CRISPR cells. (k) Plot depicts gliomasphere growth. Insulator CRISPR cells exhibit ~2-fold increased proliferation, relative to control. This proliferation advantage is eliminated by PDGFRa inhibition. These results indicate that genetic or epigenetic disruption of the boundary compromises insulation of this oncogene. (Error bars in all panels reflect standard deviations of triplicate observations).
Figure 4:
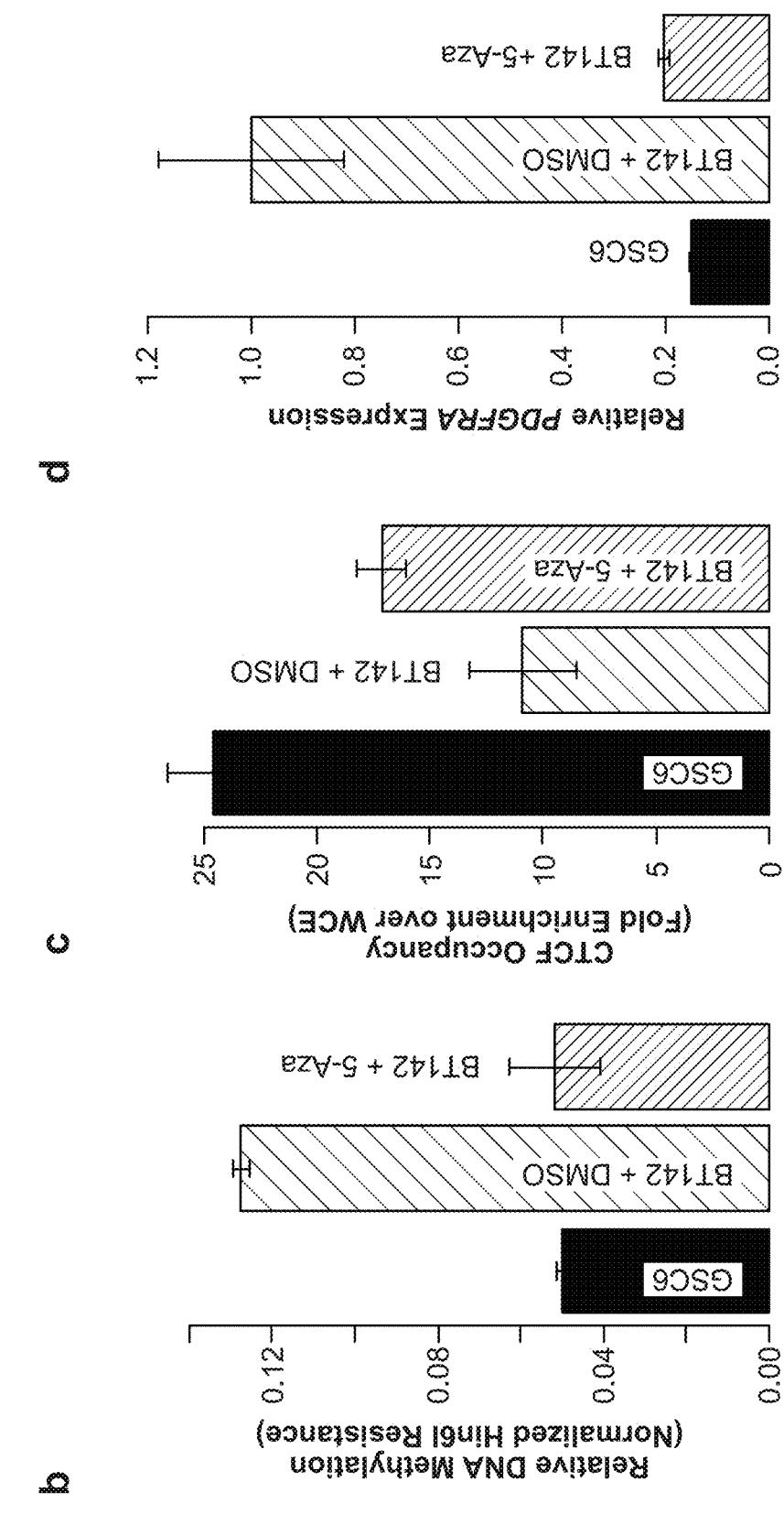
Figure 4:
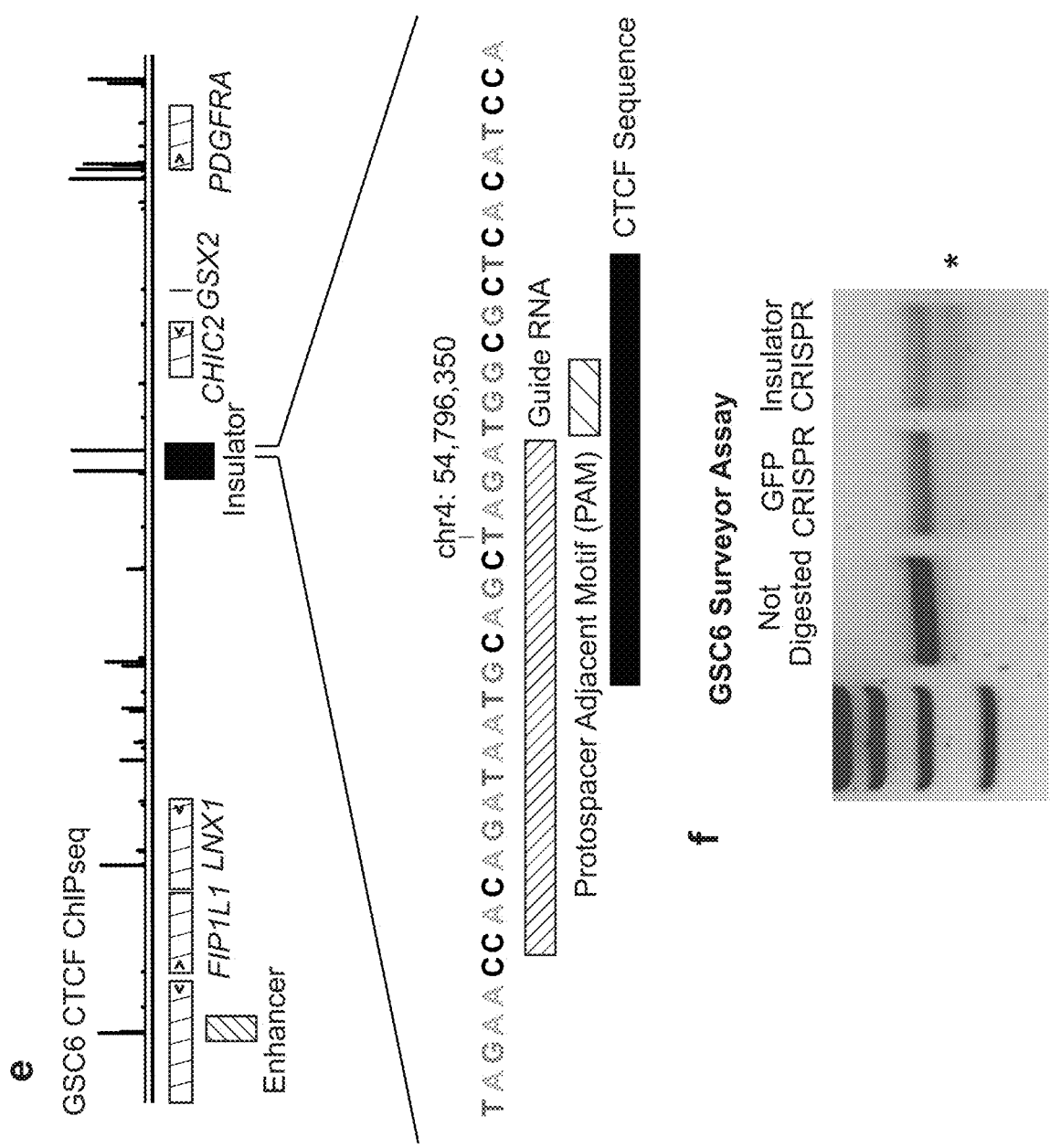

Example 4. Boundary Methylation and CTCF Occupancy Affect PDGFRA Expression and Proliferation To test this model functionally, Applicants considered whether perturbing the boundary alters PDGFRA expression in patient-derived gliomaspheres (FIG. 4a). First, Applicants focused on the IDH1 mutant oligoastrocytoma model, BT142. In this mutant line, the CpG dinucleotide in the CTCF motif exhibits higher methylation than wildtype models (~13% vs ~2% per bisulfite sequencing), and CTCF binding is ~3-fold lower. Consistently, 3C reveals a strong interaction between FIP1L1 enhancer and PDGFRA promoter that is specific to the mutant line (FIG. 3i), and PDGFRA is highly expressed.

Applicants reasoned that demethylating agent should reduce methylation at this CpG dinucleotide, allowing CTCF to bind and restore PDGFRA insulation. Applicants therefore treated BT142 gliomaspheres with the DNA methyltransferase inhibitor 5-azacytidine (5-aza). 5-aza treatment reduced methylation of the CTCF motif by ~2.5-fold, increased CTCF occupancy by ~1.7-fold and down-regulated PDGFRA expression by ~5-fold (FIG. 4b-d). These results directly implicate DNA hyper-methylation in compromising CTCF binding, boundary function and oncogene insulation in IDH mutant tumors.

Finally, Applicants investigated whether genetic disruption of the CTCF motif could induce PDGFRA expression in wildtype gliomaspheres with an intact boundary (FIG. 4a). Here Applicants focused on GSC6, a patient-derived glioblastoma model that harbors an EGFR amplification, but is wildtype for IDH and PDGFRA. Applicants sought to disrupt the CTCF site in the boundary by CRISPR-based genome engineering (FIG. 4e)[26,27]. Applicants designed a short guide RNA (sgRNA) with a protospacer adjacent motif (PAM) within the CTCF motif. Applicants used a single-vector lentiviral delivery system to infect GSC6 with a Cas9 expression construct containing this insulator sgRNA or a control sgRNA (targeting GFP). Surveyor assay confirmed target locus disruption in the insulator CRISPR condition (FIG. 4f). Direct sequencing of the target locus revealed that ~25% of alleles in the insulator CRISPR gliomaspheres contain a deletion within the CTCF motif expected to disrupt binding, compared to <0.1% in the GFP control (FIG. 4g,h).

Applicants quantified PDGFRA expression in the genetically modified gliomaspheres. RT-PCR revealed a ~1.6-fold increase in PDGFRA mRNA in the insulator CRISPR cells, relative to control (FIG. 4i). Similarly, flow cytometry revealed a ~1.8-fold increase in the fraction of cells with PDGFRa surface expression (FIG. 4j). Applicants conservatively estimate that CTCF motif disruption causes a ~3-fold increase in PDGFRA expression, given that DNA level analysis indicates that <50% of insulator CRISPR cells were successfully edited.

Figure 10:
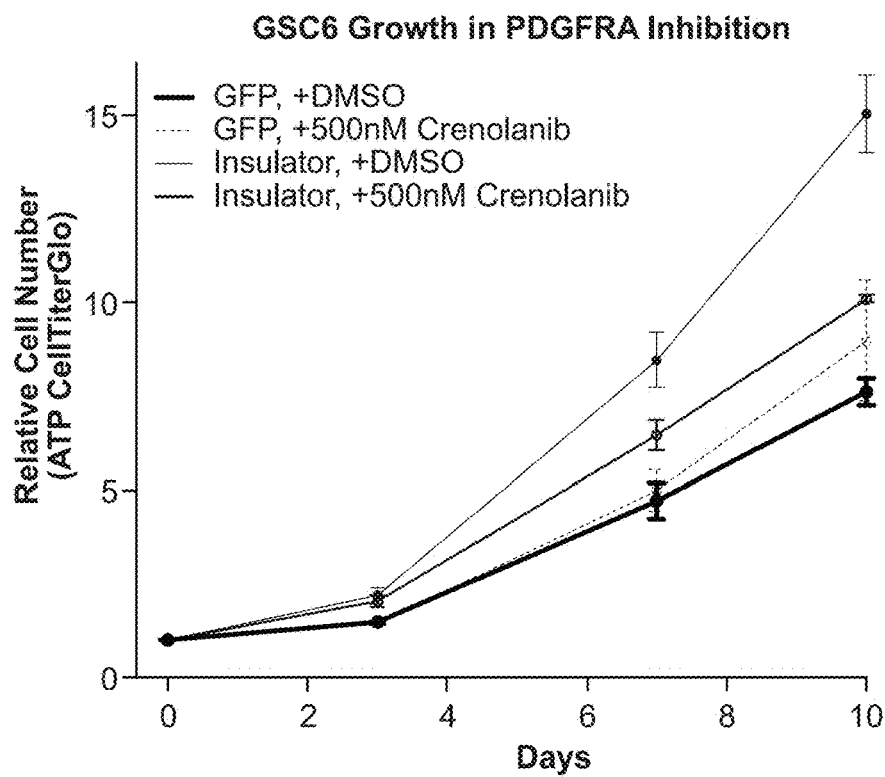
FIG. 10 illustrates that Crenolanib reverses the increased growth of PDGFRA insulator disrupted cells. Insulator CRISPR-infected gliomaspheres exhibit a roughly 2-fold increase in proliferation rate, compared to control sgRNA infected gliomaspheres. This proliferative advantage is eliminated by treatment with the PDGFRa inhibitor Crenolanib. Crenolanib and Dasatinib both inhibit PDGFRa, but their other targets are non-overlapping. Hence, this sensitivity provides further support that PDGFRA induction drives the increased proliferation of the insulator CRISPR gliomaspheres. (Error bars reflect standard deviations).

Finally, Applicants considered whether CRISPR-mediated boundary disruption and PDGFRA induction affects gliomasphere fitness. In support, the insulator CRISPR gliomaspheres have a ~2-fold growth advantage over the control GFP CRISPR gliomaspheres (FIG. 4k). This growth advantage is dependent on PDGFRa signaling, as it is abrogated by treatment with PDGFR inhibitors, dasatinib or crenolanib (FIG. 4k, FIG. 10). Notably, PDGFRA expression in insulator CRISPR gliomaspheres increased further after extended culture (to 2-fold over control), potentially due to selection of effectively edited clones. The observation that genetic disruption of this CTCF boundary element induces PDGFRA expression and enhances proliferation provides strong support for our model that epigenetic disruption of this element offers similar growth advantage to IDH mutant gliomas.

Example 5. Conclusions

In conclusion, Applicants present a novel epigenetic mechanism by which gain-of-function IDH mutations induce PDGFRA expression and thereby promote fitness in a subset of gliomas. Applicants specifically find that, in addition to familiar effects on CpG islands, IDH mutations cause hyper-methylation of CTCF binding sites genome-wide. This is associated with reduced CTCF binding and a global deregulation of boundary elements that partition topological domains. Disruption of a specific boundary bordering PDGFRA allows a potent enhancer to aberrantly contact and activate this canonical glioma oncogene.

Although disruption of this single boundary confers a growth advantage, it is unlikely to be the only mediator of IDH mutations in gliomas. The widespread disruption of CTCF binding and boundary element function could provide many opportunities for oncogene deregulation, and subsequent selection of proliferative progeny that inherit the altered epigenetic state. Insulator dysfunction may also be accompanied by promoter silencing events[28,29], and by alterations to other pathways affected by 2-HG[7,30]. Conversely, disruption of chromosomal topology and oncogene insulation may be more generally relevant to methylator phenotypes observed in colorectal and renal cell carcinomas, leukemia and other malignancies[28].

Figure 14:
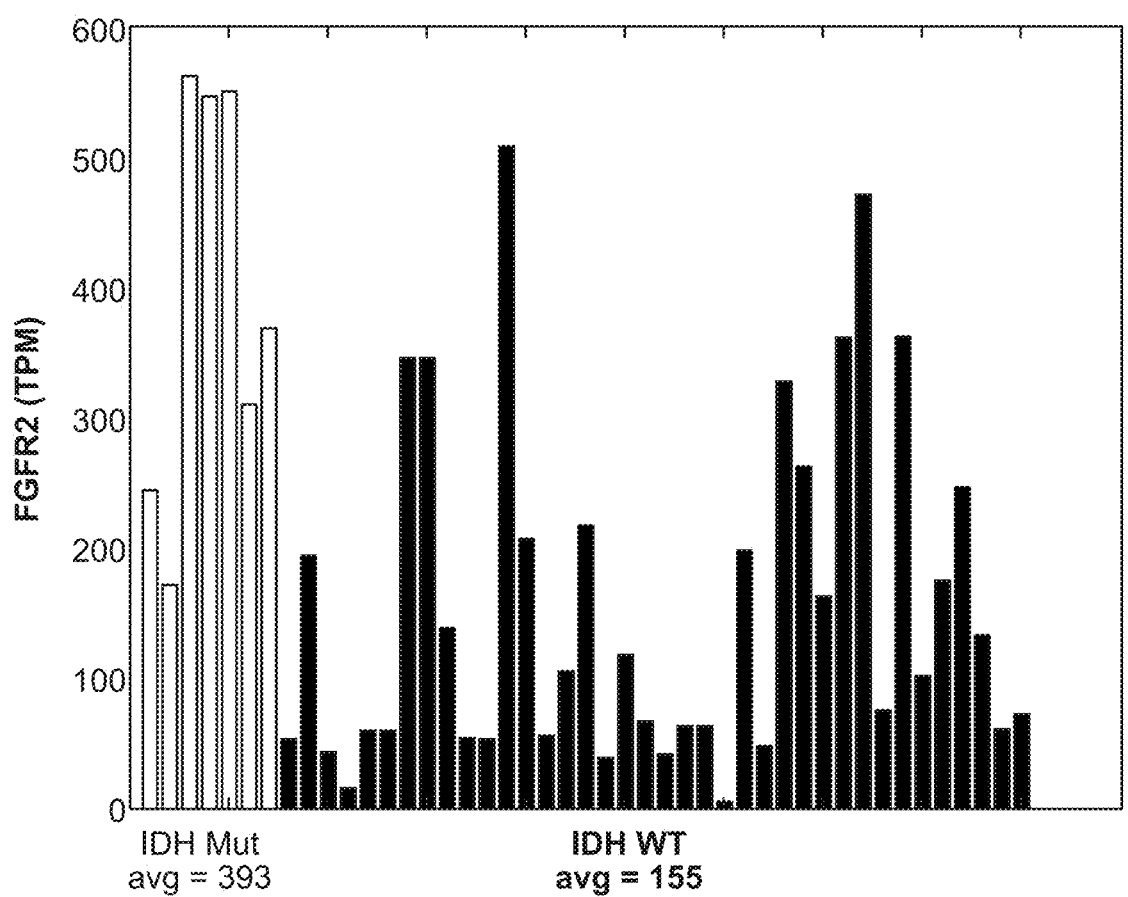
FIG. 14 illustrates that IDH mutant cholangiocarcinoma displays high levels of FGFR2 as compared to IDH wild-type.
Figure 15:
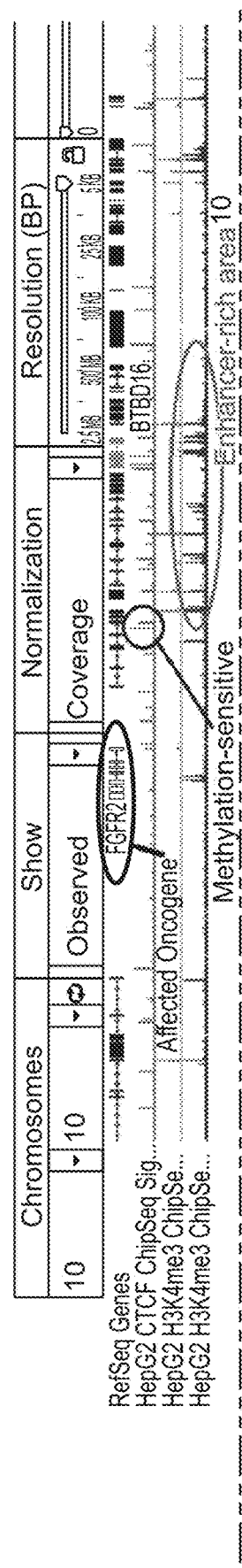
FIG. 15 illustrates an insulator that contains a CpG at the methylation-sensitive site of the CTCF binding sequence and separates the FGFR2 gene from a nearby enhancer-rich region, which drives FGFR2 expression following insulator loss.
Figure 15:
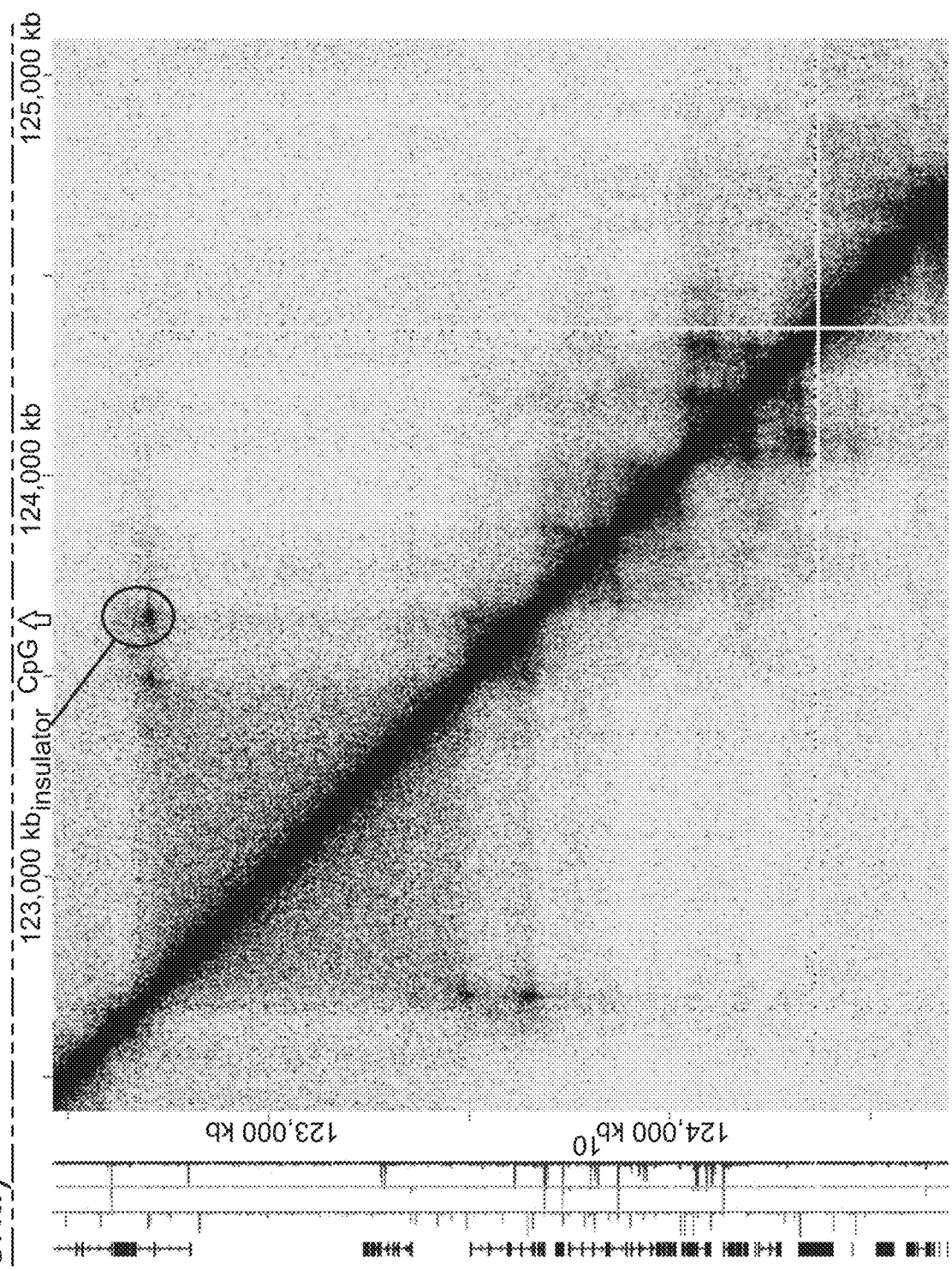

Example 6. A Methylation-Sensitive Insulator Separates the FGFR2 Gene from an Enhancer-Rich Region IDH mutations are present in about 15% of Cholangiocarcinomas. Other cholangiocarcinomas can contain translocations creating FGFR2 fusion genes. Given the role of FGFR2 fusion proteins in Cholangiocarcinoma, Applicants hypothesized that loss of this insulator will be a sufficient oncogenic signal to drive these tumors. Applicants show that there is an insulator separating the FGFR2 gene from a nearby enhancer-rich region and the insulator contains a CpG at the methylation-sensitive site of the CTCF binding sequence (FIG. 15). Furthermore, IDH mutant cholangiocarcinoma displays high levels of FGFR2, compared to IDH wild-type (FIG. 14). Thus, loss of IDH can drive FGFR2 expression following insulator loss.

Example 7. Disruption of CTCF Binding Using a CRISPR-Cas System

Figure 16A:
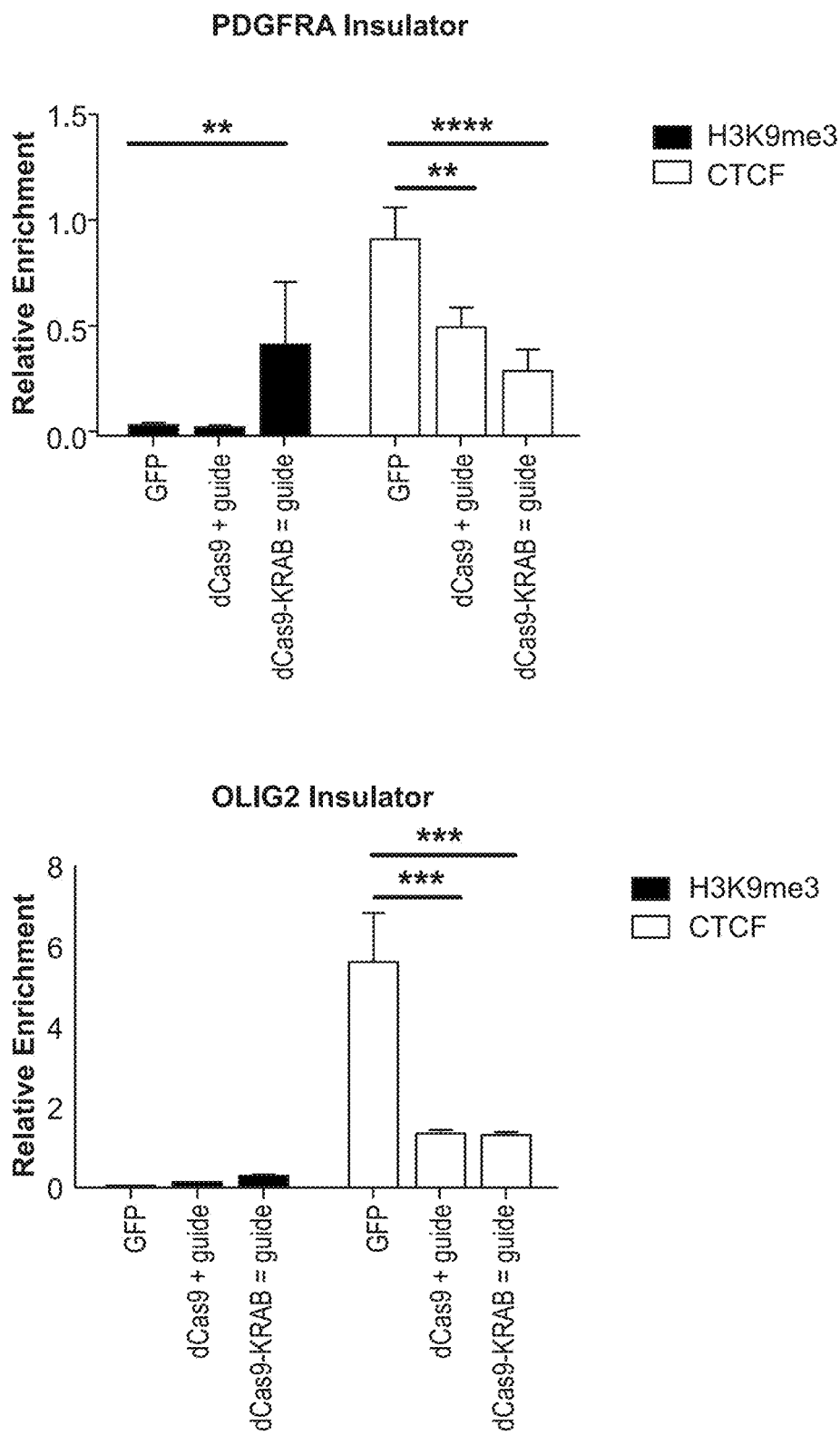
FIG. 16A-16B illustrates disruption of CTCF binding and enrichment of H3K9me3. (a) Top: Relative enrichment data for H3K9me3 and CTCF at the PDGFRA insulator (chr4: 54,796,108-54,796,533, hg19). Values represent the average ratio of enrichments of the target site to positive control enrichments (ZFP28 3' end for H3K9me3, SPG11 proximal CTCF site for CTCF). Only the dCas9-KRAB recruits H3K9me3 to the target site while both dCas9 and dCas9-KRAB can reduce CTCF binding to the target site. N=2, two biological replicates each. Error bars represent one standard deviation. Bottom: Relative enrichment data for H3K9me3 and CTCF at the OLIG2 insulator (chr21:34569286-34569487, hg19). Both dCas9 and dCas9-KRAB can reduce CTCF binding to the target site. N=2, two biological replicates each. Error bars represent one standard deviation. (b) Same data as in (a), bottom panel. H3K9me3 and CTCF data is separated into two panels with scale adjusted and showing values for dCas9-KRAB and GFP conditions.
Figure 16B:
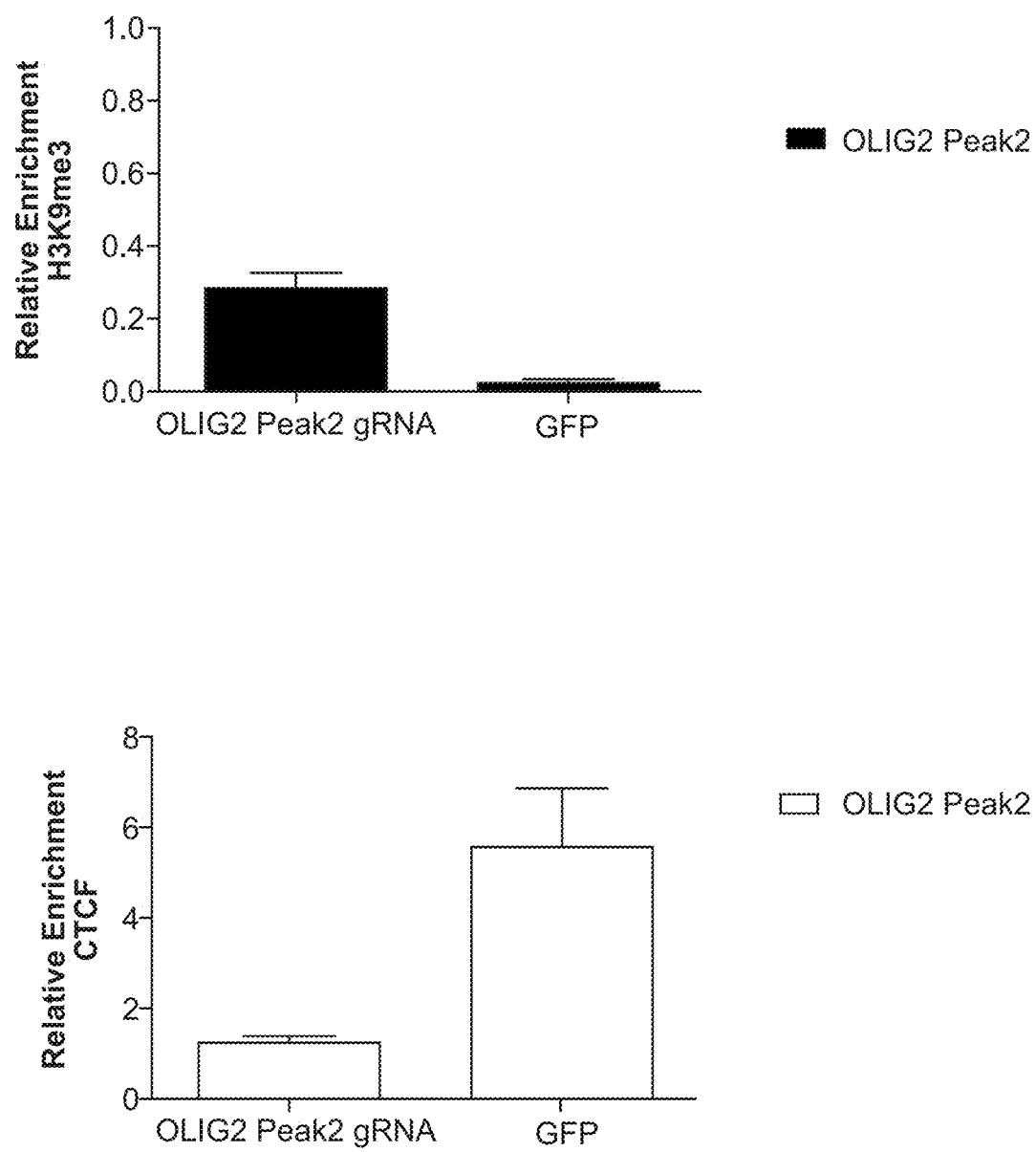
Figure 18:
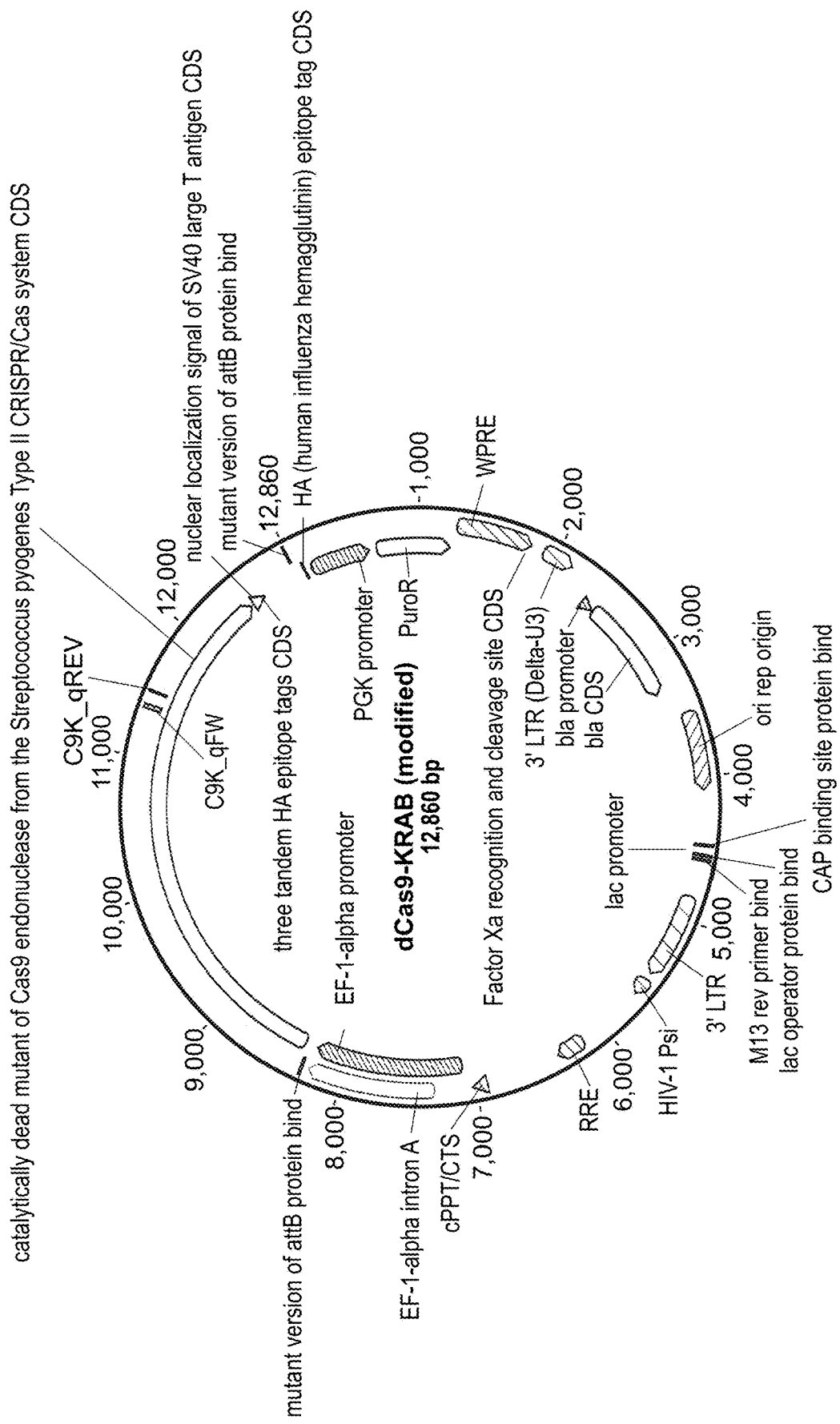
FIG. 18 illustrates a map of a dCas9-KRAB expression vector.
Figure 19:
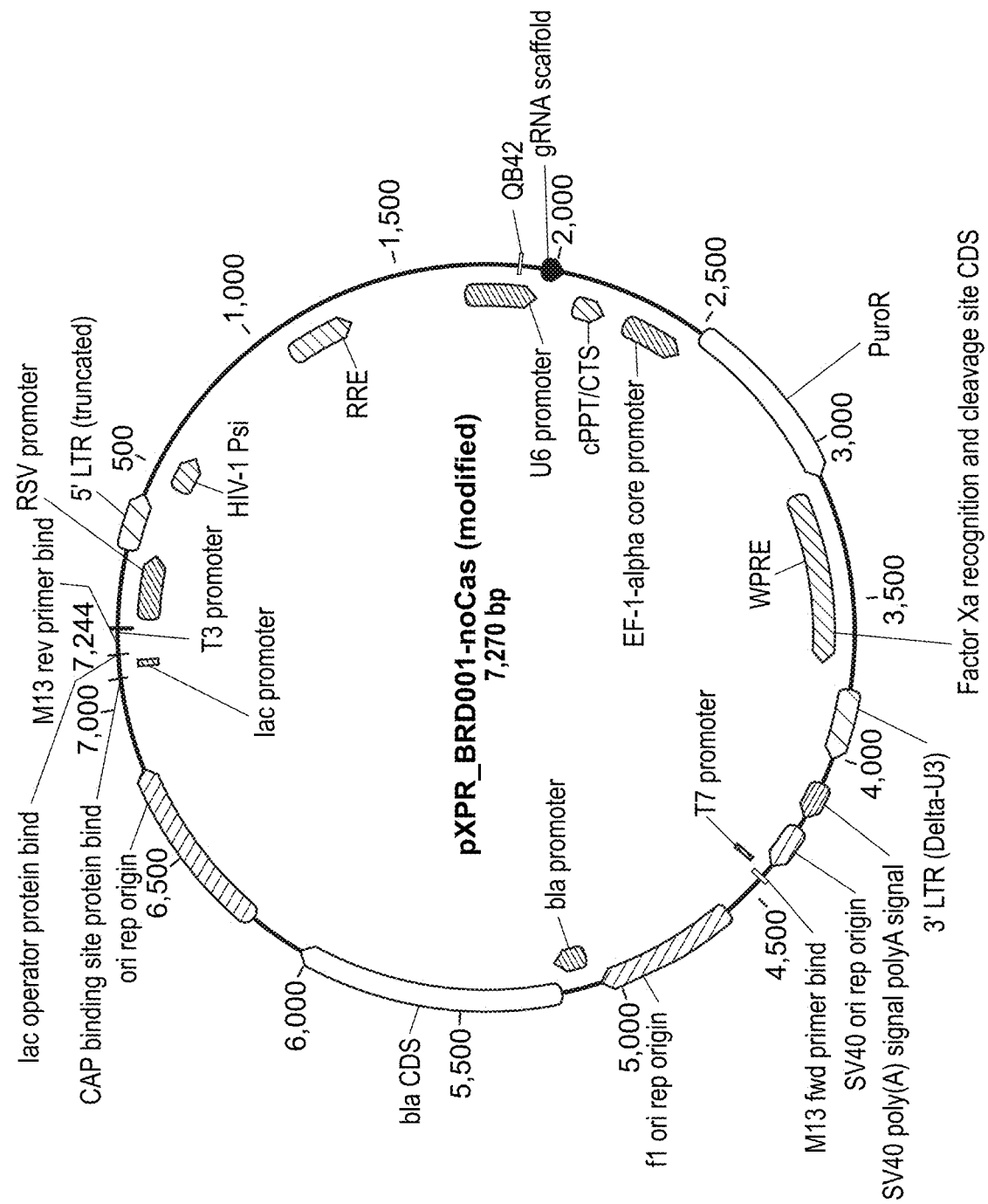
FIG. 19 illustrates a map of a gRNA expression vector.

Applicants show for the first time that recruitment of enzymatically inactive CRISPR enzyme (dCas9) or CRISPR enzyme fusion protein (dCas9-KRAB) to a CTCF insulator potently disrupts CTCF binding (FIG. 16). Applicants also show that recruitment dCas9-KRAB results in the enrichment of the repressive epigenetic modification H3K9me3. Applicants performed these experiments at the PDGFRA insulator in HEK293 cells (FIG. 16A, Top). Applicants also show that dCas9 and dCas9-KRAB binding can disrupt CTCF binding in HEK293 cells at the OLIG2 insulator (FIG. 16A, Bottom). Applicants also show that recruitment dCas9-KRAB results in the enrichment of the repressive epigenetic modification H3K9me3 (FIG. 16B). HEK293 cells were seeded into 100 mm cell culture dishes two days before transfection and grown to 60-70% confluency. Bug of either dCas9 or dCas9-KRAB constitutive expression vector (JDS286 and Addgene Plasmid #50919 respectively) (FIG. 18) and 1 ug of guide RNA expression vector (pXPR1_noCas, Broad GPP) (FIG. 19) were mixed in 450ul OptiMEM. 27ul of FugeneHD was added and tubes were vortexed for two times one second, incubated at room temp for ten minutes and added dropwise to cell culture dishes.

Cells were harvested three days after transfection and crosslinked in 1% formaldehyde at 37 C for 10 min. ChIP-qPCR was performed as previously described. Briefly, cells were lysed on ice, sonicated in 0.3% SDS for 5 minutes total time at ~10W power, incubated with the relevant antibody overnight at 4C with rotation after dilution to 0.1% SDS. Antibody-bound chromatin was isolated using protein G magnetic beads. Bound complex is washed several times and eluted off the beads at 65C for 1h with shaking. Eluted complex is treated with RNase for 30 min at 37C and protinase K for 3h at 63C while crosslinks are reversed concurrently. IP DNA is cleaned up using a 2× Ampure XP DNA bead cleanup as per manufacturer's instructions.

Figure 17:
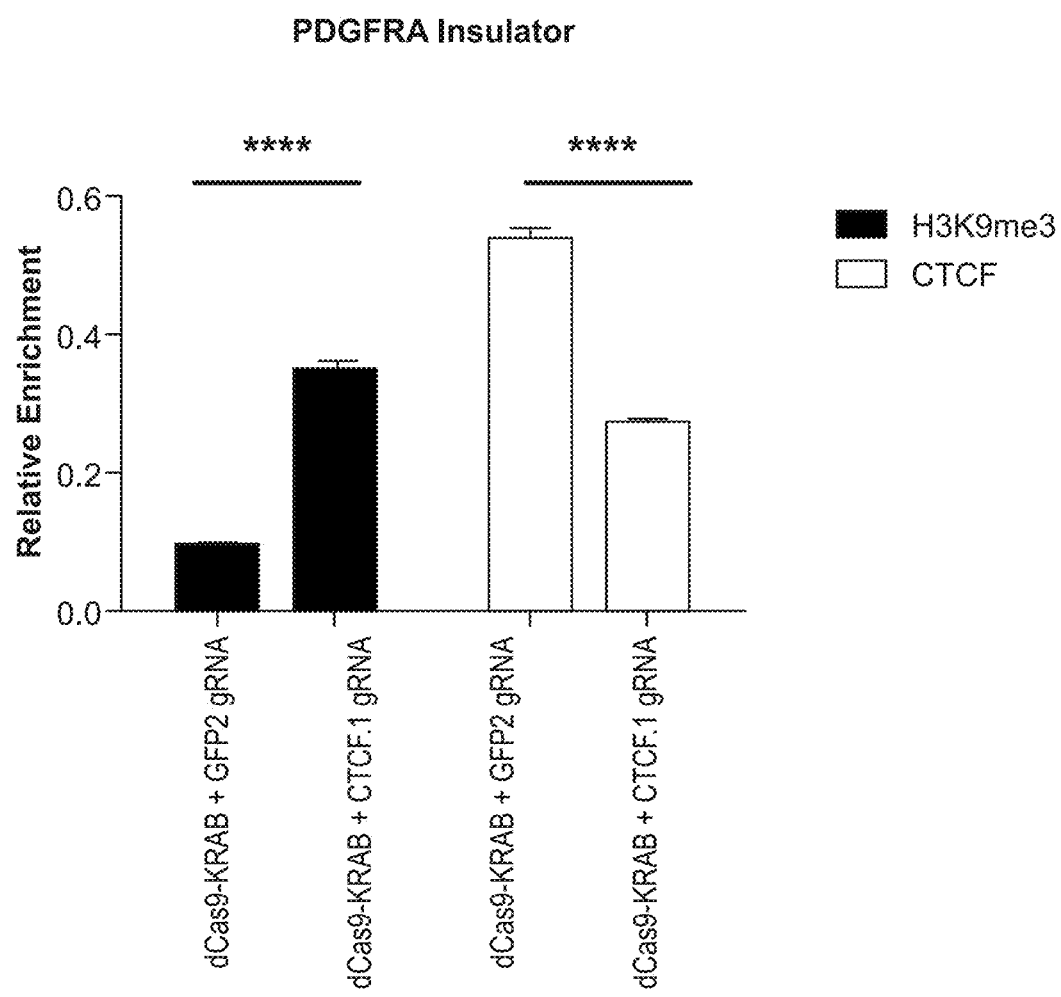
FIG. 17 illustrates dCas9-KRAB recruits H3K9me3 and disrupts CTCF binding in GBM8 cells. Relative enrichment data for H3K9me3 and CTCF at the PDGFRA insulator (chr4:54,796,108-54,796,533, hg19). Values represent the average ratio of enrichments of the target site to positive control enrichments (ZFP28 3' end for H3K9me3, SPG11 proximal CTCF site for CTCF). Only the dCas9-KRAB recruits H3K9me3 to the target site and reduces CTCF binding to the target site. N=1. Error bars represent one standard deviation.

Applicants also show that dCas9-KRAB recruits H3K9me3 and disrupts CTCF binding in GBM8 cells (glioma cell line) (FIG. 17). 1E6 GBM8 cells were plated as a single cell suspension in a 100 mm cell culture dish with 10 mL of CSC media with 50 ug of laminin. Plated cells were infected with lentivirus coding for dCas9-KRAB-P2A-mCherry (Addgene Plasmid #60954). Three days after infection cells were sorted for mCherry expression. Sorted cells were recovered in 12 ml CSC media in a T75 flask and subsequently 1E6 dCas9-KRAB-P2A-mCherry expressing cells were plated and infected with lentivirus coding for guide RNA a expression vector (pXPR1_noCas, Broad GPP) as above. Two days after guide RNA infection, cells were selected in 1 ug/ml puromycin for two days. Cells were recovered in fresh CSC media and 5E6 cells were harvested for ChIP-qPCR as described above (same approach as HEK293s).

Methods and Materials

Primary glioma specimens and gliomasphere models—Clinical samples GBM1w, GBM2w, GBM3w, GBM4w, GBM5w, GBM6w, GBM7w, AA15m, AA16m, AA17m, OD18m, and AA19m were obtained as frozen specimens from the Massachusetts General Hospital Pathology Tissue Bank or received directly after surgical resection and flash frozen (FIG. 12). All samples were acquired with Institutional Review Board approval, and were deidentified prior to receipt. GBM1w was obtained at autopsy; the remaining samples were surgical resections. IDH1 status was determined for all clinical samples by SNaPshot multiplex PCR[31]. PDGFRA status was confirmed by FISH analysis. Tissue (200-500 µg) was mechanically minced with a sterile razor blade prior to further processing.

Gliomaspheres were maintained in culture as described[32,33]. Briefly, neurosphere cultures contain Neurobasal media supplemented with 20 ng/mL recombinant EGF (R and D Systems™), 20 ng/mL FGF2 (R and D Systems™), 1×B27 supplement (Invitrogen™), 0.5×N2 supplement (Invitrogen™), 3 mM L-glutamine, and penicillin/streptomycin. Cultures were confirmed to be mycoplasma-free via PCR methods. GSC4 and GSC6 gliomasphere lines were derived from IDH1 wildtype tumors resected at Massachusetts General Hospital, and have been previously described and characterized[32-34]. BT142 gliomasphere line (IDH1 mutant)[35] was obtained from ATCC, and cultured as described above except 25% conditioned media was carried over each passage. BT142 G-CIMP status was confirmed by evaluating LINE methylation with the "Global DNA Methylation Assay—LINE-1" kit (Active Motif®), as described[36], and by methylation-sensitive restriction digests. GSC119 was derived from an IDH1 mutant tumor (confirmed by SNaPsShot) resected at Massachusetts General Hospital. Applicants confirmed IDH1 mutant status of GSC119 by RNA-seq (82 out of 148 reads overlapping the relevant position in the transcript correspond the mutant allele). The gliomasphere models were derived from tumors of the following type: GSC4, GSC6—primary glioblastoma, BT142—grade III oligoastrocytoma, GSC119—secondary glioblastoma, G-CIMP. Clinical specimens and models used in this study are detailed in FIG. 12.

Chromatin Immunoprecipitation—Chromatin Immunoprecipitation (ChIP) and sequencing (ChIP-Seq) was performed as described previously[32]. Briefly, cultured cells or minced tissue was fixed in 1% formaldehyde and snap frozen in liquid nitrogen and stored at −80° C. for at least overnight. Sonication of tumor specimens and gliomaspheres was calibrated such that DNA was sheared to between 400 bp and 2000 bp. CTCF was immunoprecipitated with a monoclonal rabbit CTCF antibody, clone D31H2 (Cell Signaling Technology® 3418). H3K27ac was immunoprecipitated with an antibody from Active Motif® (cat 39133). ChIP DNA was used to generate sequencing libraries by end repair (End-It™ DNA repair kit, Epicentre), 3' A base overhang addition via Klenow fragment (NEB), and ligation of barcoded sequencing adapters. Barcoded fragments were amplified via PCR. Libraries were sequenced as 38 base paired-end reads on an Illumina® NextSeq500 instrument or as 50 base single-end reads on a MiSeq instrument. Sequencing libraries are detailed in FIG. 13. H3K27ac maps for GSC6 were previously published deposited to GEO as GSM1306340. Genomic data has been deposited into GEO as GSE70991.

For sequence analysis, identical reads were collapsed to a single paired-end read in order to avoid PCR duplicates. In order to avoid possible saturation, reads were downsampled to 5% reads collapsed as PCR duplicates, or 5 million fragments. Reads were aligned to hg19 using BWA, and peaks were called using HOMER. ChIP-seq tracks were visualized using Integrative Genomics Viewer (IGV, www-.broadinstitute.org/igv/). To detect peaks lost in IDH mutants, Applicants called signal over all peaks in a 100 bp window centered on the peaks. To control for copy number changes, Applicants first called copy number profiles from input sequencing data using CNVnator[37]. Applicants then removed all regions where at least one sample had a strong deletion (<0.25), and normalized by copy number. To account for batch effects and difference in ChIP efficiency, Applicants quantile normalized each dataset. Peaks were scored as lost or gained if the difference in signal between a given tumor and the average of the five wildtype tumors was at least 2-fold lower or higher, with a signal of at least 1 in all wildtype or all IDH mutant tumors. Fisher exact test confirmed that the overlap between peaks lost in the IDH mutant tumors is highly significant ($p<10^{-100}$).

GC content over CTCF peaks lost (or retained) in the IDH1 mutant glioma specimens was averaged over 200 bp windows centered on each peak lost in IDH mutant tumors. Methylation levels were quantified over these same regions for 3 IDH mutant and 3 IDH wildtype tumors, using TCGA data generated by whole genome bisulfite sequencing[10]. Briefly, methylation levels (%) based on proportion of reads with protected CpG were averaged over all CpG dinucleotides in these regions, treating each tumor separately.

Occupancy of the CTCF site in the boundary element adjacent to the PDGFRA locus was quantified by ChIP qPCR, using the following primers: PDGFRActcfF: 5'-GTC ACA GTA GAA CCA CAG AT-3' (SEQ ID NO: 27) PDGFRActcfR: 5'-TAA GTA TAC TGG TCC TCC TC-3' (SEQ ID NO: 28). Equal masses of ChIP or input (WCE) DNA were used as input for PCR, and CTCF occupancy was quantified as a ratio between ChIP and WCE, determined by 2^-deltaCT. CTCF peak intensity was further normalized as ratio to two invariant peaks, at PSMB1 and SPG11, using the following primers: PSMB1ctcfF—5'-CCT TCC TAG TCA CTC AGT AA-3' (SEQ ID NO: 29), PSMB1ctcR—5'-CAG TGT TGA CTC ATC CAG-3' (SEQ ID NO: 30), SPG11ctcfF—5'-CAG TAC CAG CCT CTC TAG-3' (SEQ ID NO: 31), SPG11ctcfR—5'-CTA AGC TAG GCC TTC AAG-3' (SEQ ID NO: 32).

Figure 11:
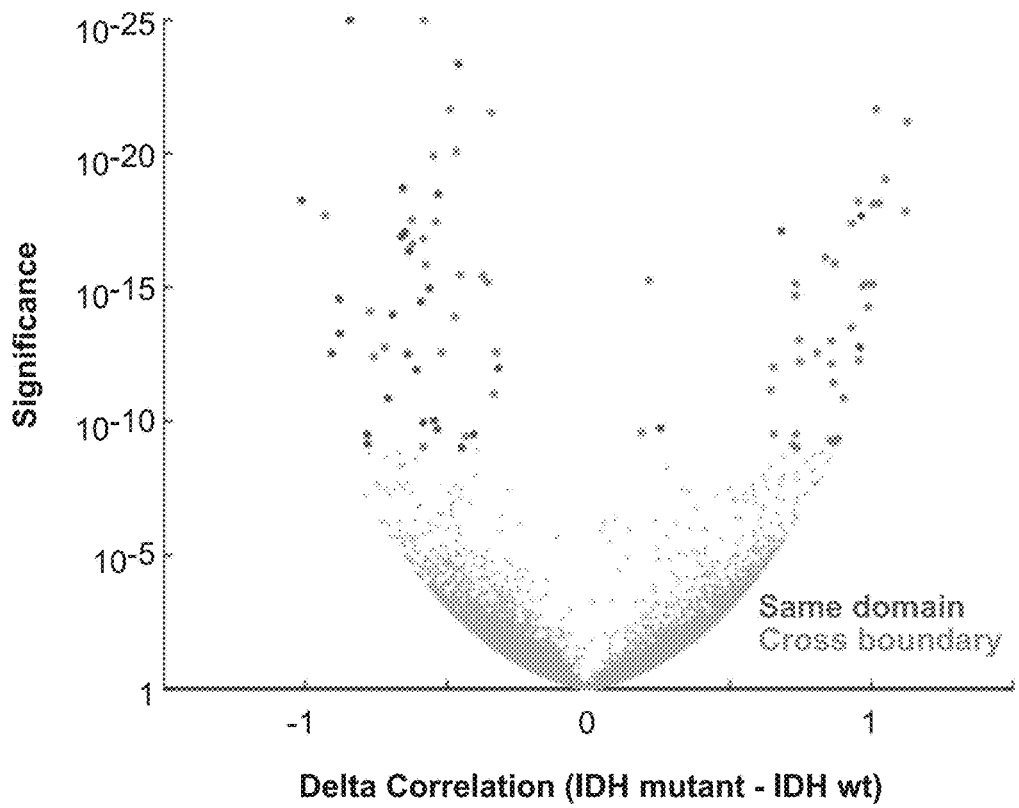
FIG. 11 illustrates that the signature of boundary deregulation in IDH mutant gliomas is robust. Volcano plot depicts the significance (y-axis) of gene pairs that are either more or less correlated in IDH mutant than IDH wild-type gliomas. This plot was generated by repeating the analysis described herein and shown in FIG. 1f, except that here the statistics were performed using only the 14,055 genes expressed at >1 TPM in at least half the samples. This indicates that the boundary deregulation signature in IDH mutant gliomas is not sensitive to noise from lowly expressed genes.

Cross-Boundary and Intra-Domain Gene Pair Correlation Analysis—RNA-seq data for 357 normal brain samples was downloaded from GTEx[20]. RNA-seq data and copy number profiles for lower grade gliomas were downloaded from TCGA[23,24]. Contact domains of IMR90, GM12878, K562 and NHEK cells were obtained from published HiC data[15]. Genes were assigned to the inner-most domain their transcription start site fell within. Gene pairs were considered to be in the same domain if they were assigned to the same domain in both GM12878 and IMR90. Gene pairs were considered to span a boundary if they were assigned to different domains in both GM12878 and IMR90, and separated by a CTCF binding site in IDH wild type tumors. Gene pairs that did not fit either criterion were excluded from this analysis. The plot of correlation vs distance for brain GTEx samples is based on Pearson correlations for all relevant pairs, smoothed by locally weighted scatterplot smoothing with weighted linear least squares (LOESS). To assess the bias in correlation differences, Applicants computed the difference of Pearson correlations between wild-type and IDH mutant gliomas for all gene pairs separated by <180 kb. In FIG. 1e, this difference in correlations is plotted against the significance of this difference (estimated by Fisher z-transformation). For each gene pair, Applicants omitted samples with a deletion or amplification of one of the genes at or above threshold of the minimal arm level deletion or amplification (to avoid copy number bias). To ensure robustness, Applicants also repeated the analysis using boundaries defined from HiC data for K562 and NHEK. This yielded similar results: 84% pairs gaining correlation cross boundary vs. 71% expected ($p<8*10^{-3}$), 54% pairs losing correlation are within the same domain vs. 29% expected ($p<3*10^{-8}$). Repeating the analysis with only the 14,055 genes that have expressed over 1 TPM in at least half the samples also yielded similar results (FIG. 11): 92% pairs gaining correlation cross boundary vs. 69% expected ($p<2*10^{-3}$), 73% pairs losing correlation are within the same domain vs. 31% expected ($p<8*10^{-4}$).

Genomic Scan for Deregulated Boundaries—To detect boundaries deregulated in IDH mutant gliomas, Applicants scanned for gene pairs, separated by <1 MB, with a significant difference in correlation between wild-type and IDH mutant tumors (Fisher z-transformation, FDR<1%). Applicants omitted amplified or deleted samples as described above. To ensure robustness to noise from lowly expressed genes, Applicants first filtered out 6,476 genes expressed <1 TPM in more than half of the samples (keeping 14,055 genes). Applicants considered all domains and boundaries scored in IMR90 HiC data[13]. Gene pairs crossing a CTCF peak and an IMR90 boundary (i.e. can be assigned to different domains) that were significantly more correlated in IDH mutant tumors were considered to support the loss of that boundary. Gene pairs not crossing a boundary (i.e. can be assigned to the same domain) that were significantly less correlated in IDH mutant tumors were considered to support the loss of a flanking boundary. Applicants collated a set of deregulated boundaries, supported by at least one cross-boundary pair gaining correlation and at least one intra-domain pair losing correlation. Each was assigned a p-value equal to the product of both supporting pairs (best p-value was chosen if there were more supporting pairs). If both boundaries of a domain were deregulated, or if the same pair of gene pairs (one losing and one gaining correlations) were supporting more than one boundary due to overlapping domains the entries were merged (Supplemental Table 1). This definition allows every gene pair to be considered as potential support for a boundary loss. To quantify CTCF occupancy over these deregulated boundaries, Applicants averaged the signal over all CTCF peaks located within a 1 kb window around the boundary, using copy number and quantile normalized CTCF signals. To quantify DNA methylation over the deregulated boundaries, Applicants averaged DNA methylation signals from TCGA data in 200 bp windows as above. FIG. 2a depicts significance of disrupted domains and the fold-change of genes in them that are upregulated in IDH mutant tumors (compared to median expression in wild-type). In addition to PDGFRA, top ranking genes include CHD4 ($p<10^{-32}$), a driver of glioblastoma tumor initiation[38], LICAM ($p<10^{-8}$), a regulator of the glioma stem cells and tumor growth[39], and other candidate regulators (Supplemental Table 1).

To ensure robustness to cell type-specific boundaries, Applicants repeated the analysis with GM12878, K562 and NHEK defined boundaries. This yielded very similar results, and again highlighted PDGFRA as an over-expressed gene adjacent to a disrupted boundary.

TCGA Correlation and Outcome Analysis—For the correlation of FIP1L1 and PDGFRA expression, RNAseq data from the TCGA Lower Grade Glioma (LGG) and Glioblastoma (GBM) datasets[2,24] were downloaded and segregated by IDH1 mutation status and subtype. Patients from the proneural subtype were divided by IDH mutation status, while patients from the mesenchymal, classical, or neural subtypes (which had no IDH mutations) were classified as "Other." For correlation analysis, patients with copy number variation in either gene were excluded from the analysis to control for effects of co-amplification. For outcome analysis, LGG RNAseq data and corresponding patient survival data was obtained from TCGA. Patients with sum PDGFRA and FIP1L1 expression of at least one half of one standard deviation above the mean were classified as "high PDGFRA and FIP1L1 expression" (n=17) while all other patients were classified as "low PDGFRA and FIP1L1 expression" (n=201). Data were plotted as Kaplan-Meier curves and statistically analyzed via logrank test.

HiC Data Analysis and Visualization—HiC data[15] was downloaded from GEO. 5 kb resolution intra-chromosomal contact scores for Chromosome 4 for the cell lines IMR90, NHEK, KBM7, K562, HUVEC, HMEC, and GM12878 were filtered to the region between 53,700 kb and 55,400 kb. The average interaction score at each coordinate pair for all cell lines was calculated and used to determine putative insulator elements as local maxima at the interaction point of two domain boundaries. In order to determine the interactions of the PDGFRA promoter, the interaction scores of all points in the region with the PDGFRA promoter (chr4:55,090,000) were plotted as a one-dimensional trace. In order to view the topological domain structure of the region, HiC interaction scores were visualized using Juicebox (www.aidenlab.org/juicebox/)[15]. Data shown is from the IMR90 cell line at 5 kb resolution, normalized to coverage.

DNA Methylation Quantification—DNA methylation was analyzed in two ways. For gliomaspheres, genomic DNA was isolated via QiaAmp® DNA minikit (Qiagen®) and subjected to Bisulfite Conversion (EZ DNA Methylation Gold™ Kit—Zymo Research). Bisulfite converted DNA specific to the CTCF binding site (defined by JASPAR[40]) in the boundary adjacent to PDGFRA was amplified using the following primers F: 5'-GAA TTA TAG ATA ATG TAG TTA GAT GG-3' (SEQ ID NO: 33), R: 5'-AAA TAT ACT AAT CCT CCT CTC CCA AA-3' (SEQ ID NO: 34). Amplified DNA was used to prepare a sequencing library, which was sequenced as 38 base paired-end reads on a NextSeq500. For tumors, limiting DNA yields required an alternate strategy for methylation analysis. Tumor genomic DNA was isolated from minced frozen sections of tumors by QiaAmp® DNA minikit (Qiagen®). Genomic DNA was digested using the methylation-sensitive restriction enzyme Hin6I (Thermo) recognizing the restriction site GCGC, or subjected to mock digestion. Protected DNA was quantified by PCR using the following primer set: PDGFRAinsF: 5'-CGT GAG CTG AAT TGT GCC TG-3' (SEQ ID NO: 35), PDGFRAinsR: 5'-TGG GAG GAC AGT TTA GGG CT-3'_(SEQ ID NO: 36), normalizing to mock digestion.

Chromatin Conformation Capture (3C)—3C analysis was performed using procedures as described previously[41,42]. Briefly, ~10 million cell equivalents from minced tumor specimens or gliomasphere cultures were fixed in 1% formaldehyde. Fixed samples were lysed in lysis buffer containing 0.2% PMSF using a Dounce Pestle. Following lysis, samples were digested with HinDIII (NEB) overnight on a thermomixer at 37° C. rotating at 950 RPM. Diluted samples were ligated using T4 DNA ligase (NEB) at 16° C. overnight, followed by RNase and Proteinase K treatment. DNA was extracted via phenol/chloroform/isoamyl alcohol (Invitrogen™). DNA was analyzed via TaqMan PCR using ABI master mix. Primers and probe were synthesized by IDT with the following sequences: Common PDGFRA Promoter: 5'-GGT CGT GCC TTT GTT TT-3'_(SEQ ID NO: 37), FIP1L1 Control: 5'-CAG GGA AGA GAG GAA GTT T-3'_(SEQ ID NO: 38), FIP1L1 Enhancer: 5'-TTA AGT AAG CAG GTA AAC TAC AT-3'_(SEQ ID NO: 39), Intragenic Enhancer: 5'-AGC CTT TGC CTC CTT TT-3' (SEQ ID NO: 40), Intragenic Control: 5'-CCA CAG GGA GAA GGA AAT-3'_(SEQ ID NO: 41), Intact Promoter: 5'-CAA GGA ATT CGT AGG GTT C-3'_(SEQ ID NO: 42), Probe: 5'-/56-FAM/TTG TAT GCG/ZEN/AGA TAG AAG CCA GGG CAA/3IABkFQ/-3'_(SEQ ID NOs: 43 and 44). For the reciprocal FIP1L1 enhancer interaction interrogation, the following primer sequences were used: Common Enhancer Primer—as FIP1L1 Enhancer Primer above (5'-TTA AGT AAG CAG GTA AAC TAC AT-3') (SEQ ID NO: 39), PDGFRA Promoter—as Common PDGFRA Promoter above (5'-GGT CGT GCC TTT GTT TT-3') (SEQ ID NO: 37), SCFD2 Promoter-5'-AAT ACA TGG TCA TGA TGC TC-3' (SEQ ID NO: 45), FIP1L1 Promoter—5'-AGG CAT TGC TTA AAC ATA AC-3' (SEQ ID NO: 46), FIP1L1 control—5'-TTA TTT GTA GTA GAG GTT ACT GG-3' (SEQ ID NO: 47), PDGFRA control—5'-ATG ATA ACA CCA CCA TTC AG-3' (SEQ ID NO: 48), FIP1L1 enhancer Probe—5'-/56-FAM/TAT CCC AAC/ZEN/CAA ATA CAG GGC TTG G/3IABkFQ/-3' (SEQ ID NOs: 49 and 50). In order to normalize primer signals, Bacterial Artificial Chromosome (BAC) clones CTD-2022B5 and RP11-626H4 were obtained from Invitrogen™. BAC DNA was purified via BACMAX DNA Purification kit (Epicenter) and quantified using two primer sets specific to the Chloramphenicol resistance gene: 1F: 5'-TTC GTC TCA GCC AAT CCC TG-3' (SEQ ID NO: 51), 1R: 5'-TTT GCC CAT GGT GAA AAC GG-3' (SEQ ID NO: 52), 2F: GGT TCA TCA TGC CGT TTG TG-3'(SEQ ID NO: 53), 2R: 5'-CCA CTC ATC GCA GTA CTG TTG-3' (SEQ ID NO: 54). BAC DNA was subjected to a similar 3C protocol, omitting steps related to cell lysis, proteinase or RNase treatment. PCR signal from tumor and gliomasphere 3C was normalized to digestion efficiency and BAC primer signal.

Treatment with demethylating agent—BT142 cells were cultured in either 5 µM 5-azacytidine or equivalent DMSO (1:10,000) for 8 days, with drug refreshed every 2 days.

CRISPR/Cas9 Insulator Disruption—The following CRISPR small guide RNAs were cloned into the LentiCRISPR vector obtained from the Zhang lab[43]: GFP: 5'-GAG CTG GAC GGC GAC GTA AA-3' (SEQ ID NO: 55), Insulator: 5'-GCC ACA GAT AAT GCA GCT AGA-3' (SEQ ID NO: 56). GSC6 gliomaspheres were mechanically dissociated and plated in 5 µg/mL EHS Laminin (Sigma-Aldrich™) and allowed to adhere overnight and then infected with lentivirus containing either CRISPR vector for 48h. Cells were then selected in 1 µg/mL puromycin for four days, with puromycin-containing media refreshed every two days. Genomic DNA was isolated and the region of interest was amplified using the PDGFRAins primer set described above. CRISPR-mediated disruption of this amplified DNA was confirmed via Surveyor® Assay (Transgenomic®), with amplified uninfected GSC6 genomic DNA being added to each annealing reaction as the unmodified control. In order to quantify the precise CRISPR alterations, genomic DNA from each construct was amplified using a set of primers closer to the putative deletion site as follows: F: 5'-TTT GCA ATG GGA CAC CGA GA-3' (SEQ ID NO: 57), R: 5'-AGA AAT GTG TGG ATG TGA GCG-3' (SEQ ID NO: 58). PCR product from these primers was used to prepare a library that was sequenced as 38 base paired-end reads on the Illumina® NextSeq500.

PDGFRA Quantitative PCR—Total RNA was isolated from CRISPR-infected GSC6 gliomaspheres (Insulator or control GFP sgRNA) or BT142 gliomaspheres (5-aza treated or control condition) using the RNeasy® minikit (Qiagen®) and used to synthesize cDNA with the SuperScript™ III system (Invitrogen™). cDNA was analyzed using SYBR™ mastermix (Applied Biosystems™) on a 7500 Fast Real Time System (Applied Biosystems™). PDGFRA expression was determined using the following primers: F: 5'-GCT CAG CCC TGT GAG AAG AC-3' (SEQ ID NO: 59), R: 5'-ATT GCG GAA TAA CAT CGG AG-3' (SEQ ID NO: 60), and was normalized to primers for Ribosomal Protein, large, PO (RPLPO), as follows: F: 5'-TCC CAC TTG CTG AAA AGG TCA-3' (SEQ ID NO: 61), R: 5'-CCG ACT CTT CCT TGG CTT CA-3' (SEQ ID NO: 62). Normalization was also verified by β-actin, F: 5'-AGA AAA TCT GGC ACC ACA CC-3' (SEQ ID NO: 63), R: 5'-AGA GGC GTA CAG GGA TAG CA-3' (SEQ ID NO: 64).

PDGFRA Flow Cytometry—Cells were incubated with PE-conjugated anti-PDGFRA (CD140a) antibody (Biolegend®, clone 16A1) for 30 minutes at room temperature at the dilution specified in the manufacturer's protocol. Data was analyzed and visualized with FlowJo software. Single live cells were selected for analysis via side and forward scatter, and viable cells were selected by lack of an unstained channel (APC) autofluorescence.

Cell Growth Assay—For the cell growth assay, 2,500 dissociated viable GSC6 cells expressing CRISPR and either GFP or Insulator targeting sgRNA (see above) were plated in 1004, of media in an opaque-walled tissue culture 96 well plate, in 1 µM Dasatinib, 500 nM Crenolanib, or equivalent DMSO (1:10,000) as a vehicle control. Cell growth was analyzed at days 3, 5, and 7 for Dasatinib, or days 3, 7, and 10 for Crenolanib, using CellTiter-Glo® reagent (Promega™) following the manufacturer's protocol. Data was normalized across days using an ATP standard curve.

REFERENCES

1 Parsons, D. W. et al. An integrated genomic analysis of human glioblastoma multiforme. *Science* 321, 1807-1812, doi:10.1126/science.1164382 (2008).

2 The Cancer Genome Atlas Research Network. Comprehensive, Integrative Genomic Analysis of Diffuse Lower-Grade Gliomas. *The New England journal of medicine* 372, 2481-2498, doi:10.1056/NEJMoa1402121 (2015).

3 Dang, L. et al. Cancer-associated IDH1 mutations produce 2-hydroxyglutarate. *Nature* 462, 739-744, doi:10.1038/nature08617 (2009).

4 Figueroa, M. E. et al. Leukemic IDH1 and IDH2 mutations result in a hypermethylation phenotype, disrupt TET2 function, and impair hematopoietic differentiation. *Cancer cell* 18, 553-567, doi:10.1016/j.ccr.2010.11.015 (2010).

5 Xu, W. et al. Oncometabolite 2-hydroxyglutarate is a competitive inhibitor of alpha-ketoglutarate-dependent dioxygenases. *Cancer cell* 19, 17-30, doi:10.1016/j.ccr.2010.12.014 (2011).

6 Lu, C. et al. IDH mutation impairs histone demethylation and results in a block to cell differentiation. *Nature* 483, 474-478, doi:10.1038/nature10860 (2012).

7 Cairns, R. A. & Mak, T. W. Oncogenic isocitrate dehydrogenase mutations: mechanisms, models, and clinical opportunities. *Cancer discovery* 3, 730-741, doi:10.1158/2159-8290.CD-13-0083 (2013).

8 Pastor, W. A., Aravind, L. & Rao, A. TETonic shift: biological roles of TET proteins in DNA demethylation and transcription. *Nature reviews. Molecular cell biology* 14, 341-356, doi:10.1038/nrm3589 (2013).
9. Kohli, R. M. & Zhang, Y. TET enzymes, TDG and the dynamics of DNA demethylation. *Nature* 502, 472-479, doi:10.1038/nature12750 (2013).
10. Noushmehr, H. et al. Identification of a CpG island methylator phenotype that defines a distinct subgroup of glioma. *Cancer cell* 17, 510-522, doi:10.1016/j.ccr.2010.03.017 (2010).
11. Turcan, S. et al. IDH1 mutation is sufficient to establish the glioma hypermethylator phenotype. *Nature* 483, 479-483, doi:10.1038/nature10866 (2012).
12. Bickmore, W. A. & van Steensel, B. Genome architecture: domain organization of interphase chromosomes. *Cell* 152, 1270-1284, doi:10.1016/j.cell.2013.02.001 (2013).
13. Lieberman-Aiden, E. et al. Comprehensive mapping of long-range interactions reveals folding principles of the human genome. *Science* 326, 289-293, doi:10.1126/science.1181369 (2009).
14. Dixon, J. R. et al. Topological domains in mammalian genomes identified by analysis of chromatin interactions. *Nature* 485, 376-380, doi:10.1038/nature11082 (2012).
15. Rao, S. S. et al. A 3D map of the human genome at kilobase resolution reveals principles of chromatin looping. *Cell* 159, 1665-1680, doi:10.1016/j.cell.2014.11.021 (2014).
16. Nora, E. P. et al. Spatial partitioning of the regulatory landscape of the X-inactivation centre. *Nature* 485, 381-385, doi:10.1038/nature11049 (2012).
17. Lupianez, D. G. et al. Disruptions of topological chromatin domains cause pathogenic rewiring of gene-enhancer interactions. *Cell* 161, 1012-1025, doi:10.1016/j.cell.2015.04.004 (2015).
18. Bell, A. C. & Felsenfeld, G. Methylation of a CTCF-dependent boundary controls imprinted expression of the Igf2 gene. *Nature* 405, 482-485, doi:10.1038/35013100 (2000).
19. Hark, A. T. et al. CTCF mediates methylation-sensitive enhancer-blocking activity at the H19/Igf2 locus. *Nature* 405, 486-489, doi:10.1038/35013106 (2000).
20. The GTEx Consortium. The Genotype-Tissue Expression (GTEx) pilot analysis: multitissue gene regulation in humans. *Science* 348, 648-660, doi:10.1126/science.1262110 (2015).
21. Zuin, J. et al. Cohesin and CTCF differentially affect chromatin architecture and gene expression in human cells. *Proceedings of the National Academy of Sciences of the United States of America* 111, 996-1001, doi:10.1073/pnas.1317788111 (2014).
22. Sturm, D. et al. Paediatric and adult glioblastoma: multiform (epi)genomic culprits emerge. *Nature reviews. Cancer* 14, 92-107, doi:10.1038/nrc3655 (2014).
23. Brennan, C. W. et al. The somatic genomic landscape of glioblastoma. *Cell* 155, 462-477, doi:10.1016/j.cell.2013.09.034 (2013).
24. Verhaak, R. G. et al. Integrated genomic analysis identifies clinically relevant subtypes of glioblastoma characterized by abnormalities in PDGFRA, IDH1, EGFR, and NF1. *Cancer cell* 17, 98-110, doi:10.1016/j.ccr.2009.12.020 (2010).
25. Wang, H. et al. Widespread plasticity in CTCF occupancy linked to DNA methylation. *Genome research* 22, 1680-1688, doi:10.1101/gr.136101.111 (2012).
26. Hsu, P. D., Lander, E. S. & Zhang, F. Development and applications of CRISPR-Cas9 for genome engineering. *Cell* 157, 1262-1278, doi:10.1016/j.cell.2014.05.010 (2014).
27. Sander, J. D. & Joung, J. K. CRISPR-Cas systems for editing, regulating and targeting genomes. *Nature biotechnology* 32, 347-355, doi:10.1038/nbt.2842 (2014).
28. Baylin, S. B. & Jones, P. A. A decade of exploring the cancer epigenome—biological and translational implications. *Nature reviews. Cancer* 11, 726-734, doi:10.1038/nrc3130 (2011).
29. Costello, J. F., Berger, M. S., Huang, H. S. & Cavenee, W. K. Silencing of p16/CDKN2 expression in human gliomas by methylation and chromatin condensation. *Cancer research* 56, 2405-2410 (1996).
30. Koivunen, P. et al. Transformation by the (R)-enantiomer of 2-hydroxyglutarate linked to EGLN activation. *Nature* 483, 484-488, doi:10.1038/nature10898 (2012).
31. Chi, A. S. et al. Prospective, high-throughput molecular profiling of human gliomas. *Journal of neuro-oncology* 110, 89-98, doi:10.1007/s11060-012-0938-9 (2012).
32. Rheinbay, E. et al. An aberrant transcription factor network essential for Wnt signaling and stem cell maintenance in glioblastoma. *Cell reports* 3, 1567-1579, doi:10.1016/j.celrep.2013.04.021 (2013).
33. Suva, M. L. et al. Reconstructing and reprogramming the tumor-propagating potential of glioblastoma stem-like cells. *Cell* 157, 580-594, doi:10.1016/j.cell.2014.02.030 (2014).
34. Wakimoto, H. et al. Maintenance of primary tumor phenotype and genotype in glioblastoma stem cells. *Neuro-oncology* 14, 132-144, doi:10.1093/neuonc/nor195 (2012).
35. Luchman, H. A. et al. An in vivo patient-derived model of endogenous IDH1-mutant glioma. *Neuro-oncology* 14, 184-191, doi:10.1093/neuonc/nor207 (2012).
36. Lai, R. K. et al. Genome-wide methylation analyses in glioblastoma multiforme. *PloS one* 9, e89376, doi:10.1371/journal.pone.0089376 (2014).
37. Abyzov, A., Urban, A. E., Snyder, M. & Gerstein, M. CNVnator: an approach to discover, genotype, and characterize typical and atypical CNVs from family and population genome sequencing. *Genome research* 21, 974-984, doi:10.1101/gr.114876.110 (2011).
38. Chudnovsky, Y. et al. ZFHX4 interacts with the NuRD core member CHD4 and regulates the glioblastoma tumor-initiating cell state. *Cell reports* 6, 313-324, doi:10.1016/j.celrep.2013.12.032 (2014).
39. Bao, S. et al. Targeting cancer stem cells through L1CAM suppresses glioma growth. *Cancer research* 68, 6043-6048, doi:10.1158/0008-5472.CAN-08-1079 (2008).
40. Sandelin, A., Alkema, W., Engstrom, P., Wasserman, W. W. & Lenhard, B. JASPAR: an open-access database for eukaryotic transcription factor binding profiles. *Nucleic acids research* 32, D91-94, doi:10.1093/nar/gkh012 (2004).
41. de Laat, W. & Dekker, J. 3C-based technologies to study the shape of the genome. *Methods* 58, 189-191, doi:10.1016/j.ymeth.2012.11.005 (2012).
42. Hagege, H. et al. Quantitative analysis of chromosome conformation capture assays (3C-qPCR). *Nature protocols* 2, 1722-1733, doi:10.1038/nprot.2007.243 (2007).
43. Cong, L. et al. Multiplex genome engineering using CRISPR/Cas systems. *Science* 339, 819-823, doi:10.1126/science.1231143 (2013).
44. Cahoy, J. D. et al. A transcriptome database for astrocytes, neurons, and oligodendrocytes: a new resource for understanding brain development and function. *The Journal of neuroscience: the official journal of the Society for Neuroscience* 28, 264-278, doi:10.1523/JNEUROSCI.4178-07.2008 (2008).

The invention is further described by the following numbered paragraphs:

1. A method of detecting cancer in a subject comprising detecting in a biological sample obtained from the subject altered chromatin topology within a chromatin region, wherein said chromatin region comprises at least one distinct topologically-associated domain partitioned by insulator sites, wherein at least one of said insulator sites comprises a CpG dinucleotide within a CTCF binding motif, and wherein the chromatin region comprises an oncogene, whereby the detection of altered chromatin topology is indicative of cancer in said subject.

2. The method according to paragraph 1, wherein the chromatin region comprises a regulatory element.

3. The method according to paragraph 2, wherein the regulatory element is an enhancer.

4. The method according to paragraph 1, wherein the subject is in cancer remission, has a genetic disorder which predisposes a subject to cancer, or has been exposed to a carcinogen.

5. The method according to paragraph 1, wherein the biological sample is blood, sputum, saliva, urine, tumor tissue, lymphatic fluid, semen, feces, biopsy, or circulating tumor cells.

6. The method according to paragraph 1, wherein detecting altered chromatin topology comprises detecting 5-methyl cytosine at the CpG dinucleotide.

7. The method according to paragraph 1, wherein detecting altered chromatin topology comprises detecting 5-hydroxymethylcytosine at the CpG dinucleotide.

8. The method according to paragraph 1, further comprising detecting a gain of function mutation in the gene encoding isocitrate dehydrogenase (IDH) or a loss of function mutation in a gene encoding a succinate dehydrogenase.

9. The method according to paragraph 4, wherein said cancer is a cholangiocarcinoma, leukemia, a chondrosarcoma, a gastrointestinal stromal tumor (GIST), a pheochromocytoma, a paraganglioma, breast cancer, thyroid cancer, colon cancer, melanoma, bladder cancer, ovarian cancer, lung cancer, glioma, kidney cancer, stomach cancer, pancreatic cancer, liver cancer, or neuroblastoma.

10. The method according to paragraph 4, wherein said genetic disorder is Ollier Disease, Mafucci syndrome, Carney-Stratakis Syndrome, or a variant of Cowden Syndrome which predisposes to breast and thyroid cancer.

11. The method according to any of paragraphs 1 to 10, wherein the oncogene is PDGFRA, FGFR2, other RTKs, or other tumorigenic drivers.

12. The method according to paragraph 1, wherein altered chromatin topology is detected by chromosome conformation capture (3C), DNA hypersensitivity, CTCF binding, methylation specific PCR, Ms-SNuPE, bisulfite sequencing, methylation sensitive restriction digest, nanopore sequencing or DNA FISH.

13. A method of monitoring disease progression in a subject diagnosed with cancer or a genetic disorder which predisposes the subject to cancer comprising detecting in a biological sample obtained from the subject after diagnosis, altered chromatin topology within a chromatin region, wherein said chromatin region comprises at least one distinct topologically-associated domain partitioned by insulator sites, wherein at least one of said insulator sites comprises a CpG dinucleotide within a CTCF binding motif, and wherein chromatin region comprises an oncogene, whereby an increase in the detection of altered chromatin topology is an indication of rapid disease progression.

14. The method according to paragraph 13, wherein the chromatin region comprises a regulatory element.

15. The method according to paragraph 14, wherein the regulatory element is an enhancer.

16. The method according to paragraph 13, wherein the biological sample is blood, sputum, saliva, urine, tumor tissue, lymphatic fluid, semen, feces, biopsy, or circulating tumor cells.

17. The method according to paragraph 13, wherein detecting altered chromatin topology comprises detecting 5-methyl cytosine at the CpG dinucleotide.

18. The method according to paragraph 13, wherein detecting altered chromatin topology comprises detecting 5-hydroxymethylcytosine at the CpG dinucleotide.

19. The method according to paragraph 13, further comprising detecting a gain of function mutation in the gene encoding isocitrate dehydrogenase (IDH) or a loss of function mutation in a gene encoding a succinate dehydrogenase.

20. The method according to paragraph 13, wherein said cancer is a cholangiocarcinoma, leukemia, a chondrosarcoma, a gastrointestinal stromal tumor (GIST), a pheochromocytoma, a paraganglioma, breast cancer, thyroid cancer, colon cancer, melanoma, bladder cancer, ovarian cancer, lung cancer, glioma, kidney cancer, stomach cancer, pancreatic cancer, liver cancer, or neuroblastoma.

21. The method according to paragraph 13, wherein said genetic disorder is Ollier Disease, Mafucci syndrome, Carney-Stratakis Syndrome, or a variant of Cowden Syndrome which predisposes to breast and thyroid cancer.

22. The method according to any of paragraphs 13 to 21, wherein the oncogene is PDGFRA, FGFR2, other RTKs, or other tumorigenic drivers.

23. The method according to paragraph 13, wherein altered chromatin topology is detected by chromosome conformation capture (3C), DNA hypersensitivity, CTCF binding, methylation specific PCR, Ms-SNuPE, bisulfite sequencing, methylation sensitive restriction digest, nanopore sequencing or DNA FISH.

24. A diagnostic method for selecting a subject to be administered a pharmaceutical composition, wherein the subject has cancer or a genetic disorder which predisposes the subject to cancer, said method comprising detecting altered chromatin topology within a chromatin region, wherein said chromatin region comprises at least one distinct topologically-associated domain partitioned by insulator sites, wherein at least one of said insulator sites comprises a CpG dinucleotide within a CTCF binding motif, and wherein the chromatin region comprises an oncogene, whereby a subject is selected if altered chromatin topology is detected.

25. The method according to paragraph 24, wherein the chromatin region comprises a regulatory element.

26. The method according to paragraph 25, wherein the regulatory element is an enhancer.

27. The diagnostic method of paragraph 24, wherein detecting altered chromatin topology comprises detecting 5-methyl cytosine at the CpG dinucleotide, whereby a subject is selected if 5-methyl cytosine is detected.

28. The diagnostic method of paragraph 24, wherein detecting altered chromatin topology comprises detecting 5-hydroxymethylcytosine at the CpG dinucleotide, whereby a subject is selected if 5-hydroxymethylcytosine is detected.

29. The method according to paragraph 24, further comprising detecting a gain of function mutation in the gene encoding isocitrate dehydrogenase (IDH) or a loss of function mutation in a gene encoding a succinate dehydrogenase.

30. The method according to paragraph 24, wherein altered chromatin topology is detected in a biological sample, wherein said biological sample is blood, sputum, saliva, urine, tumor tissue, lymphatic fluid, semen, feces, biopsy, or circulating tumor cells.

31. The method according to any of paragraphs 24 to 30, wherein said cancer is a cholangiocarcinoma, leukemia, a chondrosarcoma, a gastrointestinal stromal tumor (GIST), a pheochromocytoma, a paraganglioma, breast cancer, thyroid cancer, colon cancer, melanoma, bladder cancer, ovarian cancer, lung cancer, glioma, kidney cancer, stomach cancer, pancreatic cancer, liver cancer, or neuroblastoma.

32. The method according to any of paragraphs 24 to 30, wherein said genetic disorder is Ollier Disease, Mafucci syndrome, Carney-Stratakis Syndrome, or a variant of Cowden Syndrome which predisposes to breast and thyroid cancer.

33. The method according to any of paragraphs 24 to 32, wherein the oncogene is PDGFRA, FGFR2, other RTKs, or other tumorigenic drivers.

34. The method according to any of paragraphs 24 to 33, wherein said pharmaceutical composition comprises an agent that alters the topology of a chromatin domain.

35. The method according to paragraph 34, wherein said agent that alters the topology of a chromatin domain comprises an agent that alters an epigenetic mark within the chromatin domain.

36. The method according to paragraph 35, wherein the agent alters histone acetylation, histone methylation or DNA methylation.

37. The method according to any of paragraphs 24 to 33, wherein said pharmaceutical composition comprises an inhibitor of the oncogene.

38. The method according to paragraph 37, wherein the oncogene is PDGFRA.

39. The method according to paragraph 38, wherein said inhibitor is imatinib, crenolanib, or dasatinib.

40. The method according to any of paragraphs 24 to 33, wherein said pharmaceutical composition comprises an inhibitor of a dehydrogenase.

41. The method according to paragraph 40, wherein said dehydrogenase is isocitrate dehydrogenase (IDH).

42. The method according to any of paragraphs 24 to 33, wherein said pharmaceutical composition comprises an agent that edits the DNA sequence or the DNA methylation within the insulator site.

43. The method according to paragraph 42, wherein the agent is a CRISPR-Cas system, TALE, or Zinc-finger.

44. The method according to any of paragraphs 24 to 43, wherein said pharmaceutical composition comprises more than one agent.

45. The method according to paragraph 44, wherein said pharmaceutical composition comprises separate agents.

46. The method according to paragraph 45, wherein said pharmaceutical composition is administered sequentially.

47. The method of paragraph 46, wherein an agent that alters the topology of a chromatin domain is administered before an inhibitor of a dehydrogenase.

48. The method of paragraph 44 or 45, wherein said pharmaceutical composition comprises an inhibitor of a dehydrogenase and an inhibitor of the oncogene.

49. The method according to paragraph 24, wherein altered chromatin topology is detected by chromosome conformation capture (3C), DNA hypersensitivity, CTCF binding, methylation specific PCR, Ms-SNuPE, bisulfite sequencing, methylation sensitive restriction digest, nanopore sequencing or DNA FISH.

50. A method of treating a subject in need thereof having cancer or a genetic disorder which predisposes the subject to cancer, said method comprising administering a pharmaceutical composition to the subject,
wherein altered chromatin topology within a chromatin region is detected in the subject,
wherein said chromatin region comprises more than one distinct topologically-associated domains partitioned by insulator sites,
wherein at least one insulator site comprises a CpG dinucleotide within a CTCF binding motif, and
wherein at least one topologically-associated domain comprises an oncogene.

51. The method according to paragraph 50, wherein the chromatin region comprises a regulatory element.

52. The method according to paragraph 51, wherein the regulatory element is an enhancer.

53. The method according to paragraph 50, wherein detecting altered chromatin topology comprises detecting 5-methyl cytosine at the CpG dinucleotide.

54. The method according to paragraph 50, wherein detecting altered chromatin topology comprises detecting 5-hydroxymethylcytosine at the CpG dinucleotide.

55. The method according to paragraph 50, wherein the subject has a gain of function mutation in the gene encoding isocitrate dehydrogenase (IDH), a loss-of-function mutation in the gene encoding a succinate dehydrogenase, or other genetic mutation that confers DNA hyper-methylation.

56. The method according to paragraph 50, wherein the subject has a DNA hypermethylation phenotype.

57. The method according to paragraph 50, wherein altered chromatin topology is detected in a biological sample, wherein said biological sample is blood, sputum, saliva, urine, tumor tissue, lymphatic fluid, semen, feces, biopsy, or circulating tumor cells.

58. The method according to any of paragraphs 50 to 57, wherein said cancer is a cholangiocarcinoma, leukemia, a chondrosarcoma, a gastrointestinal stromal tumor (GIST), a pheochromocytoma, a paraganglioma, breast cancer, thyroid cancer, colon cancer, melanoma, bladder cancer, ovarian cancer, lung cancer, glioma, kidney cancer, stomach cancer, pancreatic cancer, liver cancer, or neuroblastoma.

59. The method according to any of paragraphs 50 to 57, wherein said genetic disorder is Ollier Disease, Mafucci syndrome, Carney-Stratakis Syndrome, or a variant of Cowden Syndrome which predisposes to breast and thyroid cancer.

60. The method according to any of paragraphs 50 to 59, wherein the oncogene is PDGFRA, FGFR2, other RTKs, or other tumorigenic drivers.

61. The method according to any of paragraphs 50 to 60, wherein said pharmaceutical composition comprises an agent that alters the topology of a chromatin domain.

62. The method according to paragraph 61, wherein said agent that alters the topology of a chromatin domain comprises an agent that alters an epigenetic mark within at least one insulator site at the boundary of a chromatin domain.

63. The method according to paragraph 62, wherein the agent alters histone acetylation, histone methylation or DNA methylation.

64. The method according to any of paragraphs 50 to 63, wherein said pharmaceutical composition comprises an inhibitor of the oncogene.

65. The method according to paragraph 64, wherein the oncogene is PDGFRA.

66. The method according to paragraph 65, wherein said inhibitor is imatinib, crenolanib, or dasatinib.

67. The method according to any of paragraphs 50 to 66, wherein said pharmaceutical composition comprises an inhibitor of a dehydrogenase.

68. The method according to paragraph 67, wherein said dehydrogenase is isocitrate dehydrogenase (IDH).

69. The method according to any of paragraphs 50 to 68, wherein said pharmaceutical composition comprises an agent that edits the sequence or edits DNA methylation within the insulator site.

70. The method according to paragraph 69, wherein the agent is a CRISPR-Cas system, TALE, or Zinc-finger.

71. The method according to any of paragraphs 50 to 68, wherein said pharmaceutical composition comprises a DNA targeting agent.

72. The method according to paragraph 71, wherein the DNA targeting agent is a CRISPR-Cas system, TALE, or Zinc-finger.

73. The method according to paragraph 72, wherein the CRISPR-Cas system comprises an enzymatically inactive CRISPR enzyme.

74. The method according to paragraph 73, wherein the enzymatically inactive CRISPR enzyme is fused to a functional domain.

75. The method according to paragraph 74, wherein the functional domain is a repressor, activator, DNA modifying enzyme, or histone modifying enzyme.

76. The method according to any of paragraphs 69 to 75, wherein the agent is inducible.

77. The method according to any of paragraphs 50 to 76, wherein said pharmaceutical composition comprises more than one agent.

78. The method according to paragraph 77, wherein said pharmaceutical composition comprises separate agents.

79. The method according to paragraph 78, wherein said pharmaceutical composition is administered sequentially.

80. The method according to paragraph 79, wherein an agent that alters the topology of a chromatin domain is administered before an inhibitor of a dehydrogenase.

81. The method according to paragraph 77 or 78, wherein said pharmaceutical composition comprises an inhibitor of a dehydrogenase and an inhibitor of the oncogene.

82. The method according to paragraph 50, wherein altered chromatin topology is detected by chromosome conformation capture (3C), DNA hypersensitivity, CTCF binding, methylation specific PCR, Ms-SNuPE, bisulfite sequencing, methylation sensitive restriction digest, nanopore sequencing or DNA FISH.

83. The method according to any of the preceding paragraphs, wherein altered chromatin topology is the result of decreased binding of CTCF as compared to a normal, non-cancerous cell.

84. The method according to paragraph 83, wherein aberrant interactions between topologically-associated domains result in altered gene expression.

85. The method according to any of paragraphs 83 to 84, wherein the aberrant interactions are aberrant enhancer-gene interactions.

86. The method according to any of paragraphs 83 to 85, wherein the topologically-associated domains are adjacent to the boundary site.

87. A method of screening for the onset or predisposition to the onset of cancer in a subject, said method comprising assessing the methylation status of at least one CpG dinucleotide within a CTCF binding motif in a biological sample from said subject, whereby a higher level of methylation of said CTCF binding motif relative to control levels is indicative of cancer or predisposition to the onset of cancer.

88. The method of screening according to paragraph 87, wherein the methylation status is assessed at a CTCF binding motif in one or more genomic regions listed in Table 51.

89. The method of screening according to paragraph 87, wherein the methylation status is assessed at a CTCF binding motif associated with the PDGFRA gene.

90. The method of screening according to paragraph 87, wherein the methylation status is assessed at a CTCF binding motif associated with the FGFR2 gene.

91. The method of screening according to paragraph 87, wherein the methylation status is assessed by methylation specific PCR, Ms-SNuPE, bisulfate sequencing, methylation sensitive restriction digest, or nanopore sequencing.

92. A method of screening for the onset or predisposition to the onset of cancer in a subject, said method comprising assessing aberrant chromatin looping in a biological sample from said subject, whereby detection of aberrant chromatin looping is indicative of cancer or predisposition to the onset of cancer.

93. The method of screening according to paragraph 92, wherein the aberrant chromatin looping is assessed at a CTCF binding motif in one or more genomic regions listed in Table S1.

94. The method of screening according to paragraph 92, wherein the aberrant chromatin looping is assessed at a CTCF binding motif associated with the PDGFRA gene.

95. The method of screening according to paragraph 92, wherein the aberrant chromatin looping is assessed at a CTCF binding motif associated with the FGFR2 gene.

96. The method of screening according to paragraph 92, wherein the aberrant chromatin looping is assessed by DNA FISH.

97. A method of disrupting CTCF binding to an insulator comprising recruiting dCas9 to the insulator.

98. The method according to paragraph 97, wherein the dCas9 is fused to a functional domain.

99. The method according to paragraph 98, wherein the functional domain is a repressor protein.

100. The method according to paragraph 99, wherein the repressor protein is KRAB.

101. The method according to paragraph 97, wherein the insulator is enriched in H3K9me3.

102. The method according to any of the preceding paragraphs, wherein altered chromatin topology comprises a disruption in two or more topologically-associated domains such that the domains have aberrant interactions as compared to chromatin from a normal, non-cancerous subject.

103. The method according to paragraph 102, wherein at least one insulator site within a boundary at each of the two or more topologically-associated domains has decreased CTCF binding as compared to chromatin from a normal, non-cancerous subject.

104. A pharmaceutical composition for use in a method for treating a subject having cancer or a genetic disorder which predisposes the subject to cancer, wherein said subject displays altered chromatin topology within a chromatin region, wherein said chromatin region comprises more than one distinct topologically-associated domain partitioned by an insulator site, wherein said insulator site comprises a CpG dinucleotide within a CTCF binding motif, and wherein at least one domain comprises an oncogene.

105. The pharmaceutical composition according to paragraph 104, wherein at least one other domain comprises a regulatory element.

106. The pharmaceutical composition according to paragraph 105, wherein the regulatory element is an enhancer.

107. The pharmaceutical composition of paragraph 104, wherein detecting altered chromatin topology comprises detecting 5-methyl cytosine at the CpG dinucleotide.

108. The pharmaceutical composition of paragraph 104, wherein detecting altered chromatin topology comprises detecting 5-hydroxymethylcytosine at the CpG dinucleotide.

109. The pharmaceutical composition according to paragraph 104, wherein the subject has a gain of function mutation in the gene encoding isocitrate dehydrogenase (IDH), a loss-of-function mutation in the gene encoding a succinate dehydrogenase, or other genetic mutation that confers DNA hyper-methylation.

110. The pharmaceutical composition according to paragraph 104, wherein the subject has a DNA hypermethylation phenotype.

111. The pharmaceutical composition according to paragraph 104, wherein altered chromatin topology is detected in a biological sample, wherein said biological sample is blood, sputum, saliva, urine, tumor tissue, lymphatic fluid, semen, feces, biopsy, or circulating tumor cells.

112. The pharmaceutical composition according to any of paragraphs 104 to 100, wherein said cancer is a cholangiocarcinoma, leukemia, a chondrosarcoma, a gastrointestinal stromal tumor (GIST), a pheochromocytoma, a paraganglioma, breast cancer, thyroid cancer, colon cancer, melanoma, bladder cancer, ovarian cancer, lung cancer, glioma, kidney cancer, stomach cancer, pancreatic cancer, liver cancer, or neuroblastoma.

113. The pharmaceutical composition according to any of paragraphs 104 to 101, wherein said genetic disorder is Ollier Disease, Mafucci syndrome, Carney-Stratakis Syndrome, or a variant of Cowden Syndrome which predisposes to breast and thyroid cancer.

114. The pharmaceutical composition according to any of paragraphs 104 to 102, wherein the oncogene is PDGFRA, FGFR2, other RTKs, or other tumorigenic drivers.

115. The pharmaceutical composition according to any of paragraphs 104 to 103, wherein said pharmaceutical composition comprises an agent that alters the topology of a chromatin domain.

116. The pharmaceutical composition according to paragraph 115, wherein said agent that alters the topology of a chromatin domain comprises an agent that alters an epigenetic mark within the chromatin domain.

117. The pharmaceutical composition according to paragraph 1116, wherein the agent alters histone acetylation, histone methylation or DNA methylation.

118. The pharmaceutical composition according to any of paragraphs 104 to 117, wherein said pharmaceutical composition comprises an inhibitor of the oncogene.

119. The pharmaceutical composition according to paragraph 118, wherein the oncogene is PDGFRA.

120. The pharmaceutical composition according to paragraph 119, wherein said inhibitor is imatinib, crenolanib, or dasatinib.

121. The pharmaceutical composition according to any of paragraphs 104 to 109, wherein said pharmaceutical composition comprises an inhibitor of a dehydrogenase.

122. The pharmaceutical composition according to paragraph 121, wherein said dehydrogenase is isocitrate dehydrogenase (IDH).

123. The pharmaceutical composition according to any of paragraphs 104 to 122, wherein said pharmaceutical composition comprises an agent that edits the sequence or edits DNA methylation within the insulator site.

124. The pharmaceutical composition according to paragraph 122, wherein the agent is a CRISPR-Cas system, TALE, or Zinc-finger.

125. The pharmaceutical composition according to any of paragraphs 104 to 124, wherein said pharmaceutical composition comprises more than one agent.

126. The pharmaceutical composition according to paragraph 125, wherein said pharmaceutical composition comprises separate agents.

127. The pharmaceutical composition according to paragraph 126, wherein said pharmaceutical composition is administered sequentially.

128. The pharmaceutical composition of paragraph 127, wherein an agent that alters the topology of a chromatin domain is administered before an inhibitor of a dehydrogenase.

129. The pharmaceutical composition of paragraph 125 or 126, wherein said pharmaceutical composition comprises an inhibitor of a dehydrogenase and an inhibitor of the oncogene.

130. The pharmaceutical composition according to paragraph 104, wherein altered chromatin topology is detected by chromosome conformation capture (3C), DNA hypersensitivity, CTCF binding, methylation specific PCR, Ms-SNuPE, bisulfite sequencing, methylation sensitive restriction digest, nanopore sequencing or DNA FISH.

131. The pharmaceutical composition according to any of the preceding paragraphs, wherein altered chromatin topology comprises a disruption in two or more topologically-associated domains such that the domains have aberrant interactions as compared to chromatin from a normal, non-cancerous subject.

132. The pharmaceutical composition of paragraph 131, wherein at least one chromatin loop within the insulator site that partition the two or more topologically-associated domains are disrupted.

133. The pharmaceutical composition according to paragraph 131 or 132, wherein altered chromatin topology is the result of decreased binding of CTCF as compared to a normal, non-cancerous cell.

134. The pharmaceutical composition according to any of paragraphs 131 to 133, wherein aberrant interactions between topologically-associated domains results in altered gene expression.

135. The pharmaceutical composition according to any of paragraphs 131 to 134, wherein the aberrant interactions are aberrant enhancer-gene interactions.

136. The pharmaceutical composition according to any of paragraphs 131 to 135, wherein the topologically-associated domains are adjacent to the insulator site.

137. A pharmaceutical composition for use in a method for treating a subject having cancer or a genetic disorder which predisposes to cancer, wherein said subject has been selected according to the method of paragraph 24.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of detecting and treating a glioma in a subject, the method comprising:
   detecting in a brain biopsy sample obtained from the subject altered chromatin topology, relative to an appropriate control, within a chromatin region comprising at least one distinct topologically-associated domain partitioned by insulator sites, wherein at least one of said insulator sites comprises a CpG dinucleotide within a CTCF binding motif, and wherein the chromatin region comprises an oncogene selected from the group consisting of PDGFRA and FIP1L1, thereby identifying the subject as having a glioma, and administering a glioma therapy to the subject.

2. The method according to claim 1, wherein the chromatin region comprises a regulatory element.

3. The method according to claim 2, wherein the regulatory element is an enhancer.

4. The method according to claim 1, wherein the subject is in cancer remission, has a genetic disorder which predisposes the subject to cancer, or has been exposed to a carcinogen.

5. The method according to claim 4, wherein said genetic disorder is Ollier Disease, Mafucci syndrome, Carney-Stratakis Syndrome, or a variant of Cowden Syndrome which predisposes the subject to breast or thyroid cancer.

6. The method according to claim 1, wherein detecting altered chromatin topology comprises detecting 5-methyl cytosine at the CpG dinucleotide.

7. The method according to claim 1, wherein detecting altered chromatin topology comprises detecting 5-hydroxymethylcytosine at the CpG dinucleotide.

8. The method according to claim 1, further comprising detecting a gain of function mutation in the gene encoding isocitrate dehydrogenase (IDH) or a loss of function mutation in a gene encoding a succinate dehydrogenase.

9. The method according to claim 1, wherein said glioma is an oligoastrocytoma or a glioblastoma.

10. The method according to claim 1, wherein the oncogene is PDGFRA.

11. The method according to claim 1, wherein altered chromatin topology is detected by chromosome conformation capture (3C), DNA hypersensitivity, CTCF binding, methylation specific PCR, Ms-SNuPE, bisulfate sequencing, methylation sensitive restriction digest, nanopore sequencing or DNA FISH.

12. The method according to claim 1, wherein the oncogene is FIP1L1.

13. The method according to claim 1, wherein the control is a biological sample obtained from a subject known not to have glioma.

14. The method according to claim 1, wherein the glioma therapy comprises a pharmaceutical composition comprising an inhibitor of the oncogene, optionally wherein said inhibitor is selected from the group consisting of imatinib, crenolanib and dasatinib.

15. The method according to claim 1, wherein the glioma therapy comprises a pharmaceutical composition comprising an inhibitor of a dehydrogenase, optionally a pharmaceutical composition comprising an inhibitor of isocitrate dehydrogenase (IDH).

16. The method according to claim 1, wherein the glioma therapy comprises a pharmaceutical composition comprising an agent that edits DNA sequence or modulates DNA methylation within one or more of the insulator sites, optionally wherein the agent is selected from the group consisting of a CRISPR-Cas system agent, a TALE agent and a Zinc-finger agent.

17. The method according to claim 1, wherein the glioma therapy comprises a pharmaceutical composition comprising two or more agents selected from the group consisting of an inhibitor of the oncogene, an inhibitor of a dehydrogenase and an agent that alters the topology of a chromatin domain, optionally wherein said pharmaceutical composition is administered sequentially, optionally wherein the agent that alters the topology of a chromatin domain is administered before the inhibitor of the dehydrogenase.

18. The method according to claim 1, wherein the subject exhibits a DNA hypermethylation phenotype.

19. The method according to claim 1, wherein the glioma therapy comprises a pharmaceutical composition comprising a DNA targeting agent, optionally wherein the DNA targeting agent is a CRISPR-Cas system agent, a TALE agent, or a Zinc-finger agent, optionally wherein the CRISPR-Cas system agent comprises an enzymatically inactive CRISPR enzyme, optionally wherein the enzymatically inactive CRISPR enzyme is fused to a functional domain or the CRISPR system comprises a guide RNA including a transcript recruitment sequence configured to recruit a functional domain, optionally wherein the functional domain is a repressor, activator, DNA modifying enzyme or histone modifying enzyme, optionally wherein the agent is inducible.

20. The method according to claim 1, wherein the altered chromatin topology comprises a disruption in two or more topologically-associated domains such that the domains exhibit aberrant interactions as compared to chromatin from a normal, non-cancerous subject, optionally wherein at least one insulator site within a boundary at each of the two or more topologically-associated domains exhibits decreased CTCF binding as compared to chromatin from a normal, non-cancerous subject.

21. The method according to claim 1, wherein the altered chromatin topology is the result of decreased binding of CTCF as compared to a normal, non-cancerous cell, optionally wherein aberrant interactions between topologically-associated domains result in altered gene expression, optionally wherein the aberrant interactions are aberrant enhancer-gene interactions, optionally wherein the topologically-associated domains are adjacent.

22. The method according to claim 1, wherein the glioma therapy comprises a pharmaceutical composition comprising dCas9 fused to a functional domain, optionally wherein the functional domain is a repressor protein, optionally wherein the repressor protein is KRAB.

23. The method of claim 1, wherein one or more of the insulator sites is enriched in H3K9me3.

24. A method of identifying and treating glioma progression in a subject diagnosed with glioma or a genetic disorder which predisposes the subject to glioma, the method comprising:
detecting in a brain biopsy sample obtained from the subject after diagnosis an increase in altered chromatin topology within a PDGFRA or FIP1L1 gene of human chromosome 4: 53.7-55.4 Mb as compared to an appropriate control, thereby identifying the subject as having glioma progression, and
administering a glioma therapy to the subject.

25. The method according to claim 24, wherein the chromatin region comprises a regulatory element, optionally wherein the regulatory element is an enhancer.

26. The method according to claim 24, wherein said human chromosome 4: 53.7-55.4 Mb comprises at least one distinct topologically-associated domain partitioned by insulator sites, wherein at least one of said insulator sites comprises a CpG dinucleotide within a CTCF binding motif, and wherein the chromatin region comprises an oncogene, and wherein detecting altered chromatin topology comprises detecting 5-methyl cytosine at the CpG dinucleotide and/or detecting 5-hydroxymethylcytosine at the CpG dinucleotide.

27. The method according to claim 24, further comprising detecting a gain of function mutation in the gene encoding isocitrate dehydrogenase (IDH) or a loss of function mutation in a gene encoding a succinate dehydrogenase.

28. The method according to claim 24:
wherein said glioma is an oligoastrocytoma or a glioblastoma;
wherein the altered chromatin topology alters PDGFRA gene expression; and/or
wherein altered chromatin topology is detected by chromosome conformation capture (3C), DNA hypersensitivity, CTCF binding, methylation specific PCR, Ms-SNuPE, bisulfate sequencing, methylation sensitive restriction digest, nanopore sequencing or DNA FISH.

29. A method of treating a subject in need thereof having glioma or a genetic disorder which predisposes the subject to glioma, said method comprising: detecting in a brain biopsy sample obtained from the subject altered chromatin topology within a chromatin region comprising at least one distinct topologically-associated domain partitioned by insulator sites, wherein at least one of said insulator sites comprises a CpG dinucleotide within a CTCF binding motif, and wherein the chromatin region comprises an oncogene selected from the group consisting of PDGFRA and FIP1L1; and administering a pharmaceutical composition to the subject.

* * * * *